United States Patent
Yu

(10) Patent No.: US 11,963,952 B2
(45) Date of Patent: *Apr. 23, 2024

(54) ANTI-ANDROGENS FOR THE TREATMENT OF METASTATIC CASTRATION-SENSITIVE PROSTATE CANCER

(71) Applicant: ARAGON PHARMACEUTICALS, INC., Los Angeles, CA (US)

(72) Inventor: Margaret K. Yu, Los Angeles, CA (US)

(73) Assignee: Aragon Pharmaceuticals, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/168,204

(22) Filed: Feb. 13, 2023

(65) Prior Publication Data

US 2023/0190722 A1 Jun. 22, 2023

Related U.S. Application Data

(63) Continuation of application No. 17/425,865, filed as application No. PCT/IB2020/050752 on Jan. 30, 2020.

(60) Provisional application No. 62/901,694, filed on Sep. 17, 2019, provisional application No. 62/836,920, filed on Apr. 22, 2019, provisional application No. 62/833,371, filed on Apr. 12, 2019, provisional application No. 62/822,312, filed on Mar. 22, 2019, provisional application No. 62/803,096, filed on Feb. 8, 2019, provisional application No. 62/798,836, filed on Jan. 30, 2019.

(51) Int. Cl.
| | | |
|---|---|---|
| A61K 31/4439 | (2006.01) | |
| A61K 31/4155 | (2006.01) | |
| A61K 31/4166 | (2006.01) | |
| A61P 5/28 | (2006.01) | |
| A61P 35/00 | (2006.01) | |

(52) U.S. Cl.
CPC ...... *A61K 31/4439* (2013.01); *A61K 31/4155* (2013.01); *A61K 31/4166* (2013.01); *A61P 5/28* (2018.01); *A61P 35/00* (2018.01)

(58) Field of Classification Search
None
See application file for complete search history.

(56) References Cited

U.S. PATENT DOCUMENTS

| | | |
|---|---|---|
| 8,445,507 B2 | 5/2013 | Jung et al. |
| 8,802,689 B2 | 8/2014 | Jung et al. |
| 9,388,159 B2 | 7/2016 | Jung et al. |
| 9,987,261 B2 | 6/2018 | Jung et al. |
| 2012/0225867 A1 | 9/2012 | Wohlfahrt et al. |
| 2014/0088129 A1 | 3/2014 | Chen |
| 2014/0199236 A1 | 7/2014 | Chen et al. |
| 2016/0220548 A1 | 8/2016 | Chen et al. |

FOREIGN PATENT DOCUMENTS

| | | |
|---|---|---|
| CN | 104857157 A | 8/2015 |
| TW | 201440767 A | 11/2014 |
| WO | 2014/043208 A1 | 3/2014 |
| WO | 2014/113260 A1 | 7/2014 |
| WO | 2016/090098 A1 | 6/2016 |
| WO | 2016/090101 A1 | 6/2016 |
| WO | 2016/090105 A1 | 6/2016 |

OTHER PUBLICATIONS

A Phase 3 Randomized, Placebo-controlled, Double-blind Study of Apalutamide Plus Androgen Deprivation Therapy (ADT) Versus ADT in Subjects With Metastatic Hormone-sensitive Prostate Cancer (mHSPC), NCT02489318, Jan. 2019, pp. 1-106.
Cetin et al., "Recent Time Trends in the Epidemiology of Stage IV Prostate Cancer in the United States: Analysis of Data From the Surveillance, Epidemiology, and End Results Program", Urology, 2010, vol. 75, pp. 1396-1405.
Chen et al., "Molecular Determinants of Resistance to Antiandrogen Therapy", Nature Medicine, 2003, vol. 10, No. 1, pp. 33-39.
Chi, K.N., et al., "Apalutamide for Metastatic, Castration-Sensitive Prostate Cancer", The New England Journal Of Medicine, vol. 381, No. 1, Jul. 4, 2019, pp. 13-24.
Clegg et al., "ARN-509: A Novel Antiandrogen for Prostate Cancer Treatment", Cancer Res; vol. 72, No. 6, Mar. 15, 2012, pp. 1494-1503.
Drazer et al., "National Prostate Cancer Screening Rates After the 2012 US Preventive Services Task Force Recommendation Discouraging Prostate-Specific Antigen-Based Screening", Journal of Clinical Oncology, 2015, vol. 33, pp. 2416-2423.
Flamand et al., "Observational survey on variations in incidence by stage of prostate cancer in the Nord-Pas-de-Calais region between 1998 and 2004", Prog Urok, 2008, 18, pp. 53-59.
Jessica smith: Astellas and Pfizer Announce Positive Top-Line Results from Phase 3 ARCHES Trial of XTANDI (enzalutamide) in Men with Metastatic Hormone-Sensitive Prostate Cancer, Dec. 20, 2018, pp. 1-6.

(Continued)

*Primary Examiner* — Brian J Davis
(74) *Attorney, Agent, or Firm* — BakerHostetler

(57) ABSTRACT

Described herein are methods of treating metastatic castration-sensitive prostate cancer with anti-androgens, including but not limited to, 4-[7-(6-cyano-5-trifluoromethylpyridin-3-yl)-8-oxo-6-thioxo-5,7-diazaspiro[3.4]oct-5-yl]-2-fluoro-N-methylbenzamide.

8 Claims, 9 Drawing Sheets

(56) References Cited

OTHER PUBLICATIONS

Lin et al., "Prostate-Specific Antigen-Based Screening for Prostate Cancer. An Evidence Update for the U.S. Preventive Services Task Force", Evidence Synthesis, No. 90, Agency for Healthcare Research and Quality, Oct. 2011, AHRQ Publication No. 12-05 160-EF-1, pp. 1-60.

Matsubara et al., "Phase 1 study of darolutamide (ODM-201): a new-generation androgen receptor antagonist, in Japanese patients with metastatic castration-resistant prostate cancer", Cancer Chemother Pharmacol, 2017, vol. 80, pp. 1063-1072.

Scher et al., "Design and End Points of Clinical Trials for Patients With Progressive Prostate Cancer and Castrate Levels of Testosterone: Recommendations of the Prostate Cancer Clinical Trials Working Group", J Clin Oncol., 2008, vol. 26, pp. 1148-1159.

Scher et al., "Flutamide Withdrawal Syndrome: Its Impact on Clinical Trials in Hormone-Refractory Prostate Cancer", Journal of Clinical Oncology, 1993, vol. 11, No. 8, pp. 1566-1572.

Schroder et al., "Screening for Prostate Cancer Decreases the Risk of Developing Metastatic Disease: Findings from the European Randomized Study of Screening for Prostate Cancer (ERSPC)", European Urology, 2012, vol. 62, No. 5, pp. 745-752.

Sweeney et al., "Chemohormonal Therapy in Metastatic Hormone-Sensitive Prostate Cancer", N. Engl. J. Med., 2015, vol. 373, pp. 737-746.

Tran et al., "Development of a Second-Generation Antiandrogen for Treatment of Advanced Prostate Cancer", 2009, vol. 324, No. 5928, pp. 787-790.

"Enzalutamide," National Center for Biotechnology Information (2023). PubChem Compound Summary for CID 15951529, Retrieved Mar. 24, 2023 from https://pubchem.ncbi.nlm.nih.gov/compound/Enzalutamide.

"FDA approves apalutamide for metastatic castration-sensitive prostate cancer," on Sep. 17, 2019. Available from: https://www.fda.gov/drugs/resources-information-approved-drugs/fda-approves-apalutamide-metastatic-castration-sensitive-prostate-cancer.

"FDA approves apalutamide for non-metastatic castration-resistant prostate cancer," on Feb. 14, 2018. Available from: https://www.fda.gov/drugs/resources-information-approved-drugs/fda-approves-apalutamide-non-metastatic-castration-resistant-prostate-cancer.

"FDA approves darolutamide for non-metastatic castration-resistant prostate cancer," on Jul. 30, 2019. Available from: https://www.fda.gov/drugs/resources-information-approved-drugs/fda-approves-darolutamide-non-metastatic-castration-resistant-prostate-cancer.

"FDA approves darolutamide tablets for metastatic hormone-sensitive prostate cancer," Aug. 5, 2022. Available from: https://www.fda.gov/drugs/resources-information-approved-drugs/fda-approves-darolutamide-tablets-metastatic-hormone-sensitive-prostate-cancer.

"FDA approves enzalutamide for castration-resistant prostate cancer," Jul. 13, 2018. Available from: https://www.fda.gov/drugs/resources-information-approved-drugs/fda-approves-enzalutamide-castration-resistant-prostate-cancer.

"FDA approves enzalutamide for metastatic castration-sensitive prostate cancer," on Dec. 16, 2019. Available from: https://www.fda.gov/drugs/resources-information-approved-drugs/fda-approves-enzalutamide-metastatic-castration-sensitive-prostate-cancer.

"Janssen Announces ERLEADA (apalutamide) Phase 3 TITAN Study unblinded as Dual Primary Endpoints Achieved in clinical Program Evaluating Treatment of Patients with Metastatic Castration-Sensitive Prostate Cancer," Johnson & Johnson, Jan. 30, 2019, pp. 1-5.

"Rezvilutamide," National Center for Biotechnology Information (2023). PubChem Compound Summary for CID 89995232, Retrieved Mar. 24, 2023 from https://pubchem.ncbi.nlm.nih.gov/compound/Rezvilutamide.

Abarca et al., "Safety, tolerability, pharmacokinetics, and immunogenicity of motavizumab, a humanized, enhanced-potency monoclonal antibody for the prevention of respiratory syncytial virus infection in at-risk children," Pediatr Infect Dis J, vol. 28, Issue 4, 2009, pp. 267-272.

Abbasi, A., et al., "Darolutamide as a Second-Generation Androgen Receptor Inhibitor in the Treatment of Prostate Cancer," Curr Mol Med, vol. 21, Issue 4, 2021, pp. 332-346.

Alfonzo, E., et al., "No. survival difference between robotic and open radical hysterectomy for women with early-stage cervical cancer: results from a nationwide population-based cohort study," Eur J Cancer, vol. 116, 2019, pp. 169-177.

Apalutamide—Patient Information—ERLEADA™ (apalutamide), Tablets. 2018, 2pp.

Aragon-Ching, J.B., "ARASENS: making sense out of first-line metastatic hormone-sensitive prostate cancer treatment," Asian J Androl, vol. 25, Issue 1, 2022, pp. 4.

Armstrong AJ. et al., "Final overall survival (OS) analysis from ARCHES: A phase III, randomized, double-blind, placebo (PBO)-controlled study of enzalutamide (ENZA) + androgen deprivation therapy (ADT) in men with metastatic hormone-sensitive prostate cancer (mHSPC)," Ann Oncol., vol. 32, 2021, (Suppl):S1300-S1301, Abstract LBA25.

Armstrong et al., "ARCHES: A Randomized, Phase III Study of Androgen Deprivation Therapy With Enzalutamide or Placebo in Men With Metastatic Hormone-Sensitive Prostate Cancer", J Clin Oncol, 2019, vol. 37, No. 32, pp. 2974-2986.

Armstrong, A.J., et al., "Efficacy of Enzalutamide plus Androgen Deprivation Therapy in Metastatic Hormone-Sensitive Prostate Cancer by Pattern of Metastatic Spread: ARCHES Post Hoc Analyses," J Urol, vol. 205, Issue 5, 2021, pp. 1361-1371.

Borgmann et al., "Moving Towards Precision Urologic Oncology: Targeting Enzalutamide-resistant Prostate Cancer and Mutated Forms of the Androgen Receptor Using the Novel Inhibitor Darolutamide (ODM-201), " Eur Urol, vol. 73, Issue 1, 2018, pp. 4-8.

Cattrini, C., et al., "Epidemiological Characteristics and Survival in Patients with De Novo Metastatic Prostate Cancer," Cancers (Basel), vol. 12, Issue 10, 2020, pp. 11.

Chen, Y., et al., "Second generation androgen receptor antagonists and challenges in prostate cancer treatment," Cell Death Dis, vol. 13, Issue 7, 632, 2022, pp. 11.

Chi, K.N., et al., "Apalutamide in Patients With Metastatic Castration-Sensitive Prostate Cancer: Final Survival Analysis of the Randomized, Double-Blind, Phase III TITAN Study," J Clin Oncol, vol. 39, Issue 20, 2021, pp. 2294-2303.

Chinese Society of Clinical Oncology Guidelines 2022: Diagnosis and Treatment of Prostate Cancer, Accessed Jun. 12, 2022, pp. 1-35.

Chowdhury, S., et al., "Deep, rapid, and durable prostate-specific antigen decline with apalutamide plus androgen deprivation therapy is associated with longer survival and improved clinical outcomes in TITAN patients with metastatic castration-sensitive prostate cancer," Ann Oncol, vol. 34, Issue 5, 2023, pp. 477-485.

Chung, D.Y., et al., "Novel Treatment Strategy Using Second-Generation Androgen Receptor Inhibitors for Non-Metastatic Castration-Resistant Prostate Cancer," Biomedicines, vol. 9, Issue 6, 2021, pp. 13.

Clinical pharmacology and biopharmaceutics review(s), NDA 20,3415 Review—Enzalutamide. 2012, 1-83.

Cornford et al., "EAU-EANM-ESTRO-ESUR-SIOG Guidelines on Prostate Cancer. Part II—2020 Update: Treatment of Relapsing and Metastatic Prostate Cancer," Eur Urol, vol. 79, Issue 2, 2021, pp. 263-282.

Crawford, E.D., et al., "Androgen Receptor Targeted Treatments of Prostate Cancer: 35 Years of Progress with Antiandrogens," J Urol, vol. 200, Issue 5, 2018, pp. 956-966.

Davis, I.D., et al., "Updated overall survival outcomes in Enzamet (ANZUP 1304), an international, cooperative group trial of enzalutamide in metastatic hormone-sensitive prostate cancer (mHSPC)," vol. 40, 2022, (17_suppl), pp. LBA5004-LBA5004.

Desai, M.M., et al., "Trends in Incidence of Metastatic Prostate Cancer in the US," JAMA Netw Open, vol. 5, Issue 3, e222246, 2022, pp. 12.

European Association of Urology 2023: EAU Clinical Guidelines. Retrieved Jul. 5, 2023 from http://uroweb.org/guideline/prostate-cancer/.

(56) References Cited

OTHER PUBLICATIONS

Fizazi et al., "Abiraterone plus prednisone added to androgen deprivation therapy and docetaxel in de novo metastatic castration-sensitive prostate cancer (PEACE-1): a multicentre, open-label, randomised, phase 3 study with a 2×2 factorial design," Lancet, vol. 399, Issue 10336, 2022, pp. 1695-1707.

Fizazi, K., et al., "Activity and safety of ODM-201 in patients with progressive metastatic castration-resistant prostate cancer (ARADES): an open-label phase 1 dose-escalation and randomised phase 2 dose expansion trial," Lancet Oncol, vol. 15, Issue 9, 2014, pp. 975-985.

Gillessen, S., et al., "Management of patients with advanced prostate cancer-metastatic and/or castration-resistant prostate cancer: Report of the Advanced Prostate Cancer Consensus Conference (APCCC) 2022," Eur J Cancer, vol. 185, 2023, pp. 178-215.

Gim, H.J., et al., "Conformational dynamics of androgen receptors bound to agonists and antagonists," Sci Rep, vol. 11, Issue 1, 15887, 2021, pp. 15.

Gottlieb, B., et al., "The androgen receptor gene mutations database: 2012 update," Hum Mutat, vol. 33, Issue 5, 2012, pp. 887-894.

Gu, W., et al., "Rezvilutamide versus bicalutamide in combination with androgen-deprivation therapy in patients with high-volume, metastatic, hormone-sensitive prostate cancer (CHART): a randomised, open-label, phase 3 trial," Lancet Oncol, vol. 23, Issue 10, 2022, pp. 1249-1260.

Higano, C.S., et al., "Long-term Safety and Antitumor Activity in the Phase 1-2 Study of Enzalutamide in Pre- and Post-docetaxel Castration-Resistant Prostate Cancer," Eur Urol, vol. 68, Issue 5, 2015, pp. 795-801.

Hussain, M., et al., "Darolutamide Plus Androgen-Deprivation Therapy and Docetaxel in Metastatic Hormone-Sensitive Prostate Cancer by Disease Volume and Risk Subgroups in the Phase III ARASENS Trial," J Clin Oncol, vol. 41, Issue 20, 2023, pp. 3595-3607.

Jin et al., "Communication between the Ligand-Binding Pocket and the Activation Function-2 Domain of Androgen Receptor Revealed by Molecular Dynamics Simulations," J Chem Inf Model, vol. 59, Issue 2, 2019, pp. 842-857.

Keam, S.J., "Rezvilutamide: First Approval," Drugs, vol. 83, Issue 2, 2023, pp. 189-193.

Kim et al., "Pharmacokinetics of enzalutamide, an anti-prostate cancer drug, in rats," Arch Pharm Res, vol. 38, Issue 11, 2015, pp. 2076-2082.

Kolvenbag, G.J., et al., "Receptor affinity and potency of nonsteroidal antiandrogens: translation of preclinical findings into clinical activity," Prostate Cancer Prostatic Dis, vol. 1, Issue 6, 1998, pp. 307-314.

Kumar, N., "ARASENS Trial: Should darolutamide now be added to androgen-deprivation therapy and docetaxel in patients with metastatic, hormone-sensitive prostate cancer?," Indian J Urol, vol. 38, Issue 3, 2022, pp. 238-239.

Lee et al., "Comparative pharmacokinetic evaluation of two formulations of bicalutamide 50-mg tablets: an open-label, randomized-sequence, single-dose, two-period crossover study in healthy Korean male volunteers," Clin Ther, vol. 31, Issue 2, 2009, pp. 3000-3008.

Lin et al., "Risk factors for progression to castration-resistant prostate cancer in metastatic prostate cancer patients", J Cancer, 2019, vol. 10, No. 22, pp. 5608-5613.

Liu et al., "Molecular mechanism of R-bicalutamide switching from androgen receptor antagonist to agonist induced by amino acid mutations using molecular dynamics simulations and free energy calculation," J Comput Aided Mol Des, vol. 30, Issue 12, 2016, pp. 1189-1200.

Lowrance, W., et al., "Updates to Advanced Prostate Cancer: AUA/SUO Guideline (2023)," J Urol, vol. 209, Issue 6, 2023, pp. 1082-1090.

Massard, C., et al., "Pharmacokinetics, Antitumor Activity, and Safety of ODM-201 in Patients with Chemotherapy-naive Metastatic Castration-resistant Prostate Cancer: An Open-label Phase 1 Study," Eur Urol, vol. 69, Issue 5, 2016, pp. 834-840.

McKillop et al., "Metabolism and enantioselective pharmacokinetics of Casodex in man," Xenobiotica, vol. 23, Issue 11, 1993, pp. 1241-1253.

Mehtälä, J., et al., "Overall survival and second primary malignancies in men with metastatic prostate cancer," PLoS One, vol. 15, Issue 2, e0227552, 2020, pp. 12.

Nadal, M., et al., "Structure of the homodimeric androgen receptor ligand-binding domain," Nat Commun, vol. 8, 14388, 2017, pp. 14.

National Medical Products Administration conditionally approves Rezvilutamide for metastatic hormone-sensitive prostate cancer with high-volume disease on Jun. 29, 2022. Available from: https://www.nmpa.gov.cn/yaowen/ypjgyw/20220629092644102.html.

O'Brien et al., "Efficacy of motavizumab for the prevention of respiratory syncytial virus disease in healthy Native American infants: a phase 3 randomised double-blind placebo-controlled trial", Lancet Infect Dis, 2015, vol. 15, No. 12, pp. 1398-1408.

Özturan, D., et al., "Androgen Receptor-Mediated Transcription in Prostate Cancer," Cells, vol. 11, Issue 5, 2022, pp. 19.

Qin et al., "Activity and safety of SHR3680, a novel antiandrogen, in patients with metastatic castration-resistant prostate cancer: a phase I/II trial", BMC Med, 2022, vol. 20, No. 84, pp. 1-10.

Qin et al., "SHR3680, a novel antiandrogen, for the treatment of metastatic castration-resistant prostate cancer (mCRPC): A phase I/II study", Journal of Clinical Oncology, 2020, vol. 38, pp. 90-90.

Rathkopf et al., "Phase I study of ARN-509, a novel antiandrogen, in the treatment of castration-resistant prostate cancer", J Clin Oncol, 2013, vol. 31, No. 28, pp. 3525-3530.

Rathkopf et al., "Safety and Antitumor Activity of Apalutamide (ARN-509) in Metastatic Castration-Resistant Prostate Cancer with and without Prior Abiraterone Acetate and Prednisone", Clin Cancer Res, 2017, vol. 23, No. 14, pp. 3544-3551.

Riaz et al., "First-line Systemic Treatment Options for Metastatic Castration-Sensitive Prostate Cancer: A Living Systematic Review and Network Meta-analysis", JAMA Oncol, 2023, vol. 9, No. 5, pp. 635-645.

Roy et al., "Addition of Docetaxel to Androgen Receptor Axis-targeted Therapy and Androgen Deprivation Therapy in Metastatic Hormone-sensitive Prostate Cancer: A Network Meta-analysis", Eur Urol Oncol, 2022, vol. 5, No. 5, pp. 494-502.

Saad et al., "Association of prostate-specific antigen (PSA) response and overall survival (OS) in patients with metastatic hormone-sensitive prostate cancer (mHSPC) from the phase 3 ARASENS trial", Journal of Clinical Oncology, 2022, vol. 40, suppl. 16, pp. 5078-5078.

Schaeffer et al., "NCCN Guidelines® Insights", Prostate Cancer, Version 1.2023. J Natl Compr Canc Netw, 2022, vol. 20, Issue 12, pp. 1288-1298.

Scher et al., "Antitumour activity of MDV3100 in castration-resistant prostate cancer: a phase 1-2 study", Lancet, 2010, vol. 375, No. 9724, pp. 1437-1446.

Scher et al., "Prevalence of Prostate Cancer Clinical States and Mortality in the United States: Estimates Using a Dynamic Progression Model", PLoS One, 2015, vol. 10, No. 10, pp. 1-12.

Shore et al., "Safety and Antitumour Activity of ODM-201 (BAY-1841788) in Chemotherapy-naïve and CYP17 Inhibitor-naïve Patients: Follow-up from the ARADES and ARAFOR Trials", Eur Urol Focus, 2018, vol. 4, No. 4, pp. 547-553.

Smith et al., "Darolutamide and Survival in Metastatic, Hormone-Sensitive Prostate Cancer", N Engl J Med, 2022, vol. 386, No. 12, pp. 1132-1142.

Sugawara et al., "Darolutamide is a potent androgen receptor antagonist with strong efficacy in prostate cancer models", Int J Cancer, 2019, vol. 145, No. 5, pp. 1382-1394.

Sung et al., "Global Cancer Statistics 2020: GLOBOCAN Estimates of Incidence and Mortality Worldwide for 36 Cancers in 185 Countries", CA Cancer J Clin, 2021, vol. 71, No. 3, pp. 209-249.

Tan et al., "Androgen receptor: structure, role in prostate cancer and drug discovery", Acta Pharmacol Sin, 2015, vol. 36, No. 1, pp. 3-23.

Virgo et al., "Initial Management of Noncastrate Advanced, Recurrent, or Metastatic Prostate Cancer: ASCO Guideline Update", J Clin Oncol, 2021, vol. 39, No. 11, pp. 1274-1305.

(56) References Cited

OTHER PUBLICATIONS

Virgo et al., "Initial Management of Noncastrate Advanced, Recurrent, or Metastatic Prostate Cancer: ASCO Guideline Update", J Clin Oncol, 2023: pp. 1-35.
Westaby et al., "A New Old Target: Androgen Receptor Signaling and Advanced Prostate Cancer", Annu Rev Pharmacol Toxicol, 2022, vol. 62, pp. 131-153.
Zurth et al., "Clinical Pharmacokinetics of the Androgen Receptor Inhibitor Darolutamide in Healthy Subjects and Patients with Hepatic or Renal Impairment", Clin Pharmacokinet, 2022, vol. 61, No. 4, pp. 565-575.
Zurth et al., "Higher blood-brain barrier penetration of [14C]apalutamide and [14C]enzalutamide compared to [14C]darolutamide in rats using whole-body autoradiography", Journal of Clinical Oncology, 2019, vol. 37, No. 7_suppl, pp. 156-156.
Zurth, C., et al., Blood-brain barrier penetration of [14C]darolutamide compared with [14C]enzalutamide in rats using whole body autoradiography. 2018. 36(6_suppl): p. 345-345.
Highlights of Prescribing Information, Label, CASODEX® (Bicalutamide) Tablets, 2010, 1-24.
Prescribing Information for Rezvilutamide Tablets, Label, Tradename ARIANE® (Rezvilutamide) Tablets, 2022, 13 pages (with translation).
"FDA Approves First Treatment for Nonmetastatic Castration-Resistantp Rostate Cancer," AJN The American Journal of Nursing, vol. 118, No. 6, 2018, p. 26.
Chi. et al., "Genitourinary tumors, prostate," Annals of Oncology, 2016, vol. 27, Supplement 6, Abstract No.771TiP, p. 1.

US 11,963,952 B2

ANTI-ANDROGENS FOR THE TREATMENT OF METASTATIC CASTRATION-SENSITIVE PROSTATE CANCER

CROSS REFERENCE TO RELATED APPLICATIONS

This application a continuation of U.S. patent application Ser. No. 17/425,865, filed Jul. 26, 2021, which is the National Stage Application of International Patent Application No. PCT/IB2020/050752, filed Jan. 30, 2020, which claims the benefit of U.S. provisional patent application No. 62/901,694, filed on Sep. 17, 2019; U.S. provisional patent application No. 62/836,920, filed Apr. 22, 2019; U.S. provisional patent application No. 62/833,371, filed Apr. 12, 2019; U.S. provisional patent application No. 62/822,312, filed on Mar. 22, 2019; U.S. provisional patent application No. 62/803,096, filed Feb. 8, 2019; and U.S. provisional application No. 62/798,836, filed on Jan. 30, 2019; all of which are incorporated by reference herein.

TECHNICAL FIELD

Disclosed herein are methods of treating metastatic castration-sensitive prostate cancer with anti-androgens, including but not limited to, 4-[7-(6-cyano-5-trifluoromethylpyridin-3-yl)-8-oxo-6-thioxo-5,7-diazaspiro[3.4]oct-5-yl]-2-fluoro-N-methylbenzamide.

BACKGROUND

Prostate cancer is the second most frequently diagnosed cancer and the sixth leading cause of cancer death in males, accounting for 14%(903,500) of the total new cancer cases and 6% (258,400) of the total cancer deaths in males worldwide. The course of prostate cancer from diagnosis to death is best categorized as a series of clinical stages based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate stage. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal stage of the disease.

Based on current guidelines, androgen deprivation therapy (ADT) with or without docetaxel is considered the appropriate active control therapy for the patients with metastatic hormone-sensitive prostate cancer. However, there is a clear unmet medical need for alternative treatment options in mCSPC. Treatments that can delay disease progression and associated morbidities would be of significant clinical benefit in this patient population. The disclosed methods are directed to these and other important needs.

SUMMARY

Described herein are methods of treating metastatic castration-sensitive prostate cancer in a male human comprising, consisting of, or consisting essentially of administering a therapeutically effective amount of an anti-androgen to a male human with metastatic castration-sensitive prostate cancer. In these methods, the anti-androgen can be: 4-[7-(6-cyano-S-trifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide or N-{(2S)-1-[3-(3-chloro-4-cyanophenyl)-1H-pyrazol-1-yl]propan-2-yl}-5-(1-hydroxyethyl)-1H-pyrazole-3-carboxamide. In some embodiments, administration of the anti-androgen provides an increase in overall survival of the male human relative to the overall survival rate of a comparative population of male humans with the metastatic castration-sensitive prostate cancer, said comparative population having been administered a placebo in combination with an androgen deprivation therapy. In other embodiments, the comparative population is untreated. In further embodiments, administration of the anti-androgen provides an increase in progression-free survival of the male human relative to the progression-free survival rate of a comparative population of male humans with the metastatic castration-sensitive prostate cancer, said comparative population having been administered a placebo in combination with an androgen deprivation therapy. In other embodiments, the comparative population is untreated.

In some embodiments, the male human has received at least one prior therapy for the treatment of cancer prior to the administration of the anti-androgen, wherein the prior therapy for the treatment of cancer is radiation, surgical intervention or docetaxel therapy. In some embodiments, the male human is treatment naïve.

In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In further embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered daily to the male human. In still further embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human. In some embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human on a continuous daily dosing schedule. In further embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human at a dose of about 30 mg per day to about 480 mg per day. In still further embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human at a dose of about 180 mg per day to about 480 mg per day. In certain embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human at a dose of: (a) about 30 mg per day; (b) about 60 mg per day; (c) about 90 mg per day; (d) about 120 mg per day; or (d) about 240 mg per day. In some embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered orally to the male human at a dose of about 240 mg per day. In some embodiments, the dose of the antiandrogen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide specifically is decreased to 180 mg per day or 120 mg per day if the male human experiences a greater than or equal to Grade 3 toxicity.

In certain embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide specifically is not co-administered with: (a) a medication that is a strong CYP2C8 or CYP3A4 inhibitor; (b) a medication that is primarily metabolized by CYP3A4, CYP2C19, or CYP2C9; (c) a medication that is a substrate of UDP-glucuronosyl transferase (UGT); or (d) a medication that is a substrate of P-glycoprotein (P-gp), breast cancer resistance protein (BCRP) or organic anion transporting polypeptide 1B1 (OATP1B1).

In some embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered in combination with androgen deprivation therapy. In further embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is administered in combination with at least one gonadotropin-releasing hormone (GnRH) agonist or antagonist. In still further embodiments, the at least one GnRH agonist or antagonist is or comprises leuprolide, buserelin, naferelin, histrelin, goserelin, deslorelin, degarelix, ozarelix, ABT-620 (elagolix), TAK-385 (relugolix), EP-100, KLH-2109 or triptorelin. In certain embodiments, the anti-androgen generally and 4-[7-(6-cyano-5-trifluoromethylpyridin-3-yl)-8-oxo-6-thioxo-5,7-diazaspiro[3.4]oct-5-yl]-2-fluoro-N-methylbenzamide more specifically is used in combination with bilateral orchiectomy.

In some embodiments, the anti-androgen is 4-(3-(4-cyano-3-(trifluoromethyl)phenyl)-5,5-dimethyl-4-oxo-2-thioxoimidazolidin-1-yl)-2-fluoro-N-methylbenzamide. In further embodiments, the 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human at a dose of about 160 mg per day.

In some embodiments, the anti-androgen is 4-[7-[4-cyano-3-(trifluoromethyl)phenyl]-8-oxo-6-thioxo-5,7-diazaspiro[3.4]oct-5-yl]-2-fluoro-N-methylbenzamide.

In some embodiments, the anti-androgen is N-{(2S)-1-[3-(3-chloro-4-cyanophenyl)-1H-pyrazol-1-yl]propan-2-yl}-5-(1-hydroxyethyl)-1H-pyrazole-3-carboxamide (darolutamide). In further embodiments, N-{(2S)-1-[3-(3-chloro-4-cyanophenyl)-1H-pyrazol-1-yl]propan-2-yl}-5-(1-hydroxyethyl)-1H-pyrazole-3-carboxamide is administered orally to the male human at a dose of 600 mg twice daily. In further embodiments, N-{(2S)-1-[3-(3-chloro-4-cyanophenyl)-1H-pyrazol-1-yl]propan-2-yl}-5-(1-hydroxyethyl)-1H-pyrazole-3-carboxamide is administered orally to the male human at a dose of 600 mg twice daily with food.

Also disclosed herein are methods for treating metastatic castration-sensitive prostate cancer in a male human consisting or consisting essentially of administering a therapeutically effective amount of an anti-androgen to a male human with metastatic castration-sensitive prostate cancer, wherein the anti-androgen is one or more of: 4-[7-(6-cyano-5-trifluoromethylpyridintrifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide or N-{(2S)-1-[3-(3-chloro-4-cyanophenyl)-1H-pyrazol-1-yl]propan-2-yl}-5-(1-hydroxyethyl)-1H-pyrazole-3-carboxamide.

Also disclosed herein are methods of treating metastatic castration-sensitive prostate cancer in a male human, comprising: (a) determining whether the male human has metastatic castration-sensitive prostate cancer; and (b) administering an anti-androgen to a male human in a therapeutically effective amount to treat the metastatic castration-sensitive prostate cancer, wherein the anti-androgen is: 4-[7-(6-cyano-5-trifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide, or N-{(2S)-1-[3-(3-chloro-4-cyanophenyl)-1H-pyrazol-1-¬yl]propan-2-yl}-5-(1-hydroxyethyl)-1H-pyrazole-3-carboxamide.

Also disclosed herein are methods of treating metastatic castration-sensitive prostate cancer comprising administering an approved drug product comprising apalutamide to a male human with metastatic castration-sensitive prostate cancer in an amount that is described in a drug product label for said drug product. In some embodiments, the approved drug product comprising apalutamide is an ANDA drug product, a supplemental New Drug Application drug product or a 505(b)(2) drug product. In some embodiments, the method is clinically proven safe and/or effective.

Also disclosed herein are pharmaceutical products comprising a clinically proven safe and clinically proven effective amount of apalutamide, wherein the pharmaceutical product is packaged and wherein the package includes a label that (a) identifies apalutamide as a regulatory approved chemical entity, and (b) instructs use of apalutamide in the treatment of castration-sensitive prostate cancer.

Also disclosed herein are methods of selling an approved drug product comprising apalutamide, said method comprising selling such drug product, wherein a drug product label for a reference listed drug for such drug product includes instructions for treating castration-sensitive prostate cancer. Further disclosed herein are methods of offering for sale an approved drug product comprising apalutamide, said method comprising offering for sale such drug product, wherein a drug product label for a reference listed drug for such drug product includes instructions for treating castration-sensitive prostate cancer. In some embodiments, the drug product is an ANDA drug product, a supplemental New Drug Application drug product or a 505(b)(2) drug product.

BRIEF DESCRIPTION OF THE DRAWINGS

The summary, as well as the following detailed description, is further understood when read in conjunction with the appended drawings. For the purpose of illustrating the disclosed methods, the drawings show exemplary embodiments of the methods; however, the methods are not limited to the specific embodiments disclosed. In the drawings.

DETAILED DESCRIPTION OF ILLUSTRATIVE EMBODIMENTS

Figure 1:
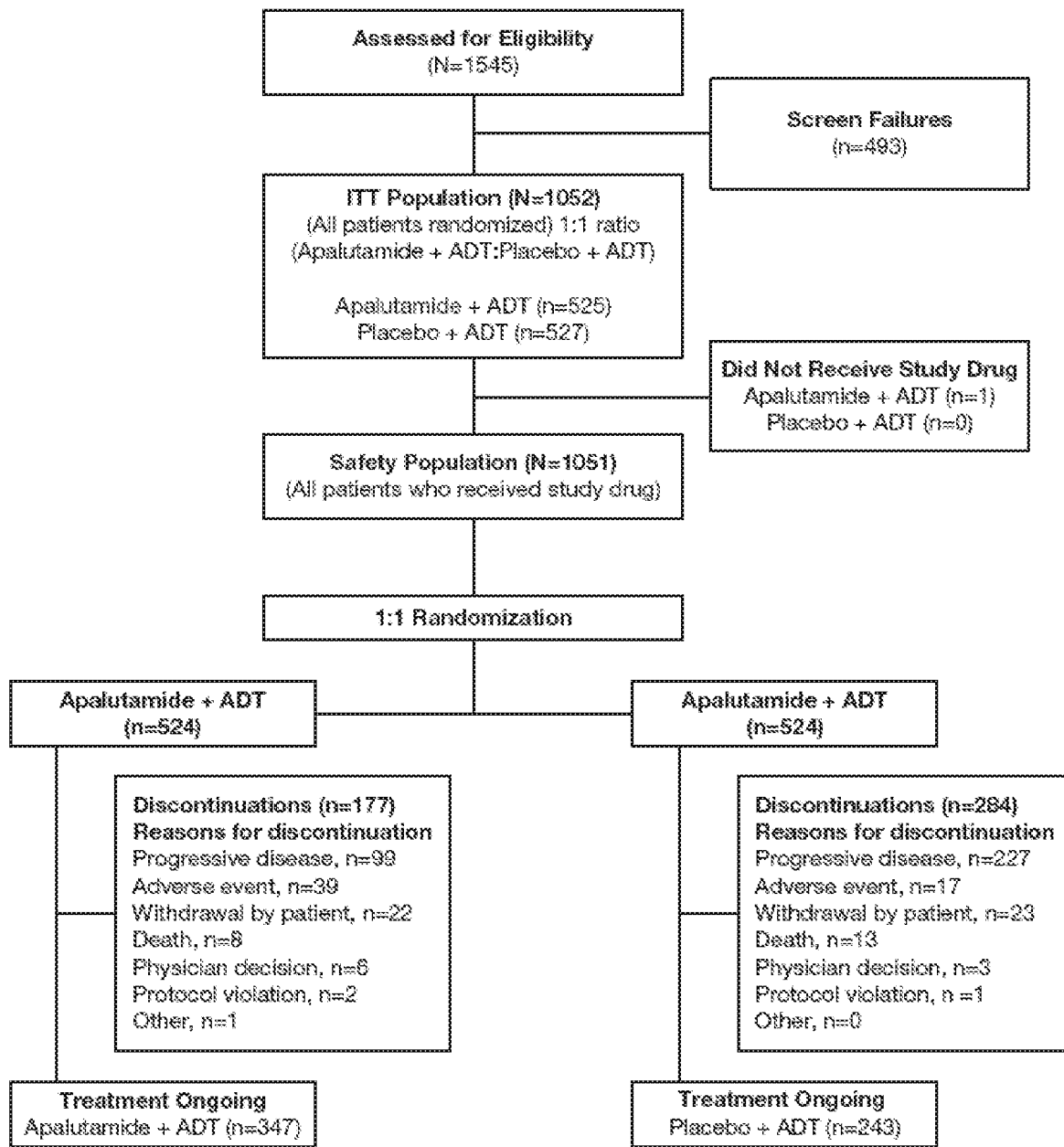
FIG. 1 is a schematic of the apalutamide phase ill clinical trial study design. ADT androgen deprivation therapy.

It is to be appreciated that certain features of the invention which are, for clarity, described herein in the context of separate embodiments may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, although an embodiment may be described as part of a series of steps or part of a more general structure, each said step may also be considered an independent embodiment in itself, combinable with others.

The transitional terms "comprising," "consisting essentially of," and "consisting" are intended to connote their generally in accepted meanings in the patent vernacular, that is, (i) "comprising," which is synonymous with "including," "containing," or "characterized by," is inclusive or open-ended and does not exclude additional, unrecited elements or method steps; (ii) "consisting of excludes any element, step, or ingredient not specified in the claim; and (iii) "consisting essentially of limits the scope of a claim to the specified materials or steps "and those that do not materially affect the basic and novel characteristic(s)" of the claimed invention. More specifically, the basic and novel characteristics relates to the ability of the method to provide at least one of the benefits described herein, including but not limited to the ability to improve the survivability of the male human population relative to the survivability of the comparative male human population described elsewhere herein.

Embodiments described in terms of the phrase "comprising" (or its equivalents), also provide, as embodiments, those which are independently described in terms of "consisting of and "consisting essentially of."

When a value is expressed as an approximation by use of the descriptor "about," it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

If not otherwise specified, the term "about" signifies a variance of ±10% of the associated value, but additional embodiments include those where the variance may be ±5%, ±15%, ±20%, ±25%, or ±50%.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

The present invention may be understood more readily by reference to the following description taken in connection with the accompanying Drawing and Examples, all of which form a part of this disclosure. It is to be understood that this invention is not limited to the specific products, methods, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognized that the descriptions refer to various compounds, compositions and methods of using said compounds and compositions. That is, where the disclosure describes or claims a feature or embodiment associated with a composition or a method of using a composition, it is appreciated that such a description or claim is intended to extend these features or embodiment to embodiments in each of these contexts (i.e., compositions and methods of using).

Androgen receptor (AR) is a member of the steroid and nuclear receptor superfamily. Among this large family of proteins, only five vertebrate steroid receptors are known and include the androgen receptor, estrogen receptor, progesterone receptor, glucocorticoid receptor, and mineralocorticoid receptor. AR is a soluble protein that functions as an intracellular transcriptional factor. AR function is regulated by the binding of androgens, which initiates sequential conformational changes of the receptor that affect receptor-protein interactions and receptor-DNA interactions.

AR is mainly expressed in androgen target tissues, such as the prostate, skeletal muscle, liver, and central nervous system (CNS), with the highest expression level observed in the prostate, adrenal gland, and epididymis. AR can be activated by the binding of endogenous androgens, including testosterone and 5-dihydrotestosterone (5a-DHT).

The androgen receptor (AR), located on Xql 1-12, is a 110 kD nuclear receptor that, upon activation by androgens, mediates transcription of target genes that modulate growth and differentiation of prostate epithelial cells. Similar to the other steroid receptors, unbound AR is mainly located in the cytoplasm and associated with a complex of heat shock proteins (HSPs) through interactions with the ligand-binding domain. Upon agonist binding, AR goes through a series of conformational changes: the heat shock proteins dissociate from AR, and the transformed AR undergoes dimerization, phosphorylation, and translocation to the nucleus, which is mediated by the nuclear localization signal. Translocated receptor then binds to the androgen response element (ARE), which is characterized by the six-nucleotide half-site consensus sequence 5'-TGTTCT-3' spaced by three random nucleotides and is located in the promoter or enhancer region of AR gene targets. Recruitment of other transcription co-regulators (including co-activators and co-repressors) and transcriptional machinery further ensures the transactivation of AR-regulated gene expression. All of these processes are initiated by the ligand-induced conformational changes in the ligand-binding domain.

AR signaling is crucial for the development and maintenance of male reproductive organs including the prostate gland, as genetic males harboring loss of function AR mutations and mice engineered with AR defects do not develop prostates or prostate cancer. This dependence of prostate cells on AR signaling continues even upon neoplastic transformation. Androgen depletion (such as using GnRH agonists) continues to be the mainstay of prostate cancer treatment. However, androgen depletion is usually effective for a limited duration and prostate cancer evolves to regain the ability to grow despite low levels of circulating androgens.

Castration resistant prostate cancer (CRPC) is a lethal phenotype and almost all of patients will die from prostate cancer. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites. Given that prostate cancer cells depend on androgen receptor (AR) for their proliferation and survival, these men are treated with agents that block production of testosterone (e.g., GnRH agonists), alone or in combination with anti-androgens (e.g., bicalutamide), which antagonize the effect of any residual testosterone on AR. The approach is effective as evidenced by a drop in PSA and regression of visible tumor (if present) in some patients; however, this is followed by regrowth as a castration resistant prostate cancer (CRPC) to which most patients eventually succumb. Recent studies on the molecular basis of CRPC have demonstrated that CRPC continues to depend on AR signaling and that a key mechanism of acquired resistance is an elevated level of AR protein (Nat. Med, 2004, 10, 33-39). AR targeting agents with activity in castration sensitive and castration resistant prostate cancer have great promise in treating this lethal disease.

The course of prostate cancer from diagnosis to death is best categorized as a series of clinical states based on the extent of disease, hormonal status, and absence or presence of detectable metastases: localized disease, rising levels of prostate-specific antigen (PSA) after radiation therapy or surgery with no detectable metastases, and clinical metastases in the non-castrate or castrate state. Although surgery, radiation, or a combination of both can be curative for patients with localized disease, a significant proportion of these patients have recurrent disease as evidenced by a rising level of PSA, which can lead to the development of metastases, especially in the high-risk group—a transition to the lethal phenotype of the disease.

Androgen depletion is the standard treatment with a generally predictable outcome: decline in PSA, a period of stability in which the tumor does not proliferate, followed by rising PSA and regrowth as castration-resistant disease. Molecular profiling studies of castration-resistance prostate cancers commonly show increased androgen receptor (AR) expression, which can occur through AR gene amplification or other mechanisms.

Anti-androgens are useful for the treatment of prostate cancer during its early stages. However, prostate cancer often advances to a 'hormone-refractory' state in which the disease progresses in the presence of continued androgen ablation or anti-androgen therapy. Instances of antiandrogen withdrawal syndrome have also been reported after prolonged treatment with anti-androgens. Antiandrogen withdrawal syndrome is commonly observed clinically and is defined in terms of the tumor regression or symptomatic relief observed upon cessation of antiandrogen therapy. AR mutations that result in receptor promiscuity and the ability of these anti-androgens to exhibit agonist activity might at least partially account for this phenomenon. For example, hydroxyflutamide and bicalutamide act as AR agonists in T877A and W741L/W741C AR mutants, respectively.

In the setting of prostate cancer cells that were rendered castration resistant via overexpression of AR, it has been demonstrated that certain anti-androgen compounds, such as bicalutamide, have a mixed antagonist/agonist profile (Science, 2009 May 8; 324(5928): 787-90). This agonist activity helps to explain a clinical observation, called the anti-androgen withdrawal syndrome, whereby about 30% of men who progress on AR antagonists experience a decrease in serum PSA when therapy is discontinued (J Clin. Oncol, 1993, 11(8): p. 1566-72).

Prostate Cancer Stages

In the early stages of prostate cancer, the cancer is localized to the prostate. In these early stages, treatment typically involves either surgical removal of the prostate or radiation therapy to the prostate or observation only with no active intervention therapy in some patients. In the early stages where the prostate cancer is localized and requires intervention, surgery or radiation therapy are curative by eradicating the cancerous cells. About 30% of the time these procedures fail, and the prostate cancer continues to progress, as typically evidenced by a rising PSA level. Men whose prostate cancer has progressed following these early treatment strategies are said to have advanced or recurrent prostate cancer.

Because prostate cancer cells depend on the androgen receptor (AR) for their proliferation and survival, men with advanced prostate cancer am treated with agents that block the production of testosterone (e.g., GnRH agonists), alone or in combination with anti-androgens (e.g., bicalutamide), which antagonize the effect of any residual testosterone on AR. These treatments reduce serum testosterone to castrate levels, which generally slows disease progression for a period of time. The approach is effective as evidenced by a drop in PSA and the regression of visible tumors in some patients. Eventually, however, this is followed by regrowth referred to as castration-resistant prostate cancer (CRPC), to which most patients eventually succumb. Castration-resistant prostate cancer (CRPC) is categorized as non-metastatic or metastatic, depending on whether or not the prostate cancer has metastasized to other parts of the body.

Estimates from European country-specific registries indicate that approximately 15% to 30% of men diagnosed with prostate cancer had metastatic (M1) castration-sensitive prostate cancer (mCSPC). See, e.g. Flamand V, et al., *Prog Urol.* 2008:18:53-59. In the US, patients presenting with mCSPC account for approximately 4% of all prostate cancer diagnosis. Cetin K, et al. *Urology* 2010; 75:1396-1405. This disparity may result from differences in the use of PSA screening in different geographies. Schröder FH, e al., *Eur Urol.* 2012; 62:745-752. However, the percentage of men in the US who present with mCSPC may increase because there now appears to be a decrease in PSA screening after the United States Preventive Services Task Force (USPSTF) released its recommendation against PSA screening in 2012. Drazer M W, et al., *J Clin. Oncol* 2015; 33:2416 2423; Lin K, et al. Agency for Healthcare Research and Quality, 2011; No. 12-05160-3F-1.

Given that prostate cancer cells depend on AR signaling for their proliferation and survival, the standard treatment for patients with mCSPC disease is androgen deprivation therapy (ADT). Androgen deprivation therapy is defined as medical castration (i.e., gonadotropin releasing hormone analog [GnRHa; agonist or antagonist]) or surgical castration (i.e., bilateral orchiectomy). To prevent tumor flare in subjects with overt metastases, a short period of treatment with first generation anti-androgen may be used to reduce the flare in testosterone with initiation of a GnRH agonist.

Anti-Androgens

As used herein, the term "anti-androgen" carries its generally accepted meaning and may refer to a group of hormone receptor antagonist compounds that are capable of preventing or inhibiting the biologic effects of androgens on normally responsive tissues in the body. In some embodiments, an anti-androgen is a small molecule. In some embodiments, an anti-androgen is an AR antagonist. In some embodiments, an anti-androgen is an AR full antagonist. In some embodiments, an anti-androgen is a first-generation anti-androgen. In some embodiments, an anti-androgen is a second-generation anti-androgen.

As used herein, the term "AR antagonist" or "AR inhibitor" are used interchangeably herein and refer to an agent that inhibits or reduces at least one activity of an AR polypeptide. Exemplary AR activities include, but are not limited to, co-activator binding, DNA binding, ligand binding, or nuclear translocation.

As used herein, a "full antagonist" refers to an antagonist, which, at an effective concentration, essentially completely inhibits an activity of an AR polypeptide. As used herein, a "partial antagonist" refers an antagonist that is capable of partially inhibiting an activity of an AR polypeptide, but that, even at a highest concentration is not a full antagonist. By 'essentially completely' is meant at least about 80%, at least about 90%, at least about 95%, at least about 96%, at least about 97%, at least about 98% at least about 99%, or greater inhibition of the activity of an AR polypeptide.

As used herein, the term "first-generation anti-androgen" refers to an agent that exhibits antagonist activity against a wild-type AR polypeptide. However, first-generation anti-androgens differ from second-generation anti-androgens in that first-generation anti-androgens can potentially act as agonists in castration resistant prostate cancers (CRPC). Exemplary first-generation anti-androgens include, but are not limited to, flutamide, nilutamide and bicalutamide.

As used herein, the term "second-generation anti-androgen" refers to an agent that exhibits full antagonist activity against a wild-type AR polypeptide. Second-generation anti-androgens differ from first-generation anti-androgens in that second-generation anti-androgens act as full antagonists in cells expressing elevated levels of AR, such as for example, in castration resistant prostate cancers (CRPC). Exemplary second-generation anti-androgens include 4-[7-(6-cyano-5-trifluoromethylpyridin-3-yl)-8-oxo-6-thioxo-5,7-diazaspiro [3.4]oct-5-yl]-2-fluoro-N-methylbenzamide (also known as apalutamide, ARN-509, or JNJ-56021927; CAS No. 956104-40-8); 4-(3-(4-cyano-3-(trifluoromethyl)phenyl)-5, 5-dimethyl-4-oxo-2-thioxoimidazolidin-1-yl)-2-fluoro-N-methylbenzamide (also known as MDV3100 or enzalutamide; CAS No: 915087-33-1), 4-[7-(4-cyano-3-trifluoromethylphenyl)-8-oxo-6-thioxo-5,7-diazaspiro[3.4] oct-5-yl]-2-fluoro-N-methylbenzamide (RD162; CAS No. 915087-27-3) and N-{(2S)-1-[3-(3-chloro-4-cyanophenyl)-1H-pyrazol-1-yl]propan-2-yl}-5-(1-hydroxyethyl)-1H-pyrazole-3-carboxamide (also known as darolutamide). In some embodiments, a second-generation anti-androgen binds to an AR polypeptide at or near the ligand binding site of the AR polypeptide.

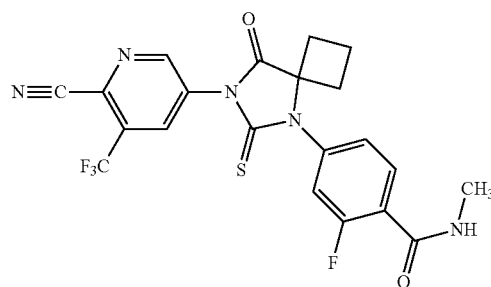 [SMILES: CNC(=O)c1ccc(N2C(=S)N(c3cnc(C#N)c(C(F)(F)F)c3)C(=O)C23CCC3)cc1F]

4-[7-(6-cyano-5-trifluoromethylpyridin-3-yl)-8-oxo-6-thioxo-5,7-diazaspiro[3.4]oct-5-yl]-2-fluoro-N-methylbenzamide (apalutamide)

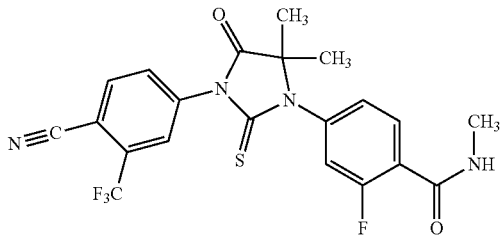 [SMILES: CNC(=O)c1ccc(N2C(=S)N(c3ccc(C#N)c(C(F)(F)F)c3)C(=O)C2(C)C)cc1F]

4-(3-(4-cyano-3-(trifluoromethyl)phenyl)-5,5-dimethyl-4-oxo-2-thioxoimidazolidin-1-yl)-2-fluoro-N-methylbenzamide (enzalutamide)

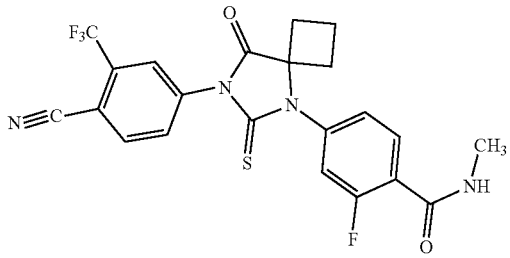 [SMILES: CNC(=O)c1ccc(N2C(=S)N(c3ccc(C#N)c(C(F)(F)F)c3)C(=O)C23CCC3)cc1F]

4-[7-(4-cyano-3-trifluoromethylphenyl)-8-oxo-6-thioxo-5,7-diazaspiro[3.4]oct-5-yl]-2-fluoro-N-methylbenzamide (RD162)

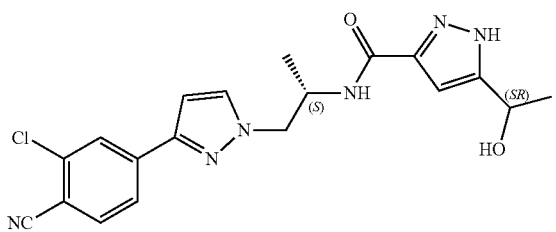

N-{(2S)-1-[3-(3-chloro-4-cyanophenyl)-1H-pyrazol-1-yl]propan-2-yl}-5-(1-hydroxyethyl)-1H-pyrazole-3-carboxamide (darolutamide) In some embodiments, an anti-androgen contemplated in the methods described herein inhibits AR nuclear translocation, such as darolutamide, DNA binding to androgen response elements, and coactivator recruitment. In some embodiments, an anti-androgen contemplated in the methods described herein exhibits no agonist activity in AR-overexpressing prostate cancer cells.

Apalutamide is a second-generation anti-androgen that binds directly to the ligand-binding domain of AR, impairing nuclear translocation, AR binding to DNA and AR target gene modulation, thereby inhibiting tumor growth and promoting apoptosis. Apalutamide binds AR with greater affinity than bicalutamide and induces partial or complete tumor regression in non-castrate hormone-sensitive and bicalutamide-resistant human prostate cancer xenograft models (Clegg et al. Cancer Res. Mar. 15, 2012 72; 1494). Apalutamide lacks the partial agonist activity seen with bicalutamide in the context of AR overexpression.

Darolutamide, BAY1841788 or ODM-201, is an AR antagonist that includes two diastereomers—ORM-16497 and ORM-16555. The chemical name is N-{(2S)-1-[3-(3-chloro-4-cyanophenyl)-1H-pyrazol-1-yl]propan-2-yl}-5-(1-hydroxyethyl)-1H-pyrazole-3-carboxamide. It has activity against known AR mutants that confer resistance to other second-generation antiandrogens. Darolutamide binds to the AR with high affinity and impairs subsequent androgen-induced nuclear translocation of AR and transcription of AR gene target, Matsubara, N., Mukai, H., Hosono, A. et al. Cancer Chemother Pharmacol (2017) 80; 1063.

Certain Terminology

The terms used herein carry their normally accepted meaning, but for avoidance of doubt, some of the definitions are provided herein.

The term "cancer" as used herein refers to an abnormal growth of cells which tend to proliferate in an uncontrolled way and, in some cases, to metastasize (spread).

The term "prostate cancer" as used herein refers to histologically or cytologically confirmed adenocarcinoma of the prostate.

The term "androgen-deprivation therapy (ADT)" refers to the reduction of androgen levels in a prostate cancer patient to castrated levels of testosterone (<50 ng/dL). Such treatments can include orchiectomy or the use of gonadotropin-releasing hormone agonists or antagonists. ADT includes surgical castration (orchiectomy) and/or the administration of luteinizing hormone-releasing hormone ("LHRH")/gonadotropin-releasing hormone (GnRH) agonists or antagonists to a human. Examples of GnRH agonist or antagonist is or comprises leuprolide, buserelin, nafarelin, histrelin, goserelin, deslorelin, degarelix, ozarelix, ABT-620 (elagolix), TAK-385 (relugolix), EP-100, KLH-2109 or triptorelin. In certain embodiments, examples of GnRH agonists include goserelin acetate, histrelin acetate, leuprolide acetate, and triptorelin palmoate.

The term "locally advanced prostate cancer" refers to prostate cancer where all actively cancerous cells appear to be confined to the prostate and the associated organs or neighbor organs (e.g., seminal vesicle, bladder neck, and rectal wall).

The term "high-risk localized prostate cancer" refers to locally advanced prostate cancer that has a probability of developing metastases or recurrent disease after primary therapy with curative intent. In some embodiments, high risk for development of metastases is defined as prostate specific antigen doubling time (PSADT)<20 months, <19 months, <18 months, <17 months, <16 months, <15 months, <14 months, <13 months, <12 months, or <11 months, <10 months, <9 months, <8 months, <7 months, <6 months, <5 months, <4 months, <3 months, <2 months, or <1 month. In some embodiments, high risk for development of metastases is defined as prostate specific antigen doubling time (PSADT)<10 months. In some embodiments, high risk for development of metastases is defined as having a high Gleason score or bulky tumor.

For the avoidance of doubt, the terms "castration-sensitive prostate cancer" and "hormone-sensitive prostate cancer" are equivalent and are used interchangeably.

The terms "castration-sensitive prostate cancer" and "hormone-sensitive prostate cancer" refer to cancer that is responsive to androgen-deprivation therapy (ADT) either as localized disease, biochemical relapse or in the metastatic setting.

The terms "metastatic castration-sensitive prostate cancer" and "metastatic hormone-sensitive prostate cancer" refers to cancer that has spread (metastasized) to other areas of the body, e.g., the bone, lymph nodes or other parts of the body in a male, and that is responsive to androgen-deprivation therapy (ADT).

The terms "non-metastatic castration-sensitive prostate cancer" refers to cancer that has not spread (metastasized) in a male, and that is responsive to androgen-deprivation therapy (ADT). In some embodiments, non-metastatic castration-sensitive prostate cancer is assessed with bone scan and computed tomography (CT) or magnetic resonance imaging (MRI) scans.

The term "CRPC" as used herein refers to castration-resistant prostate cancer. CRPC is prostate cancer that continues to grow despite the suppression of male hormones that fuel the growth of prostate cancer cells.

The term "metastatic castration-resistant prostate cancer" refers to castration-resistant prostate cancer that has metastasized to other parts of the human body.

Metastatic castration-sensitive prostate cancer (CSPC), refers to prostate cancer that still responds to testosterone suppression therapy.

The term "NM-CRPC" as used herein refers to non-metastatic castration-resistant prostate cancer. In some embodiments, NM-CRPC is assessed with bone scan and computed tomography (CT) or magnetic resonance imaging (MRI) scans.

The term "chemotherapy naive metastatic castration-resistant prostate cancer" refers to metastatic castration-resistant prostate cancer that has not been previously treated with a chemotherapeutic agent.

The term "post-abiraterone acetate-prednisone treated metastatic castration-resistant prostate cancer" refers to metastatic castration-resistant prostate cancer that has already been treated with abiraterone acetate.

The term "high risk NM-CRPC" refers to probability of a man with NM-CRPC developing metastases. In some embodiments, high risk for development of metastases is defined as prostate specific antigen doubling time (PSADT) <20 months, <19 months, <18 months, <17 months, <16 months, <15 months, <14 months, <13 months, <12 months, or <11 months, <10 months, <9 months, <8 months, <7 months, <6 months, <; 5 months, <4 months, <3 months, <2 months, or <1 month. In some embodiments, high risk for development of metastases is defined as prostate specific antigen doubling time (PSADT)<10 months. In some embodiments, high risk for development of metastases is defined as having local-regional recurrence (e.g. primary tumor bed, bladder neck, anastomotic area, pelvic lymph nodes).

The terms "co-administration" or the like, as used herein, encompass administration of the selected therapeutic agents to a single patient, and are intended to include treatment regimens in which the agents are administered by the same or different route of administration or at the same or different time.

The term "pharmaceutical combination" as used herein, means a product that results from the mixing or combining of more than one active ingredient and includes both fixed and non-fixed combinations of the active ingredients. The term "fixed combination" means that the active ingredients, e.g., apalutamide and a co-agent, are both administered to a patient simultaneously in the form of a single unit or single dosage form. The term "non-fixed combination" means that the active ingredients, e.g., apalutamide and a co-agent, are administered to a patient as separate units or separate dosage forms, either simultaneously, concurrently or sequentially with no specific intervening time limits, wherein such administration provides safe and effective levels of the two active ingredients in the body of the human male. The latter also applies to cocktail therapy, e.g., the administration of three or more active ingredients.

The term "FDHT-PET" refers to 18F-16P-fluoro-5a-dihydrotestosterone Positron Emission Tomography and is a technique that uses a tracer based on dihydrotestosterone and allows for a visual assessment of ligand binding to the androgen receptor in a patient. It may be used to evaluate pharmacodynamics of an androgen receptor directed therapy.

The term "continuous daily dosing schedule" refers to the administration of a particular therapeutic agent without any drug holidays from the particular therapeutic agent. In some embodiments, a continuous daily dosing schedule of a particular therapeutic agent comprises administration of a particular therapeutic agent every day at roughly the same time each day.

The terms "treat" and "treatment" refer to the treatment of a patient afflicted with a pathological condition and refers to an effect that alleviates the condition by killing the cancerous cells, but also to an effect that results in the inhibition of the progress of the condition, and includes a reduction in the rate of progress, a halt in the rate of progress, amelioration of the condition, and cure of the condition. Treatment as a prophylactic measure (i.e., prophylaxis) is also included. Unless otherwise specified, the terms "treat", and "treatment" refers to the totality of effects described, but on other embodiments, the terms may also refer to any one of the effects described, or exclusive of at least one effect.

The term "metastasis-free survival" or "MFS" refers to the percentage of subjects in a study who have survived without cancer spread for a defined period of time or death. MFS is usually reported as time from the beginning of enrollment, randomization or treatment in the study. MFS is reported for an individual or a study population. In the context of treatment of CRPC with an anti-androgen, an increase in the metastasis-free survival is the additional time that is observed without cancer having spread or death, whichever occurs first, as compared to treatment with placebo. In some embodiments, the increase in the metastasis-free survival is about 1 month, about 2 months, about 3 months, about 4 months, about 5 months, about 6 months, about 7 months, about 8 months, about 10 months, about 11 months, about 12 months, about 13 months, about 14 months, about 15 months, about 16 months, about 17 months, about 18 months, about 19 months, about 20 months, or greater than 20 months. In some embodiments, administration of a safe and effective amount of an anti-androgen provides an increase in the metastasis-free survival of a male human, optionally wherein the increase in the metastasis-free survival is relative to the mean survival rate of a population of male humans with the non-metastatic castration-resistant prostate cancer, said population having been treated with a placebo. In some embodiments, metastasis-free survival refers to the time from randomization to the time of first evidence of BICR-confirmed bone or soft tissue distant metastasis or death due to any cause, whichever occurs first.

The term "time to metastasis" is the time from randomization to the time of the scan that shows first evidence of BICR-confirmed radiographically detectable bone or soft tissue distant metastasis. In some embodiments, administration of a safe and effective amount of an anti-androgen provides improved anti-tumor activity as measured by time to metastasis (TTM).

The term "radiographic progression-free survival" is the time from randomization to first imaging-based documentation of progressive disease or death, whichever came first. A subject is considered to have radiographic progressive disease if the subject has either progression of soft tissue lesions measured by computed tomography or magnetic resonance imaging or new lesion on bone scan.

The term "progression-free survival" is based on RECIST v1.1 and is defined as follows: For subjects with at least one measurable lesion, progressive disease is defined as at least a 20% increase in the sum of diameters of target lesions taking as reference the smallest sum on study (this includes the baseline sum if that is the smallest on study). In addition to the relative increase of 20%, the sum must also demonstrate an absolute increase of at least 5 mm. Furthermore, the appearance of one or more new lesions is also considered progression. For subjects with only non-measurable disease observed on CT or MRI scans, unequivocal progression (representative of overall disease status change) or the appearance of one or more new lesions was considered progression. For new bone lesions detected on bone scans, a second imaging modality (e.g., CT or MRI) was required to confirm progression. In some embodiments, administration of a safe and effective amount of an anti-androgen provides improved anti-tumor activity as measured by progression-free survival rate.

The term "prostate cancer-specific survival" is defined as the time from randomization to the date of death if attributed to prostate cancer.

The term "PFS2" means the time from initial study randomization to $2^{nd}$ disease progression or death from any cause.

The term "time to symptomatic progression" is defined as the time from randomization to documentation in the CRF of any of the following (whichever occurs earlier): (1) development of a skeletal-related event (SRE): pathologic fracture, spinal cord compression, or need for surgical intervention or radiation therapy to the bone; (2) pain progression or worsening of disease-related symptoms requiring initiation of a new systemic anti-cancer therapy; or (3) development of clinically significant symptoms due to loco-regional tumor progression requiring surgical intervention or radiation therapy. In some embodiments, administration of a safe and effective amount of an anti-androgen provides improved anti-tumor activity as measured by time to symptomatic progression.

The term "time to pain progression" is defined as the time from randomization to pain progression (average increase in 2 points from baseline in Brief Pain Inventory-Short Form [BPI-SF] worst pain intensity observed at two consecutive evaluations ≥3 weeks apart, with an average worst pain score of >4 in patients who have had no decrease in opioids or initiation of chronic opioids, whichever occurs first). BPI-SF worst pain (item 3) is used for the time to pain progression end point. Scores range from 0 to 10, with lower scores representing lower levels of pain intensity; a change of 2 was the minimally important difference.

The term "time to skeletal-related event (SRE")" is defined as the time from date of randomization to the date of the first observation of an SRE (symptomatic pathologic fracture, spinal cord compression, radiation to bone, or surgery to bone).

The term "time to chronic opioid use" is defined as the time from date of randomization to the first date of confirmed chronic opioid use. Chronic opioid use was defined as administration of opioid analgesics for ≥3 weeks for oral or ≥7 days for nonoral formulations. For patients who were already receiving opioids at study entry, chronic opioid use was defined as a ≥30% increase in total daily dose of the opioid analgesics lasting for ≥3 weeks for oral or ≥7 days for nonoral formulations. Administration of as-needed (e.g., not fixed or scheduled dosage) opioid analgesics or extended opioid use for treatment other than the patient's prostate cancer did not require discontinuation from study treatment.

The term "time to symptomatic local progression" is defined as the time from date of randomization to date of symptomatic local progression, whichever occurs first. Examples of symptomatic local progression include, but are not limited to, urethral obstruction or bladder outlet obstruction.

The term "time to ECOG PS grade deterioration" is defined as the time from date of randomization to the first date of deterioration in ECOG PS grade (defined as the worsening of ECOG PS grade by at least 1 point).

The term "overall survival" is defined as the time from randomization to the date of death due to any cause. Survival data for subjects who are alive at the time of the analysis was to be censored on the last known date that they were alive. In addition, for subjects with no post-baseline information survival, data was to be censored on the date of randomization; for subjects who are lost to follow-up or who withdraw consent, data is censored on the last known date that they were alive. In some embodiments, administration of a safe and effective amount of an anti-androgen provides improved anti-tumor activity as measured by overall survival.

The term "time to cytotoxic chemotherapy" is defined as the time from randomization to documentation of a new cytotoxic chemotherapy.

The term "progression-free survival with the first subsequent therapy (PFS2) is defined as the time from randomization to investigator-assessed disease progression (PSA, radiographic, symptomatic, or any combination) during first subsequent anti-cancer therapy or death (any cause) prior to the start of the second subsequent anti-cancer therapy, whichever occurs first.

The term "time to PSA progression" is defined as the time from randomization to date of PSA progression based on Prostate Cancer Working Group 2 criteria. Scher HI, et al. J Clin Oncol 2008; 26:1148-1159.

The term "time to second progression-free survival" is defined as the time from randomization to first occurrence of investigator-determined disease progression (PSA progression, progression on imaging, or clinical progression) while patient was receiving first subsequent therapy for prostate cancer or death due to any cause, whichever occurs first. Progression data for subjects without documented progression after subsequent therapy is censored at the last date known to be progression-free or date of death. In some embodiments, administration of a safe and effective amount of an anti-androgen provides improved anti-tumor activity as measured progression-free survival with the first subsequent therapy.

Prostate specific antigen response and time to PSA progression is assessed at the time of the primary analysis of MFS according to the Prostate Cancer Working Group (PCWG2) criteria. The time to PSA progression is calculated as the time from randomization to the time when the criteria for PSA progression according to PCWG2 are met.

The term "placebo" as used herein means administration of a pharmaceutical composition that does not include a second-generation anti-androgen. In the context of treatment of metastatic castration-sensitive prostate cancer, men that are administered an anti-androgen or placebo will need to continue to maintain castrated levels of testosterone by either co-administration of a GnRH agonist/antagonist or orchiectomy.

The term "survival benefit" as used herein means an increase in survival of the patient from time of randomization on the trial of administered drug to death. In some embodiments, the survival benefit is about 1, about 2, about 3, about 4, about 5, about 6, about 7, about 8, about 9, about 10, about 15, about 20, about 25, about 30, about 35, about 40, about 45, about 50, about 55, about 60, about 80, about 100 months or greater than 100 months.

The term "delay in symptoms related to disease progression" as used herein means an increase in time in the development of symptoms such as pain, urinary obstruction and quality of life considerations from the time of randomization on the trial of administered drug.

The term 'randomization' as it refers to a clinical trial refers to the time when the patient is confirmed eligible for the clinical trial and gets assigned to a treatment arm.

The terms "kit" and "article of manufacture" are used as synonyms.

The term "subject" and "patient" and "human" are used interchangeably.

Routes of Administration and Pharmaceutical Compositions

Therapeutic agents described herein are administered in any suitable manner or suitable formulation. Suitable routes of administration of the therapeutic agents include, but are not limited to, oral and parenteral (e.g., intravenous, subcutaneous, intramuscular). All formulations are in dosages suitable for administration to a human. A summary of pharmaceutical compositions can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

Studies that look at safety also seek to identify any potential adverse effects that may result from exposure to the drug. Efficacy is often measured by determining whether an active pharmaceutical ingredient demonstrates a health benefit over a placebo or other intervention when tested in an appropriate situation, such as a tightly controlled clinical trial.

Unless otherwise specified, the terms "effective amount" or "therapeutically effective amount," as used herein, refer to an amount of an anti-androgen being administered that treats the underlying disease or condition including, halting or slowing the progression of the disease or condition.

The term "acceptable" with respect to a formulation, composition or ingredient, as used herein, means that the beneficial effects or that formulation, composition or ingredient on the general health of the male human being treated substantially outweigh its detrimental effects, to the extent any exist.

In some embodiments, the anti-androgen is present in a solid oral dosage form. In some embodiments, the anti-androgen is formulated as an oral dose form, a unit oral dose form, or a solid dose form (e.g., a capsule, tablet, or pill). In some embodiments, for example, the anti-androgen is formulated as a tablet. In some embodiments, the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide. In some embodiments, the anti-androgen is 4-(3-(4-cyano-3-(trifluoromethyl)phenyl)-5,5-dimethyl-4-oxo-2-thioxoimidazolidin-1-yl)-2-fluoro-N-methylbenzamide. In some embodiments, the anti-androgen is 4-[7-[4-cyano-3-(trifluoromethyl)phenyl]-8-oxo-6-thioxo-5,7-diazaspiro [3.4]oct-5-yl]-2-fluoro-N-methylbenzamide. In some embodiments, the anti-androgen is N-{(2S)-1-[3-(3-chloro-4-cyanophenyl)-1H-pyrazol-1-yl]propan-2-yl}-5-(1-hydroxyethyl)-1H-pyrazole-3-carboxamide. Formulations may also comprise two or more of these materials in combinations. Solid oral dosage forms containing the anti-androgen may be provided as soft gel capsules as disclosed in WO2014113260 and CN104857157, each of which is incorporated herein by reference, or as tablets as disclosed in WO2016090098, WO2016090101, WO2016090105, and WO2014043208, each of which is incorporated herein by reference. Techniques suitable for preparing solid oral dosage forms of the present invention are described in Remington's Pharmaceutical Sciences, 18th edition, edited by AR. Gennaro, 1990, Chapter 89, and in Remington—The Science, and Practice of Pharmacy, 21st edition, 2005, Chapter 45.

In certain embodiments, the anti-androgen is present in a solid unit dosage form, and a solid unit dosage form suitable for oral administration. The unit dosage form may contain about 10, 20, 30, 40, 50, 60, 70, 80, 90, 100, 110, 120, 130, 140, 150, 160, 170, 180, 190, 200, 210, 220, or 240 mg of the anti-androgen per unit dose form or an amount in a range bounded by two of these values.

To prepare the pharmaceutical compositions of this invention, the active pharmaceutical ingredient is intimately admixed with a pharmaceutical carrier according to conventional pharmaceutical compounding techniques, which carrier may take a wide variety of forms depending of the form of preparation desired for administration (e.g., oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

In solid oral preparations such as, for example, dry powders for reconstitution or inhalation, granules, capsules, caplets, gel caps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

Preferably these compositions are in unit dosage forms from such as tablets, pills, capsules, dry powders for reconstitution or inhalation, granules, lozenges, sterile solutions or suspensions, metered aerosol or liquid sprays, drops, or suppositories for administration by oral, intranasal, sublingual, intraocular, transdermal, rectal, vaginal, dry powder inhaler or other inhalation or insufflation means.

These formulations are manufactured by conventional formulation techniques. For preparing solid pharmaceutical compositions such as tablets, the principal active ingredient is mixed with a pharmaceutical carrier, e.g., conventional tableting ingredients such as diluents, binders, adhesives, disintegrants, lubricants, antiadherents, and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE available from Hoechst Celanese], polyethylene glycol, polysaccharide acids, bentonites, polyvinylpyrrolidone, polymethacrylates and pregelatinized starch) and the like. Suitable disintegrants include, but am not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL silica available from Cabot, SYLOID silica available from W.R. Grace/Davison, and AEROSIL silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

An aspect of the invention is a solid dispersion comprising the anti-androgen. Various techniques exist for preparing the solid dispersions of the invention including melt-extrusion (e.g. hot melt extrusion), spray-drying and solution-evaporation, in particular hot melt-extrusion and spray-drying, spray-drying being preferred. An aspect of the invention is a particle consisting of a solid dispersion as described herein. In an aspect of the invention, the particles as described herein are obtainable, in particular are obtained, by spray drying a mixture comprising the anti-androgen generally and ARN-509 more specifically and HPMCAS in a suitable solvent. In an aspect, the particles are obtainable, in particular are obtained, by melt extrusion.

HPMCAS or hydroxypropyl methylcellulose acetate succinate or hypromellose acetate succinate (CAS number 71138-97-1) is a mixture of acetic acid and monosuccinic acid esters of hydroxypropylmethyl cellulose (IUPAC name: cellulose, 2-hydroxypropyl methyl ether, acetate, hydrogen butanedioate). Different grades are available differentiated based on degree/ratio of substitution (acetyl content, succinoyl content) and particle size (micronized and granular). In an aspect of the invention, the HPMCAS in the dispersions with ARN-509 is HPMCAS LG (granular grade) or HPMCAS LF (micronized grade) (Shin-Etsu Chemical Co., Ltd), in particular HPMCAS LG.

Binders suitable for use in the pharmaceutical compositions provided herein include, but are not limited to, starches, cellulose, and its derivatives (e.g., ethylcellulose, cellulose acetate, carboxymethyl cellulose calcium, sodium carboxymethyl cellulose, methylcellulose, hydroxypropyl methylcellulose), polyvinyl pyrrolidone, and mixtures thereof.

Examples of fillers suitable for use in the pharmaceutical compositions provided herein include, but are not limited to, microcrystalline cellulose, powdered cellulose, mannitol, lactose, calcium phosphate, starch, pre-gelatinized starch, and mixtures thereof.

The binder or filler in pharmaceutical compositions is typically present in from about 50 to about 99 weight percent of the pharmaceutical composition or dosage form.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant. Disintegrants that can be used in the pharmaceutical compositions provided herein include, but are not limited to, croscarmellose sodium, crospovidone, sodium starch glycolate, potato or tapioca starch, pre-gelatinized starch, other starches, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, polyethylene glycol, other glycols, stearic acid, sodium lauryl sulfate, sodium stearyl fumarate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Lubricants are typically used in an amount of less than about 1 weight percent of the pharmaceutical compositions or dosage forms into which they are incorporated.

Compressed tablet formulations may optionally be film-coated to provide color, light protection, and/or taste-masking. Tablets may also be coated so as to modulate the onset, and/or rate of release in the gastrointestinal tract, so as to optimize or maximize the biological exposure of the patient to the API.

Hard capsule formulations may be produced by filling a blend or granulation of apalutamide or enzalutamide into shells consisting of, for example, gelatin, or hypromellose.

Soft gel capsule formulations may be produced.

Pharmaceutical compositions intended for oral use may be prepared from the solid dispersion formulations, and blended materials described above in accordance with the methods described herein, and other methods known to the art for the manufacture of pharmaceutical compositions. Such compositions may further contain one or more agents selected from the group consisting of sweetening agents, flavoring agents, coloring agents, and preserving agents in order to provide pharmaceutically elegant and palatable preparations.

Tablets may contain the active ingredient in admixture with non-toxic pharmaceutically acceptable excipients that are suitable for the manufacture of tablets. These excipients may be for example, inert diluents, granulating, and disintegrating agents, binding agents, glidants, lubricating agents, and antioxidants, for example, propyl gallate, butylated hydroxyanisole, and butylated hydroxy toluene. The tablets may be uncoated, or they may be film coated to modify their appearance or may be coated with a functional coat to delay disintegration, and absorption in the gastrointestinal tract, and thereby provide a sustained action over a longer period.

Compositions for oral use may also be presented as capsules (e.g., hard gelatin) wherein the active ingredient is mixed with an inert solid diluent, for example, calcium carbonate, calcium phosphate or starch, or as soft gelatin capsules wherein the active ingredient is mixed with liquids or semisolids, for example, peanut oil, liquid paraffin, fractionated glycerides, surfactants or olive oil. Aqueous suspensions contain the active materials in mixture with excipients suitable for the manufacture of aqueous suspensions. Dispersible powders and granules suitable for preparation of an aqueous suspension by the addition of water provide the active ingredient in mixture with a dispersing or wetting agent, suspending agent, and one or more preservatives. In certain embodiments of the invention, the pharmaceutical compositions of the invention include a diluent system, disintegrant, salt, lubricant, glidant, and filmcoat, at concentrations of from about 3% w/w to about 58% w/w, from about 4% w/w to about 20% w/w, from about 4% w/w to about 20% w/w, from about 0.5% w/w to about 4% w/w, from about 0% w/w to about 2% w/w, and from about 1% w/w to about 5% w/w respectively, or at from about 18% w/w to about 40% w/w, from about 7% w/w to about 15% w/w, from about 7% w/w to about 18% w/w, from about 1.0% w/w to about 3.0%, from about 0.1% w/w to about 1.0% w/w, and from about 2.0% w/w to about 4.0% w/w, respectively. In certain embodiments, the solid dispersion formulations are blended with a diluent, one or more disintegrating agents, lubricants, and glidants. An exemplary blended composition or oral dosage form includes mannitol, microcrystalline cellulose, croscarmellose sodium, sodium chloride, colloidal silica, sodium stearyl fumarate, and magnesium stearate.

The disintegrant may be present in a concentration from about 4% w/w to about 20% w/w or from about 7% w/w to about 15% w/w. A salt may be also present, which may be sodium chloride, potassium chloride or a combination thereof. The combination of salts and disintegrant is present at a concentration from about 5% w/w to about 35% w/w of the final pharmaceutical composition.

In certain embodiments, inactive ingredients of the core tablet are: colloidal anhydrous silica, croscarmellose sodium, hydroxypropyl methylcellulose-acetate succinate, magnesium stearate, microcrystalline cellulose, and silicified microcrystalline cellulose. In other embodiments, the tablets are finished with a film-coating consisting of the following excipients: iron oxide black, iron oxide yellow, polyethylene glycol, polyvinyl alcohol, talc, and titanium dioxide In other embodiments, a single unit dosage of the pharmaceutical composition comprises, consists of, or consists essentially of about 60 mg of apalutamide. In some embodiments, multiple doses of the single unit dosage pharmaceutical composition comprising, consisting of, or consisting essentially of about 60 mg of apalutamide, e.g., 4 multiple or individual unit dosage forms, are administered to the human. The total daily dose of apalutamide may be about 240 mg per day.

In some embodiments, a single unit dosage of the pharmaceutical composition comprises, consists of, or consists essentially of about 40 mg of enzalutamide. In some embodiments, multiple doses of the single unit dosage pharmaceutical composition comprising, consisting of, or consisting essentially of about 40 mg of enzalutamide, e.g., 4 multiple or individual unit dosage forms, are administered to the human. The total daily dose of enzalutamide may be about 160 mg per day.

In still further embodiments, a single unit dosage of the pharmaceutical composition comprises, consists of, or consists essentially of about 300 mg of darolutamide. In some embodiments, multiple doses of the single unit dosage pharmaceutical composition comprising, consisting of, or consisting essentially of about 300 mg of darolutamide, e.g., 2 multiple or individual unit dosage forms, are administered to the human. The total daily dose of darolutamide may be about 600 mg twice daily. The total daily dose of darolutamide may be about 1200 mg per day.

All formulations for oral administration are in dosage form suitable for such administration.

Methods of Dosing and Treatment Regimens in one aspect described herein are methods of treating metastatic castration-sensitive prostate cancer in a male human comprising, consisting of, or consisting essentially administering a therapeutically effective amount of an anti-androgen to a male human with metastatic castration-sensitive prostate cancer, wherein the anti-androgen is at least one of: 4-[7-(6-cyano-5-trifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide, or N-{(2S)-[3-(3-chloro-4-cyanophenyl)-1H-pyrazol-1-yl]propan-2-yl}-5-(1-hydroxyethyl)-1H-pyrazole-3-carboxamide. In the following disclosure. "methods of treating metastatic castration-sensitive prostate cancer," may alternatively be recited as "methods of treating a male human having metastatic castration-sensitive prostate cancer." For the sake of brevity, each possible alternative is not parsed out, but each are considered separately considered as if fully described.

Also disclosed herein are methods for treating metastatic castration-sensitive prostate cancer in a male human consisting or consisting essentially of administering a therapeutically effective amount of an anti-androgen to a male human with metastatic castration-sensitive prostate cancer, wherein the anti-androgen is one or more of: 4-[7-(6-cyano-5-trifluoromethylpyridintrifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide or N-{(2S)-1-[3-(3-chloro-4-cyanophenyl)-1H-pyrazol-1-yl]propan-2-yl}-5-(1-hydroxyethyl)-1H-pyrazole-3-carboxamide.

In another aspect described herein, administration of the anti-androgen provides an increase in overall survival of the male human relative to the overall survival rate of a comparative population of male humans with the metastatic castration-sensitive prostate cancer, said comparative population having been administered a placebo in combination with an androgen deprivation therapy, said placebo having been administered prior to or during the administration of the anti-androgen. In other embodiments, the comparative population is untreated. In another aspect described herein, administration of the anti-androgen provides an increase in overall survival of the male human relative to the overall survival rate of a comparative population of male humans with the metastatic castration-sensitive prostate cancer, said comparative population having been administered androgen deprivation therapy. In certain embodiments, administration of the anti-androgen provides an increase in overall survival of the male human relative to the overall survival rate of a comparative population of male humans with the metastatic castration-sensitive prostate cancer, said comparative population having received no treatment. In certain embodiments, administration of the anti-androgen provides an increase in overall survival of the male human relative to the overall survival rate of a comparative population of male humans with the metastatic castration-sensitive prostate cancer, said comparative population having been administered a first-generation anti-androgen, with or without androgen deprivation therapy. In some embodiments, the population to whom the anti-androgen is administered and the comparative population both have been previously been treated by the same or similar prior treatment regimen.

In further embodiments, administration of the anti-androgen provides an increase in progression-free survival of the male human relative to the progression-free survival rate of a comparative population of male humans with the metastatic castration-sensitive prostate cancer, said comparative population having been administered a placebo in combination with an androgen deprivation therapy. In another aspect described herein, administration of the anti-androgen provides an increase in progression-free survival of the male human relative to the progression-free survival rate of a comparative population of male humans with the metastatic castration-sensitive prostate cancer, said comparative population having previously been administered androgen deprivation therapy. In certain embodiments, administration of the anti-androgen provides an increase in progression-free survival of the male human relative to the progression-free survival rate of a comparative population of male humans with the metastatic castration-sensitive prostate cancer, said comparative population having previously received no treatment. In certain embodiments, administration of the anti-androgen provides an increase in progression-free survival of the male human relative to the progression-free survival rate of a comparative population of male humans with the metastatic castration-sensitive prostate cancer, said comparative population having been previously administered a first-generation anti-androgen, with or without androgen deprivation therapy. Again, in preferred embodiments, the population to whom the anti-androgen is administered and the comparative population have both been previously experienced the same or similar prior treatment regimen.

In one aspect, described herein are methods of treating metastatic castration-sensitive prostate cancer comprising, consisting of, or consisting essentially of administering a therapeutically effective amount of an anti-androgen to a male human with a metastatic castration-sensitive prostate cancer, wherein the anti-androgen is administered orally. In some embodiments, the anti-androgen is administered daily. In some embodiments, the anti-androgen is administered twice-a-day. In some embodiments, the anti-androgen is administered three times a day. In some embodiments, the anti-androgen is administered four times a day. In some embodiments, the anti-androgen is administered every other day. In some embodiments, the anti-androgen is administered weekly. In some embodiments, the anti-androgen is administered twice a week. In some embodiments, the anti-androgen is administered every other week. In some embodiments, the anti-androgen is administered orally on a continuous daily dosage schedule.

In one embodiment, the desired dose is conveniently presented in a single dose or in divided doses administered simultaneously (or over a short period of time) or at appropriate intervals, for example as two, three, four or more sub-doses per day. In some embodiments, the anti-androgen is conveniently presented in divided doses that are administered simultaneously (or over a short period of time) once a day. In some embodiments, the anti-androgen is conveniently presented in divided doses that are administered in equal portions twice-a-day. In some embodiments, the anti-androgen is conveniently presented in divided doses that are administered in equal portions three times a day. In some embodiments, the anti-androgen is conveniently presented in divided doses that are administered in equal portions four times a day.

In certain embodiments, the desired dose may be delivered in 1, 2, 3, 4, 5, 6, 7, 8, 9, or 10 fractional unit dosages throughout the course of the day, such that the total amount of anti-androgens delivered by the fractional unit dosages over the course of the day provides the total daily dosages.

In further embodiments, 4-[7-(6-cyano-S-trifluoromethylpyridin-3-yl)-8-oxo-6-thioxo-5,7-diazaspiro[3.4]oct-5-yl]-2-fluoro-N-methylbenzamide is administered daily to the male human. In still further embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human on a continuous daily dosing schedule.

In further embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered daily to the male human. In still further embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human. In some embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered orally to the male human on a continuous daily dosing schedule.

In further embodiments, 4-[7-[4-cyano-3-(trifluoromethyl)phenyl]-8-oxo-6-thioxo-5,7-diazaspiro[3.4]oct-5-yl]-2-fluoro-N-methylbenzamide is administered daily to the male human. In still further embodiments. 4-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human. In some embodiments, 4-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human on a continuous daily dosing schedule.

In further embodiments, N-{(2S)-1-[3-(3-chloro-4-cyanophenyl)-1H-pyrazol-1-yl]propan-2-yl}-5-(1-hydroxyethyl)-

1H-pyrazole-3-carboxamideis is administered daily to the male human. In still further embodiments, N-{(2S)-1-[3-(3-chloro-4-cyanophenyl)-1H-pyrazol-1-yl]propan-2-yl}-5-(1-hydroxyethyl)-1H-pyrazole-3-carboxamideis is administered orally to the male human. In some embodiments, N-{(2S)-1-[3-(3-chloro-4-cyanophenyl)-1H-pyrazol-1-yl]propan-2-yl}-5-(1-hydroxyethyl)-1H-pyrazole-3-carboxamideis is administered orally to the male human on a continuous daily dosing schedule.

In some embodiments, the anti-androgen is a second-generation anti-androgen. In certain embodiments, the anti-androgen is enzalutamide, apalutamide, RD-162 or darolutamide. In some embodiments, the anti-androgen is apalutamide. In some embodiments, the anti-androgen is enzalutamide. In some embodiments, the anti-androgen is RD-162. In some embodiments, the anti-androgen is darolutamide.

In general, doses of the anti-androgen employed for treatment of the diseases or conditions described herein in humans are typically in the range of 10 mg to 1000 mg per day. In some embodiments, the anti-androgen is administered orally to the human at a dose of about 30 mg per day to about 1200 mg per day. In some embodiments, the anti-androgen is administered orally to the human at a dose of about 30 mg per day to about 600 mg per day. In some embodiments, the anti-androgen is administered orally to the human at a dose of about 30 mg per day, about 60 mg per day, about 90 mg per day, about 120 mg per day, about 160 mg per day, about 180 mg per day, about 240 mg per day, about 300 mg per day, about 390 mg per day, about 480 mg per day, about 600 mg per day, about 780 mg per day, about 960 mg per day, or about 1200 mg per day.

In certain embodiments, the doses of the anti-androgen employed for treatment of the diseases or conditions described herein in humans may have a range of from 30 to 40 mg/day, 40 to 50 mg/day, 50 to 60 mg/day, 60 to 70 mg/day, 70 to 80 mg/day, 80 to 90 mg/day, 90 to 100 mg/day, 100 to 120 mg/day, 120 to 140 mg/day, 140 to 160 mg/day, 160 to 180 mg/day, 180 to 200 mg/day, 200 to 220 mg/day, 220 to 240 mg/day, 240 to 260 mg/day, 260 to 280 mg/day, 280 to 300 mg/day, 300 to 320 mg/day, 320 to 340 mg/day, 340 to 360 mg/day, 360 to 380 mg/day, 380 to 400 mg/day, 400 to 420 mg/day, 420 to 440 mg/day, 440 to 460 mg/day, 460 to 480 mg/day, or any range defined by two or more of these ranges, or any individual value cited in these ranges.

In some embodiments, the doses of the anti-androgen employed for treatment of the diseases or conditions described herein in humans may have a range of from 0.3 to 0.4 mg/kg/day, 0.4 to 0.5 mg/kg/day, 0.5 to 0.6 mg/kg/day, 0.6 to 0.7 mg/kg/day, 0.7 to 0.8 mg/kg/day, 0.8 to 0.9 mg/kg/day, 0.9 to 1 mg/kg/day, 1 to 1.2 mg/kg/day, 1.2 to 1.4 mg/kg/day, 1.4 to 1.6 mg/kg/day, 1.6 to 1.8 mg/kg/day, 1.8 to 2 mg/kg/day, 2 to 2.2 mg/kg/day, 2.2 to 2.4 mg/kg/day, 2.4 to 2.6 mg/kg/day, 2.6 to 2.8 mg/kg/day, 2.8 to 3.0 mg/kg/day, 3.0 to 3.2 mg/kg/day, 3.2 to 3.4 mg/kg/day, 3.4 to 3.6 mg/kg/day, 3.6 to 3.8 mg/kg/day, 3.8 to 4.0 mg/kg/day, 4.0 to 4.2 mg/kg/day, 4.2 to 4.4 mg/kg/day, 4.4 to 4.6 ng/kg/day, 4.6 to 4.8 mg/kg/day, or any range defined by two or more of these ranges, or any individual value cited in these ranges In further embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 30 mg per day to about 480 mg per day. In still further embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 180 mg per day to about 480 mg per day. In certain embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of: (a) about 30 mg per day; (b) about 60 mg per day; (c) about 90 mg per day; (d) about 120 mg per day; or (d) about 240 mg per day. In some embodiments, 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

In some embodiments, the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 180 mg per day if the male human experiences a greater than or equal to Grade 3 toxicity. Alternatively, or in addition, the original dosing may be held until the toxicity symptoms improve to less than or equal to Grade 1 toxicity; the dosing may then be decreased as noted herein or resumed at the original dosing with continued monitoring. In some embodiments, the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 180 mg per day if the male human experiences an intolerable side effect. In some embodiments, the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 120 mg per day if the male human experiences a greater than or equal to Grade 3 toxicity. Alternatively, or in addition, the original dosing may be held until the toxicity symptoms improve to less than or equal to Grade 1 toxicity; the dosing may then be decreased as noted herein or resumed at the original dosing with continued monitoring. In some embodiments, the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 120 mg per day if the male human experiences an intolerable side effect.

In some embodiments, 4-(3-(4-cyano-3-(trifluoromethyl)phenyl)-5,5-dimethyl-4-oxo-2-thioxoimidazolidin-1-yl)-2-fluoro-N-methylbenzamide is administered orally at a dose of about 160 mg per day. In some embodiments, greater than 160 mg per day of enzalutamide is administered.

In some embodiments, 4-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human at a dose of about 30 mg per day to about 480 mg per day. In still further embodiments, 44-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human at a dose of about 180 mg per day to about 480 mg per day. In certain embodiments, 4-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human at a dose of: (a) about 30 mg per day; (b) about 60 mg per day; (c) about 90 mg per day; (d) about 120 mg per day; or (d) about 240 mg per day. In some embodiments, 44-[7-[4-cyano-3-(trifluoromethyl)phenyl]-8-oxo-6-thioxo-5,7-diazaspiro[3.4]oct-5-yl]-2-fluoro-N-methylbenzamide is administered orally to the male human at a dose of about 240 mg per day.

In some embodiments, the N-{(2S)-1-[3-(3-chloro-4-cyanophenyl)-1H-pyrazol-1-yl]propan-2-yl}-5-(i-hydroxyethyl)-1H-pyrazole-3-carboxamide is administered orally at a dose of about 1200 mg per day. In some embodiments, greater than 1200 mg per day of N-{(2S)-1-[3-(3-chloro-4-cyanophenyl)-1H-pyrazol-1-yl]propan-2-yl}-5-(1-hydroxyethyl)-1H-pyrazole-3-carboxamide is administered.

In certain embodiments, wherein improvement in the status of the disease or condition in the human is not observed, the daily dose of anti-androgen is increased. In some embodiments, a once-a-day dosing schedule is changed to a twice-a-day dosing schedule. In some embodiments, three times a day dosing schedule is employed to increase the amount of anti-androgen that is administered.

In some embodiments, the amount of anti-androgen that is given to the human varies depending upon factors such as, but not limited to, condition and severity of the disease or condition, and the identity (e.g., weight) of the human, and the particular additional therapeutic agents that are administered (if applicable).

In some embodiments, the male human received at least one prior therapy for the treatment of cancer, wherein the prior therapy for the treatment of cancer is radiation, surgical intervention or docetaxel therapy. In some embodiments, the male human is treatment naïve.

In some embodiments, the anti-androgen is administered in combination with androgen deprivation therapy. In further embodiments, anti-androgen is administered in combination with at least one gonadotropin-releasing hormone (GnRH) agonist or antagonist. In still further embodiments, the at least one GnRH agonist or antagonist is or comprises leuprolide, buserelin, naferelin, histrelin, goserelin, deslorelin, degarelix, ozarelix, ABT-620 (elagolix), TAK-385 (relugolix), EP-100, KLH-2109 or triptorelin.

Physicians can prescribe GnRH agonists in accordance with instructions, recommendations and practices. In some embodiments, the gonadotropin-releasing hormone agonist or antagonist is leuprolide. In some embodiments, leuprolide is administered as a depot injection at a dose of about 7.5 mg every 4 weeks, or 22.5 mg every 3 months, or about 30 mg every 4 months, or about 45 mg every 6 months. In some embodiments, leuprolide is administered at about 0.01 mg to about 200 mg of leuprolide over a period of about 3 days to about 12 months, preferably about 3.6 mg of leuprolide over a period of about 3 days to about 12 months. In some embodiments, the gonadotropin-releasing hormone agonist or antagonist is buserelin. In some embodiments, the gonadotropin-releasing hormone agonist or antagonist is naferelin. In some embodiments, the gonadotropin-releasing hormone agonist or antagonist is histrelin. In some embodiments, the gonadotropin-releasing hormone agonist or antagonist is histrelin acetate. In some embodiments, histrelin acetate is administered at about 50 mg of histrelin acetate over a period of 12 months of histrelin acetate or about 50 µg per day of histrelin acetate. In some embodiments the GnRH agonist or antagonist is goserelin. In some embodiments, goserelin is administered as a subcutaneous implant at a dose of about 3.6 mg every 4 weeks or about 10.8 mg every 12 weeks. In some embodiments, goserelin is administered at about 0.01 mg to about 20 mg of goserelin over a period of about 28 days to about 3 months, preferably about 3.6 mg to about 10.8 mg of goserelin over a period of about 28 days to about 3 months. In some embodiments the GnRH agonist or antagonist is deslorelin. In some embodiments, the gonadotropin-releasing hormone agonist or antagonist is degarelix. In some embodiments, degarelix is administered as a subcutaneous injection at a dose of about 240 mg followed by about 80 mg administered every 4 weeks. In some embodiments the GnRH agonist or antagonist is ozarelix. In some embodiments the GnRH agonist or antagonist is ozarelix. In some embodiments the GnRH agonist or antagonist is ABT-620 (elagolix). In some embodiments the GnRH agonist or antagonist is TAK-385 (relugolix). In some embodiments the GnRH agonist or antagonist is EP-100. In some embodiments the GnRH agonist or antagonist is KLH-2109. In some embodiments, the gonadotropin-releasing hormone agonist or antagonist is triptorelin. In some embodiment, triptorelin is administered at about 0.01 mg to about 20 mg of triptorelin over a period of about 1 month, preferably about 3.75 mg of triptorelin over a period of 1 month.

In certain embodiments, the anti-androgen is used in combination with bilateral orchiectomy. In certain embodiments, the anti-androgen is administered post-bilateral orchiectomy.

In still further embodiments, the 4-[7-(6-cyano-5-trifluoromethylpyridin-3-yl)-8-oxo-6-thioxo-5,7-diazaspiro[3.4]oct-5-yl]-2-fluoro-N-methylbenzamide is not co-administered with: (a) a medication that is a strong CYP2C8 or CYP3A4 inhibitor; (b) a medication that is primarily metabolized by CYP3A4, CYP2C9, or CYP2C9; (c) a medication that is a substrate of UDP-glucuronosyl transferase (UGT); or (d) a medication that is a substrate of P-glycoprotein, BCRP or OATP1B1. In certain embodiments, the 4-[7-(6-cyano-5-trifluoromethylpyridin-3-yl)-8-oxo-6-thioxo-5,7-diazaspiro[3.4]oct-5-yl]-2-fluoro-N-methylbenzamide is not co-administered with a medication that is a strong CYP2C8 or CYP3A4 inhibitor. In certain embodiments, the 4-[7-(6-cyano-5-trifluoromethylpyridin-3-yl)-8-oxo-6-thioxo-5,7-diazaspiro[3.4]oct-5-yl]-2-fluoro-N-methylbenzamide is not co-administered with a medication that is primarily metabolized by CYP3A4, CYP2C19, or CYP2C9. In certain embodiments, the 4-[7-(6-cyano-5-trifluoromethylpyridin-3-yl)-8-oxo-6-thioxo-5,7-diazaspiro[3.4]oct-5-yl]-2-fluoro-N-methylbenzamide is not co-administered with a medication that is a substrate of UDP-glucuronosyl transferase (UGT); or (d) a medication that is a substrate of P-glycoprotein, BCRP or OATP1B1.

A non-limiting example of a strong CYP2C8 inhibitors is gemfibrozil.

Non-limiting examples of strong CYP3A4 inhibitors include Boceprevir, Aprepitant, Clarithromycin, Conivaptan, grapefruit juice, Indinavir, Lopinavir, itraconazole. Mibefradil, Ketoconazole, Nefazodone, Ritonavir, Posaconazole, Nelfinavir, Saquinavir, Conivaptan, Telaprevir, Boceprevir, Telithromycin, Clarithromycin, Voriconazole, Clotrimazole. Diltiazem, Erythromycin, Fluconazole, Verapamil, and Troleandomycin.

Non-limiting examples of moderate to strong CYP3A4 inducers include Avasimibe. St. John's wort, Carbamazepine, Efavirenz, Phenytoin, Etravirine, Bosentan, Nafcillin, Rifampin, Modafinil, Rifabutin, and Barbiturates.

A non-limiting example of a medication that is primarily metabolized by CYP3A4 is midazolam. A non-limiting example of a medication that is primarily metabolized by CYP2C19 is omeprazole. A non-limiting example of a medication that is primarily metabolized by CYP2C9 is S-warfarin.

A non-limiting example of a medication that is a substrate of P-glycoprotein is fexofenadine.

A non-limiting example of a medication that is a substrate of BCRP is rosuvastatin.

A non-limiting example of a medication that is a substrate of OATP1B1 is rosuvastatin.

In another aspect, provided herein are methods of treating metastatic castration-sensitive prostate cancer in a male human, comprising, consisting or consisting essentially of: (a) determining whether the male human has metastatic castration-sensitive prostate cancer; and (b) administering an anti-androgen to a male human in a therapeutically effective amount to treat the metastatic castration-sensitive prostate cancer, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide, 4-(3-(4-cyano-3-(trifluoromethyl)phenyl)-5,5-dimethyl-4-oxo-2-thioxoimidazolidin-1-yl)-2-fluoro-N-methylbenzamide, 4-[7-[4-cyano-3-(trifluoromethyl)phenyl]-8-oxo-6-thioxo-5,7-diazaspiro[3.4]oct-5-yl]-2-fluoro-N-methylbenzamide or N-{(2S)-1-[3-(3-chloro-4-cyanophenyl)-1H-pyrazol-1-yl]propan-2-yl}-5-(d-hydroxyethyl)-1H-pyrazole-3-carboxamideis.

Methods of Treatment Involving an Approved Drug Product

Also provided herein are methods of treating metastatic castration-sensitive prostate cancer in a male human comprising administering an approved drug product comprising apalutamide to a male human with metastatic castration-sensitive prostate cancer in an amount that is described in a drug product label for said drug product, in some embodiments, the approved drug product comprising apalutamide is an ANDA drug product, a supplemental New Drug Application drug product or a 505(b)(2) drug product. In certain embodiments, the method is clinically proven safe and/or effective. In certain embodiments, the method is clinically proven safe. In certain embodiments, the method is clinically proven effective.

The term, "drug product" or "approved drug product" is a product that contains an active pharmaceutical ingredient that has been approved for marketing for at least one indication by a governmental authority, e.g., the Food and Drug Administration or the similar authority in other countries.

Similarly, "label" or "drug product label" refers to information provided to a patient which provides relevant information regarding the drug product. Such information includes, without limitation, one or more of the description of the drug, clinical pharmacology, indications (uses for the drug product), contraindication (who should not take the drug product), warnings, precautions, adverse events (side effects), drug abuse and dependence, dosage and administration, use in pregnancy, use in nursing mothers, use in children and older patients, how the drug is supplied, safety information for the patient, or any combination thereof. In certain embodiments, the label or drug product label provides an instruction for use in a patient with metastatic castration-sensitive prostate cancer. In further embodiments, the label or drug product label identifies apalutamide as a regulatory approved chemical entity. In still other embodiments, the label comprises data for superior efficacy in improving radiographic progression-free survival or overall survival relative to placebo. In yet further embodiments, the label instructs a patient or a physician to administer the apalutamide if the patient has metastatic castration-sensitive prostate cancer.

The term "Reference Listed Drug (RLD)" is a drug product to which new generic versions are compared to show that they are bioequivalent. See 21 CFR 314.3(b)). It is also a medicinal product that has been granted marketing authorization by a Member State of the European Union or by the Commission on the basis of a completed dossier, i.e., with the submission of quality, pre-clinical and clinical data in accordance with Articles 8(3), 10a, 10b or 10c of Directive 2001/83/EC and to which the application for marketing authorization for a generic/hybrid medicinal product refers, by demonstration of bioequivalence, usually through the submission of the appropriate bioavailability studies.

In the United States, a company seeking approval to market a generic equivalent must refer to the RLD in its Abbreviated New Drug Application (ANDA). For example, an ANDA applicant relies on the FDA's finding that a previously approved drug product, i.e., the RLD, is safe and effective, and must demonstrate, among other things, that the proposed generic drug product is the same as the RLD in certain ways. Specifically, with limited exceptions, a drug product for which an ANDA is submitted must have, among other things, the same active ingredient(s), conditions of use, route of administration, dosage form, strength, and (with certain permissible differences) labeling as the RLD. The RLD is the listed drug to which the ANDA applicant must show its proposed ANDA drug product is the same with respect to active ingredient(s), dosage form, route of administration, strength, labeling, and conditions of use, among other characteristics. In the electronic Orange Book, there is a column for RLDs and a column for reference standards. In the printed version of the Orange Book, the RLDs and reference standards are identified by specific symbol. For an ANDA based on an approved suitability petition (a petitioned ANDA), the reference listed drug generally is the listed drug referenced in the approved suitability petition.

A reference standard is the drug product selected by FDA that an applicant seeking approval of an ANDA must use in conducting an in vivo bioequivalence study required for approval. FDA generally selects a single reference standard that ANDA applicants must use in in vivo bioequivalence testing. Ordinarily, FDA will select the reference listed drug as the reference standard. However, in some instances (e.g., where the reference listed drug has been withdrawn from sale and FDA has determined it was not withdrawn for reasons of safety or effectiveness, and FDA selects an ANDA as the reference standard), the reference listed drug and the reference standard may be different.

FDA identifies reference listed drugs in the Prescription Drug Product, OTC Drug Product, and Discontinued Drug Product Lists. Listed drugs identified as reference listed drugs represent drug products upon which an applicant can rely in seeking approval of an ANDA. FDA intends to update periodically the reference listed drugs identified in the Prescription Drug Product, OTC Drug Product, and Discontinued Drug Product Lists, as appropriate.

FDA also identifies reference standards in the Prescription Drug Product and OTC Drug Product Lists. Listed drugs identified as reference standards represent the FDA's best judgment at this time as to the appropriate comparator for purposes of conducting any in vivo bioequivalence studies required for approval.

In some instances when FDA has not designated a listed drug as a reference listed drug, such listed drug may be shielded from generic competition. If FDA has not designated a reference listed drug for a drug product the applicant intends to duplicate, the potential applicant may ask FDA to designate a reference listed drug for that drug product.

FDA may, on its own initiative, select a new reference standard when doing so will help to ensure that applications for generic drugs may be submitted and evaluated, e.g., in the event that the listed drug currently selected as the reference standard has been withdrawn from sale for other than safety and efficacy reasons.

In Europe, Applicants identify in the application form for its generic/hybrid medicinal product, which is the same as an ANDA or supplemental NDA (sNDA) drug product, the reference medicinal product (product name, strength, pharmaceutical form, MAH, first authorization, Member State/Community), which is synonymous with a RLD, as follows:

1. The medicinal product that is or has been authorized in the EEA, used as the basis for demonstrating that the data protection period defined in the European pharmaceutical legislation has expired. This reference medicinal product, identified for the purpose of calculating expiry of the period of data protection, may be for a different strength, pharmaceutical form, administration route or presentation than the generic/hybrid medicinal product.

2. The medicinal product, the dossier of which is cross-referred to in the generic/hybrid application (product name, strength, pharmaceutical form, MAH, marketing authorization number). This reference medicinal product may have been authorized through separate procedures and under a different name than the reference medicinal product identified for the purpose of calculating expiry of the period of data protection. The product information of this reference medicinal product will, in principle, serve as the basis for the product information claimed for the generic/hybrid medicinal product.

3. The medicinal product (product name, strength, pharmaceutical form, MAH, Member State of source) used for the bioequivalence study(ies) (where applicable).

The different abbreviated approval pathways for drug products under the FD&C Act include the abbreviated approval pathways described in section 505(j) and 505(b)(2) of the FD&C Act (21 U.S.C. 3550) and 21 U.S.C. 23 355(b)(2), respectively).

According to the FDA (https://www.fda.gov/downloads/Drugs/GuidanceComplianceRegulatoryInformation/Guidances/UCM579751.pdf), the contents of which is incorporated herein by reference), NDAs and ANDAs can be divided into the following four categories:

(1) A "stand-alone NDA" is an application submitted under section 505(b)(1) and approved under section 505(c) of the FD&C Act that contains full reports of investigations of safety and effectiveness that were conducted by or for the applicant or for which the applicant has a right of reference or use.

(2) A 505(b)(2) application is an NDA submitted under section 505(b)(1) and approved under section 505(c) of the FD&C Act that contains full reports of investigations of safety and effectiveness, where at least some of the information required for approval comes from studies not conducted by or for the applicant and for which the applicant has not obtained a right of reference or use.

(3) An ANDA is an application for a duplicate of a previously approved drug product that was submitted and approved under section 505(j) of the FD&C Act. An ANDA relies on FDA's finding that the previously approved drug product. i.e., the reference listed drug (RLD), is safe and effective. An ANDA generally must contain information to show that the proposed generic product (a) is the same as the RLD with respect to the active ingredient(s), conditions of use, route of administration, dosage form, strength, and labeling (with certain permissible differences) and (b) is bioequivalent to the RLD. An ANDA may not be submitted if studies are necessary to establish the safety and effectiveness of the proposed product.

(4) A petitioned ANDA is a type of ANDA for a drug product that differs from the RLD in its dosage form, route of administration, strength, or active ingredient (in a product with more than one active ingredient) and for which FDA has determined, in response to a petition submitted under section 505(j)(2)(C) of the FD&C Act (suitability petition), that studies are not necessary to establish the safety and effectiveness of the proposed drug product.

A scientific premise underlying the Hatch-Waxman Amendments is that a drug product approved in an ANDA under section 505(j) of the FD&C Act is presumed to be therapeutically equivalent to its RLD. Products classified as therapeutically equivalent can be substituted with the full expectation that the substituted product will produce the same clinical effect and safety profile as the prescribed product when administered to patients under the conditions specified in the labeling. In contrast to an ANDA, a 505(b)(2) application allows greater flexibility as to the characteristics of the proposed product. A 505(b)(2) application will not necessarily be rated therapeutically equivalent to the listed drug it references upon approval.

The term "therapeutically equivalent to a reference listed drug" means that the drug product is a generic equivalent. i.e., pharmaceutical equivalents, of the reference listed drug product and, as such, is rated an AB therapeutic equivalent to the reference listed drug product by the FDA whereby actual or potential bioequivalence problems have been resolved with adequate in vivo and/or in vitro evidence supporting bioequivalence.

"Pharmaceutical equivalents" means drug products in identical dosage forms and route(s) of administration that contain identical amounts of the identical active drug ingredient as the reference listed drug.

FDA classifies as therapeutically equivalent those products that meet the following general criteria: (1) they are approved as safe and effective; (2) they are pharmaceutical equivalents in that they (a) contain identical amounts of the same active drug ingredient in the same dosage form and route of administration, and (b) meet compendial or other applicable standards of strength, quality, purity, and identity; (3) they are bioequivalent in that (a) they do not present a known or potential bioequivalence problem, and they meet an acceptable in vitro standard, or (b) if they do present such a known or potential problem, they are shown to meet an appropriate bioequivalence standard; (4) they are adequately labeled; and (5) they am manufactured in compliance with Current Good Manufacturing Practice regulations The term "bioequivalent" or "bioequivalence" is the absence of a significant difference in the rate and extent to which the active ingredient or active moiety in pharmaceutical equivalents or pharmaceutical alternatives becomes available at the site of drug action when administered at the same molar dose under similar conditions in an appropriately designed study. Section 505 (j)(8)(B) of the FD&C Act describes one set of conditions under which a test and reference listed drug shall be considered bioequivalent; the rate and extent of absorption of the [test] drug do not show a significant difference from the rate and extent of absorption of the [reference] drug when administered at the same molar dose of the therapeutic ingredient under similar experimental conditions in either a single dose or multiple doses; or the extent of absorption of the [test] drug does not show a significant difference from the extent of absorption of the [reference] drug when administered at the same molar dose of the therapeutic ingredient under similar experimental conditions in either a single dose or multiple doses and the difference from the [reference] drug in the rate of absorption of the drug is intentional, is reflected in its proposed labeling, is not essential to the attainment of effective body drug concentrations on chronic use, and is considered medically insignificant for the drug.

Where these above methods are not applicable (e.g., for drug products that are not intended to be absorbed into the bloodstream), other scientifically valid in vivo or in vitro test methods to demonstrate bioequivalence may be appropriate.

For example, bioequivalence may sometimes be demonstrated using an in vitro bioequivalence standard, especially when such an in vitro test has been correlated with human in vivo bioavailability data. In other situations, bioequivalence may sometimes be demonstrated through comparative clinical trials or pharmacodynamic studies.

Also provided herein are pharmaceutical products comprising a clinically proven safe and clinically proven effective amount of apalutamide, wherein the pharmaceutical product is packaged and wherein the package includes a label that (a) identifies apalutamide as a regulatory approved chemical entity, and (b) instructs use of apalutamide in the treatment of metastatic castration-sensitive prostate cancer. In certain embodiments, the label provides data for improving radiographic progression-free survival and/or overall survival relative to a placebo. In certain embodiments, the label lists ischemic cardiovascular events, fractures, falls and seizure as adverse reactions. In certain embodiments, the label includes data indicating an increase in ischemic cardiovascular events, fractures, falls or seizures relative to a standard of care. In certain embodiments, the standard of care is administration of androgen deprivation therapy.

As used herein, unless otherwise noted, the term "safe" means without undue adverse side effects (such as toxicity, irritation, or allergic response), commensurate with a reasonable benefit/risk ratio when used in the manner of this invention. Similarly, unless otherwise noted, the term "effective" means the efficacy of treatment has been demonstrated for the treatment of patients with metastatic castration-sensitive prostate cancer when dosed in a therapeutically effective dose. In certain embodiments, the methods described herein are safe. In other embodiments, the methods described herein are effective. In further embodiments, the methods described herein are safe and effective. In yet other embodiments, the therapeutically effective amount of apalutamide is safe. In still further embodiments, the therapeutically effective amount of apalutamide is effective. In other embodiments, the therapeutically effective amount of apalutamide is safe and effective.

As used herein, unless otherwise noted, the term "clinically proven" (used independently or to modify the terms "safe" and/or "effective") means that proof has been proven by a phase III or IV clinical trial that is sufficient to meet approval standards of U.S. Food and Drug Administration or similar study for market authorization by EMEA. Preferably, an adequately sized, randomized, placebo-controlled, double-blinded study is used to clinically prove the effects of apalutamide. Most preferably, to clinically prove the effects of apalutamide to treat metastatic castration-sensitive prostate cancer, this would be a randomized, placebo-controlled, double-blind study of apalutamide plus androgen deprivation therapy versus androgen deprivation therapy with the patient's condition assessed by radiographic progression-free survival or overall survival. For example, proof may be provided by the clinical trial described in Example 1.

As used herein, unless otherwise noted, the term "clinically proven effective" means the efficacy of treatment has been proven by a phase III or IV clinical trial as statistically significant i.e., the results of the clinical trial are not likely to be due to chance with an alpha level less than 0.05 or the clinical efficacy results are sufficient to meet approval standards of U.S. Food and Drug Administration or similar study for market authorization by EMEA. For example, apalutamide was clinically proven effective for the treatment of patients with metastatic castration-sensitive prostate cancer when orally administered at a therapeutically effective dose of 240 mg and co-administered with androgen deprivation therapy in improving radiographic progression-free survival and overall survival relative to patients treated with placebo plus androgen deprivation therapy, and as specifically set forth in the examples.

As used herein, unless otherwise noted, the term "clinically proven safe" means the safety of treatment has been proven by a phase III or IV clinical trial by analysis of the trial data and results establishing that the treatment is without undue adverse side effects and commensurate with the statistically significant clinical benefit (e.g., efficacy) sufficient to meet approval standards of U.S. Food and Drug Administration or similar study for market authorization by Europe, the Middle East, and Africa (EMEA). For example, apalutamide was clinically proven safe for the treatment of patients with metastatic castration-sensitive prostate cancer when orally administered at a therapeutically effective dose of 240 mg and co-administered with androgen deprivation therapy, and as specifically set forth in the examples.

Methods of Sale

Provided herein are methods of selling an approved drug product comprising apalutamide, said method comprising, consisting of, or consisting essentially of selling such drug product, wherein a drug product label for a reference listed drug for such drug product includes instructions for treating metastatic castration-sensitive prostate cancer. In certain embodiments, the drug product is an ANDA drug product, a supplemental New Drug Application drug product or a 505(b)(2) drug product.

The terms "sale" or "selling" means transferring a drug product, e.g., a pharmaceutical composition or an oral dosage form, from a seller to a buyer.

Further provided herein are methods of offering for sale an approved drug product comprising apalutamide, said method comprising, consisting of, or consisting essentially of offering for sale such drug product, wherein a drug product label for a reference listed drug for such drug product includes instructions for treating metastatic castration-sensitive prostate cancer. In certain embodiments, the drug product is an ANDA drug product, a supplemental New Drug Application drug product or a 505(b)(2) drug product.

The term "offering for sale" means the proposal of a sale by a seller to a buyer for a drug product, e.g., a pharmaceutical composition and an oral dosage form.

In another aspect, described herein are methods of selling apalutamide, said method comprising, consisting of, or consisting essentially of placing apalutamide into the stream of commerce wherein said apalutamide includes a package insert that contains instructions for safely and effectively treating metastatic castration-sensitive prostate cancer using apalutamide.

In still further aspects, described herein are methods of offering for sale apalutamide, said method comprising, consisting of, or consisting essentially of offering to place the apalutamide into the stream of commerce wherein said the apalutamide includes a package insert that contains instructions for safely and effectively treating metastatic castration-sensitive prostate cancer using the apalutamide.

EXAMPLES

These examples are provided for illustrative purposes only and not to limit the scope of the claims provided herein.

Example 1: A Phase 3 Randomized, Placebo-Controlled, Double-Blind Study of Apalutamide Plus Androgen Deprivation Therapy (ADT) Versus ADT in Subjects with Metastatic Hormone-Sensitive Prostate Cancer (mCSPC)

Objectives

Primary Objective

To determine if the addition of apalutamide to androgen deprivation therapy (ADT) provides superior efficacy in improving radiographic progression-free survival (rPFS) or overall survival (OS) for subjects with mCSPC.

Secondary Objectives

To evaluate clinically relevant improvements with addition of apalutamide to ADT including delays in pain progression and opioid use for prostate cancer, skeletal-related events, and the need for cytotoxic chemotherapy;

To characterize the safety of adding apalutamide to ADT for subjects with mCSPC;

To characterize the population pharmacokinetics (PK) and pharmacodynamics (PD) of apalutamide;

To evaluate the concentration of leuprolide and assess the PD effect of leuprolide on testosterone concentrations when used alone or in combination with apalutamide;

To evaluate the treatment effectiveness with the addition of apalutamide to ADT for the subpopulations of subjects with low-volume or high-volume mCSPC.

Other Objectives

To evaluate exploratory biomarkers predictive of response and resistance to treatment;

To evaluate patient relevant outcomes including symptoms (i.e., pain, fatigue, urination) and function (i.e., physical, emotional, social) and health-related quality of life;

To evaluate improvements in other clinically relevant endpoints of apalutamide plus ADT compared with ADT alone;

To collect medical resource utilization (MRU) data that may be used in future economic modeling.

Study Design

The study described in Example 1 has been at least partially completed according to the criteria described herein and is continuing. This was a randomized, double-blind, placebo-controlled, multinational, and multicenter Phase 3 study to determine if subjects with mCSPC benefited from the addition of apalutamide to ADT. The data presented herein as associated with this study reflects the state of this study at the time of this filing. The study was conducted at 260 sites in 23 countries. Review boards at all participating institutions approved the study, which was conducted in accordance with current International Conference on Harmonization guidelines for Good Clinical Practice and according to Declaration of Helsinki principles. All patients provided written informed consent. An independent data-monitoring committee was commissioned by the sponsor to monitor safety and efficacy before unblinding and make study conduct recommendations. Data were transcribed by personnel at each site from source documents into sponsor-prepared electronic case report forms. Blinding of investigators, patients, study site personnel, and sponsor study team to randomization codes was maintained until study completion, independent data-monitoring committee recommendation, or individual patient medical need.

Enrollment of approximately 1,000 subjects was planned for this study. Subjects who met all of the inclusion criteria and none of the exclusion criteria were stratified by Gleason score at diagnosis (≤7 versus >7), region (North America [NA] and European Union [EU] versus Other Countries), and prior docetaxel use (yes versus no).

Patients were randomized 1:1 to receive apalutamide (240 mg) or matched placebo administered orally once daily, in addition to continuous ADT. Patients were stratified by Gleason score at diagnosis (≤7 vs. >7), region (North America and European Union vs. all other countries), and prior treatment with docetaxel (yes vs. no). A Screening Phase of up to 28 days before randomization established study eligibility. Subjects will receive/received treatment in 28-day cycles during the Treatment Phase until disease progression or the occurrence of unacceptable treatment-related toxicity or the sponsor terminates the study. If the subject has/had radiographic progression without clinical progression and alternate therapy is/was not initiated, treatment may continue until clinical progression is observed; subjects must discontinue study drug with documented clinical progression based on protocol-specified criteria. After discontinuation of study drug, subjects will have an End-of-Treatment Visit within 30 days after the last dose of study drug. During the Follow-up Phase, data collection (every 4 months) will include survival, additional data on secondary endpoints, date and type of disease progression (radiographic, PSA, clinical or a combination) on the first subsequent therapy for prostate cancer, and subsequent therapy for prostate cancer. Data collection in follow-up will continue until the subject dies, withdraws consent, is lost to follow-up or the study is terminated by the sponsor. The Brief Pain Inventory Short Form (BPI SF), Brief Fatigue Inventory (BFI), and EQ-5D-51, patient-report outcome (PRO) measures will also continue in the Follow-up Phase up to 12 months after treatment discontinuation. In the event of a positive study result at either of the interim analyses or at the final analysis, all subjects in the Treatment Phase will have the opportunity to enroll in an Open-label Extension Phase, which will allow subjects to receive active drug (apalutamide) for approximately 3 years.

Subjects were/will be monitored for safety starting from the signing of informed consent until 30 days after the last dose of study drug. Adverse events (AEs) including laboratory AEs will be graded and summarized using National Cancer Institute-Common Terminology Criteria for Adverse Events (NCI-CTCAE; Version 4.03). Dose modifications will be/were made according to dose modification rules outlined in the protocol.

A diagram of the study design is provided in FIG. 1.

Study Population

Each potential subject satisfied all of the following criteria to be enrolled in the study:

Overview of Patient Eligibility

Eligible patients were required to have documented adenocarcinoma of the prostate and distant metastatic disease documented by ≥1 lesion on bone scan, with or without visceral or lymph node involvement. All patients had Eastern Cooperative Oncology Group performance status (a 5-point scale where higher numbers reflect greater disability) of 0 or 1. Patients were castration sensitive (i.e., patients who are not receiving ADT at the time of progression). Previous treatment for prostate cancer was limited to prior docetaxel (maximum six cycles, no evidence of progression during treatment or before randomization), ADT for ≤6 months for metastatic castration-sensitive prostate cancer or ≤3 years total duration for localized prostate cancer, one course of radiation or surgical therapy for symptoms associated with metastatic disease, and other localized treatments (e.g., radiation therapy, postatectomy) completed ≥1 year before randomization. Patients who had received a gonadotropin-releasing hormone agonist ≤28 days before randomization were required to take a first-generation antiandrogen (i.e., biclutamide, flutamide, or nilutamide) for ≥14 days before randomization. Antiandrogen must have been discontinued before randomization. Patients with severe angina, myocardial infarction, congestive heart failure, arterial/venous thromboembolic events, history of orpredisposition for seizure, or recent ventricular arrhythmias were excluded.

Inclusion Criteria

Subject must be a man ≥18 years of age (or the legal age of consent in the jurisdiction in which the study is taking place);

Diagnosis of prostate adenocarcinoma as confirmed by the investigator;

Distant metastatic disease documented by ≥1 bone lesion(s) on Technetium-99m (99mTc) bone scan, with or without visceral or lymph node involvement. Subjects with a single bone lesion must have confirmation of bone metastasis by computed tomography (CT) or magnetic resonance imaging (MRI);

All patients have Eastern Cooperative Oncology Group (ECOG) PS grade of 0 or 1;

Androgen deprivation therapy (i.e., medical or surgical castration) must have been started ≥14 days prior to randomization. Subjects who start a GnRH agonist ≤28 days prior to randomization will be required to take a first-generation anti-androgen for ≥14 days prior to randomization. The anti-androgen must be discontinued prior to randomization;

Subjects were castration sensitive, and subjects who received docetaxel treatment must meet the following criteria:
  a. Received a maximum of 6 cycles of docetaxel therapy for mCSPC;
  b. Received the last dose of docetaxel ≤2 months prior to randomization;
  c. Maintained a response to docetaxel of stable disease or better, by investigator assessment of imaging and PSA, prior to randomization:

Be able to swallow whole study drug tablets;

To avoid risk of drug exposure through the ejaculate (even men with vasectomies), subjects must use a condom during sexual activity while on study drug and for 3 months following the last dose of study drug. Donation of sperm is not allowed while on study drug and for 3 months following the last dose of study drug;

Each subject must sign an informed consent form (ICF) indicating that he understands the purpose of and procedures, required for the study, and is willing to participate in the study. Subject must be willing and able to adhere to the prohibitions and restrictions specified in this protocol.

Other allowed prior treatment for mCSPC:
  a. Maximum of 1 course of radiation or surgical intervention with metastatic disease, and other localized treatments completed >1 year prior to randomization; radiation therapy for metastatic lesions must be completed prior to randomization;
  b. ≤6 months of ADT prior to randomization for mCSPC or ≤3 years total duration for localized prostate;

Allowed prior treatments for localized prostate cancer (all treatments must have been completed ≥1 year prior to randomization)
  a. ≤0.3 years total of ADT;
  b. All other forms of prior therapies including radiation therapy, prostatectomy, lymph node dissection, and systemic therapies.

Exclusion Criteria

Any potential subject who meets any of the following criteria was excluded from participating in the study.

Pathological finding consistent with small cell, ductal or neuroendocrine carcinoma of the prostate;

Known brain metastases;

Lymph nodes as only sites of metastases;

Visceral (i.e., liver or lung) metastases as only sites of metastases;

Other prior malignancy (exceptions: adequately treated basal cell or squamous cell skin cancer, superficial bladder cancer, or any other cancer in situ currently in complete remission) ≤5 years prior to randomization;

Clinical laboratory values during the Screening Phase:
  a. hemoglobin <9.0 g/dL;
  b. neutrophils <1.5×109/L;
  c. platelets <100×109/L;
  d. total bilirubin >1.5× upper limit of normal (ULN) [NOTE: in subjects with Gilbert's syndrome, if total bilirubin is >1.5×ULN, measure direct and indirect bilirubin and if direct bilirubin is <1.5×ULN, subject may be eligible];
  e. alanine aminotransferase (ALT) or aspartate aminotransferase (AST)>2.5×ULN;
  f. serum creatinine >2.0×ULN;
  g. serum albumin <3.0 g/dL.

Prior treatment with other next generation anti-androgens (e.g., enzalutamide), CYP17 inhibitors (e.g., abiraterone acetate), immunotherapy (e.g., sipuleucel-T), radiopharmaceutical agents or other treatments for prostate cancer except those listed in Inclusion Criteria;

Initiation of treatment with a bisphosphonate or denosumab for the management of bone metastasis ≤28 days prior to randomization;

Medications known to lower the seizure threshold must be discontinued or substituted ≥28 days prior to randomization;

Administration of other investigational therapeutic agents, blood product support, growth factor support or invasive surgical procedure (not including surgical castration) ≤28 days prior to randomization or currently enrolled in an investigational study;

Current or prior treatment with anti-epileptic medications for the treatment of seizures. History of seizure or condition that may predispose to seizure (including, but not limited to prior cerebrovascular accident, transient ischemic attack, or loss of consciousness within 1 year prior to randomization; brain arteriovenous malformation; or intracranial masses such as a schwannoma or meningioma that is causing edema or mass effect);

Current evidence of any of the following:
  a. Severe/unstable angina, myocardial infarction, symptomatic congestive heart failure, uncontrolled hypertension, clinically significant arterial or venous thromboembolic events (e.g., pulmonary embolism), or clinically significant ventricular arrhythmias ≤6 months prior to randomization;
  b. Gastrointestinal disorder affecting absorption;
  c. Active infection requiring systemic therapy such as human immunodeficiency virus (HIV);
  d. Active or symptomatic viral hepatitis or chronic liver disease; ascites or bleeding disorders secondary to hepatic dysfunction;

Subject has known allergies, hypersensitivity, or intolerance to apalutamide or its excipients Any condition or situation that in the opinion of the investigator, would preclude participation in this study.

Treatment Allocation

Procedures for Stratification and Randomization

Subjects were stratified by Gleason score at diagnosis (≤7 versus >7), region (North America [NA] and European Union [EU] versus Other Countries), and prior docetaxel use (Yes versus No). Subjects were randomly assigned to the active or control group in a 1:1 ratio. The randomization was balanced by using randomly permuted blocks. The interactive web response system (IWRS) assigned a unique treatment code, which dictated the treatment assignment and matching study drug kit for the subject. The requestor sued his own user identification and personal identification number when contacting the IWRS, and then gave the relevant subject details to uniquely identify the subject.

Dosage and Administration

Apalutamide Administration

Apalutamide was administered on a continual basis, but for the purpose of scheduling the study assessments and treatment compliance, a treatment cycle is defined as 28 days. Subjects were randomly assigned in a 1:1 ratio to receive either apalutamide or matching placebo:

Apalutamide 240-mg (4×60-mg tablets); taken orally once daily with or without food or Placebo (4 tablets); taken orally once daily with or without food.

If a dose of apalutamide (or placebo) was missed it was omitted and was not be made up or taken with the next dose the following day.

ADT Administration

All subjects who did not undergo surgical castration, received and remained on a stable regimen of ADT. The choice of the GnRHa (agonist or antagonist) was at discretion of the Investigator. Dosing (dose and frequency of administration) was consistent with the prescribing information.

Toxicity and Rash Management

Table 1 summarizes apalutamide/placebo dose modifications for drug-related toxicities. Dose modifications may also be provided for drug-related rashes. Once the dose was reduced for drug-related toxicities, a re-escalation of the dose was discussed with the sponsor.

TABLE 1

Dose Modifications of Apalutamide/Placebo

| Severity | Number of apalutamide/placebo tablets |
| --- | --- |
| Grade 1 or 2 | No change or hold until return to baseline |
| ≥Grade 3 | Hold until Grade 1 or baseline, resume at full dose |
| Recurrence ≥Grade 3 | Hold until Grade 1 or baseline; 2 dose reductions are allowed for recurrent treatment-related toxicity (180 mg [3 tablets]) and 120 mg [2 tablets]). Discontinue if toxicity persists after 2 dose reductions. |
| First occurrence of seizure of any grade or Grade 4 neurotoxicity | Discontinue |

Note:
Adverse events are graded according to NCI-CTCAE Version 4.03

If the skin rash has any component of desquamation, mucosal involvement, or pustules, stop dosing with apalutamide/placebo, the subject was/will be referred to dermatology for evaluation, and a skin biopsy is recommended (in addition to the dose modifications). If the skin rash is Grade 3 or higher, the subject may be asked to consent to documentation by a photograph and further evaluation by a dermatologist.

Prestudy and Concomitant Therapy

Permitted Supportive Care Therapies

Supportive care medications are permitted with their use following institutional guidelines. The following supportive care therapies are considered permissible during the study:

Intermittent short course of opioid analgesics is allowed for pain control;

Surgical interventions and procedures such as transurethral resection of the prostate (TURP) and placement of ureteral stents for the management of complications due to local progression;

Bisphosphonates and denosumab for management of bone-related metastasis should be used according to their market authorized approved label. Subjects should be either on a stable dose of such agents for ≥28 days prior to randomization or agree not to initiate such therapy until radiographic progression is documented. Bisphosphonates and denosumab at doses for prevention of osteoporosis are allowed;

Conventional multivitamins, selenium and soy supplements;

Transfusions and hematopoietic growth factors per institutional practice guidelines (Note that blood product support and growth factor support are not allowed in the period of ≤28 days prior to randomization);

Immunoglobulin therapy for non-cancer-related treatment per institutional practice guidelines.

Prohibited Concomitant Therapies

As a class effect, AR antagonists have been associated with seizures due to an off-target mechanism of action (gamma amino butyric acid chloride channel [GABAA] inhibition). Drugs known to lower the seizure threshold or cause seizures are prohibited and a representative list is included below:

Atypical antipsychotics (e.g. clozapine, olanzapine, risperidone, ziprasidone);

Bupropion;

Lithium;

Meperidine (pethidine);

Phenothiazine antipsychotics (e.g., chlorpromazine, mesoridazine, thioridazine);

Tricyclic antidepressants (e.g., amitriptyline, desipramine, doxepin, imipramine, maprotiline, mirtazapine);

Aminophylline/theophylline;

Other prohibited therapies include the following:

Investigational agents;

Abiraterone acetate or other CYP17 inhibitor,

Other hormonal agents for the treatment of prostate cancer;

Other antineoplastic agents;

Radiation therapy for new painful metastatic prostate cancer lesions that were not present on baseline imaging;

5-α-reductase inhibitors;

Chemotherapy;

Immunotherapy or vaccine therapy for cancer treatment;

Other anti-androgens (e.g., bicalutamide, nilutamide, flutamide, cyproterone acetate, enzalutamide);

Bisphosphonates or denosumab for management of bone metastasis unless such therapy was started >28 days prior to randomization and subjects have been on a stable dose. Bisphosphonate or denosumab at doses for osteoporosis prophylaxis is allowed;

Systemic ketoconazole (or other azole drugs such as fluconazole or itraconazole);

Diethylstilbestrol (DES) or similar;

Other preparations such as pomegranates or pomegranate juice or saw palmetto, which are thought to have endocrine effects on prostate cancer;

Radiopharmaceuticals such as strontium (89Sr) or samarium (153Sm) or similar analogs such as radium-223 (223Ra);

Spironolactone.

Restricted Concomitant Medications

Highlights of drug interaction are summarized below.

Strong CYP3A4 inducers: the potential for drug-drug interactions with apalutamide has not been tested clinically. Strong inducers of CYP3A4 (e.g., phenytoin, carbamazepine, rifampin, rifabutin, rifapentine, phenobarbital, efavirenz, tipranavir, St. John's wort) should be avoided as much as possible;

Apalutamide may also induce CYP3A4; therefore, caution should be taken when administered in conjunction with CYP3A4 substrates that have a narrow therapeutic index;

Strong CYP2C8 inhibitors (e.g., gemfibrozil) should be used with caution with apalutamide;

Long-term use of systemically administered corticosteroids during the study is not allowed. Short-term use (≤4 weeks, including taper) and locally administered steroids (e.g., inhaled, topical, ophthalmic, and intraarticular) are allowed, if clinically indicated.

Efficacy Evaluations/Endpoints

Radiographic progression was/will be assessed by soft tissue lesion by computed tomography (CT)/magnetic resonance imaging (MRI) per modified Response Evaluation Criteria in Solid Tumors (RECIST 1.1) or by bone lesion progression on bone scans. Survival data was/will be collected throughout the Treatment Phase and during the Follow-up Phase.

Evaluations

Patients were assessed for efficacy per modified Response Evaluation Criteria in Solid Tumors version 1.1 using computed tomography or magnetic resonance imaging of chest, abdomen, and pelvis during screening (≤6 weeks before randomization) and Prostate Cancer Working Group 2 criteria using bone scan during cycles 3 and 5, and every fourth cycle thereafter. Progression events were assessed by investigator. Scans from ~60% of patients were randomly selected for independent central review. Adverse events were assessed monthly and graded per National Cancer Institute Common Terminology Criteria for Adverse Events Version 4.0.3. FACT-P assessments were collected day 1 of cycles 2-7, then every other cycle, end of treatment, and every 4 months for up to 1 year after discontinuation. BPI-SF assessments were collected 6 days before cycle 1, then at each cycle, end of treatment, and every 4 months for up to 1 year after discontinuation.

More specifically, the efficacy evaluations include the following:

Tumor measurements (CT or MRI [abdomen, chest, and pelvis], 99mTc bone scans). The same imaging modality for tumor assessments should be used throughout the evaluation of an individual subject. Unscheduled tumor assessment and appropriate imaging should be considered if signs or symptoms suggestive of disease progression, including escalating pain not attributed to another cause, worsening ECOG PS status grade, or physical examination findings consistent with disease progression, are recorded;

Scans from approximately 60% of patients were randomly selected for independent central review;

Serum PSA evaluations (performed at a central laboratory);

Skeletal-related event (SRE) is defined as the occurrence of symptomatic pathological fracture, spinal cord compression, radiation to bone, or surgery to bone;

Pain progression is defined as an increase by 2 points from baseline in the BPI-SF questionnaire worst pain intensity (item 3) observed at 2 consecutive evaluations ≥4 weeks apart; with an average worst pain score of >4 in subjects who have had no decrease in opioids or initiation of chronic opioids, whichever occurs first.

Patient-Reported Outcomes

Patient-reported outcomes include administration of various questionnaires including the Brief Pain Index-Short Form (BPI-SF), the Analgesic Use Log, the Brief Fatigue Inventory (BFI), the Functional Assessment of Cancer Therapy-Prostate (FACT-P) and the EQ-5D-5L (a standardized measure of health status developed by the EuroQoL Group to provide a simple, generic measure of health for clinical and economic appraisal (EuroQoL Group, 1990)). Patient reported outcome questionnaires were/will be collected throughout the study as well as during the Follow-up Phase (up to 12 months after treatment discontinuation) and the Open-label Extension Phase.

Tumor Response Criteria

Tumor response was assessed utilizing imaging measurements, as defined by Response Evaluation Criteria in Solid Tumors (RECIST 1.1). In this study, RECIST was modified based on Prostate Cancer Working Group 2 (PCWG2) criteria, which are specific for this patient population. Prostate specific antigen measurements were evaluated according to PCWG2 criteria. Evaluation of rPFS was assessed by the investigator.

Patients in the embodied study were assessed for efficacy per modified Response Evaluation Criteria In Solid Tumors version 1.1 and Prostate Cancer Working Group 2 criteria. 2 Prostate Cancer Working Group 2 criteria for progression are as follows:

PSA: first ≥25% increase from baseline and ≥2 ng/mL above the nadir (confirmed by second value 3 or more weeks later)

Soft-tissue lesions: follow Response Evaluation Criteria in Solid Tumors with caveats Imaging should include a computed tomography scan or magnetic resonance imaging at a minimum; centers with relevant expertise should utilize endorectal magnetic resonance imaging or transrectal ultrasound Only report changes in lymph nodes that were ≥2 cm in diameter at baseline Record changes in nodal and visceral soft tissue sites separately Record complete elimination of disease at any site separately Confirm favorable change with a second scan Record changes using a waterfall plot Progression at first assessment must be confirmed by a second scan ≥6 weeks later Bone: appearance of ≥22 new lesions, and, for the first reassessment only, a confirmatory scan performed ≥6 weeks later indicating a minimum of ≥2 new lesions.

Endpoints

Dual-Primary Endpoints

The dual-primary endpoints were radiographic progression-free survival (rPFS) and overall survival (OS).

Secondary Endpoints

Secondary end points were time to cytotoxic chemotherapy, time to pain progression as assessed by Brief Pain Inventory Short Form (BPI-SF; worst pain [item 3] was used for the time to pain progression end point; scores range 0 to 10, with lower scores representing lower levels of pain intensity, a change of 2 was the minimally important difference), time to chronic opioid use, and time to skeletal-related event. Prespecified subgroup analysis based on data from patients with low- or high-volume metastatic castration-sensitive prostate cancer was planned, and evaluation of treatment outcomes in these groups was a secondary objective. High-volume disease definition was as adapted from Sweeney C J, Chen Y H, Carducci M, et al. Chemohormonal therapy in metastatic hormone-sensitive prostate cancer. N Engl J Med 2015; 373:737-46 as follows 1) visceral metastases and ≥1 bone lesion, or 2) ≥4 bone lesions, with ≥1 outside of the axial skeleton. Low-volume disease was defined as presence of bone lesions not meeting high-volume disease definition.

Exploratory Endpoints

Exploratory end points included time to prostate-specific antigen (PSA) progression, second progression-free survival, and time to symptomatic local progression. Time to second progression-free survival was defined as time from randomization to first occurrence of investigator-determined disease progression (PSA progression, progression on imaging, or clinical progression) while patient was receiving first subsequent therapy for prostate cancer, or death due to any cause, whichever occurs first. Patient-reported outcomes for health-related quality of life were assessed by Functional Assessment of Cancer Therapy-Prostate (FACT-P) questionnaire. Raw FACT-P scores range from 0 to 156, with higher scores indicating more favorable health-related quality of life. A 6- to 10-point change in FACT-P total score is the minimally important difference.

Population Pharmacokinetic Evaluations

Trough PK samples were/will be collected. Pre-dose blood samples for analysis of apalutamide and active metabolite (JNJ-56142060) concentrations was/will be collected on Day 1 of Cycles 2, 3, 4, 5, and 6.

Leuprolide PK Sub-Study

Optional PK samples were/will be collected from at least 60 consenting subjects (in selected countries) who received or will receive leuprolide acetate as the GnRHa at the time of randomization. Samples were/will be collected on Day 1 of Cycles 1, 3, 4, 5, and 6 for analysis of leuprolide and testosterone concentrations.

Biomarker Evaluations

Plasma-based circulating DNA was/will be used to assess the presence of the androgen receptor (AR) F876L mutation and whole blood or plasma DNA to assess other markers that may be associated with resistance to apalutamide. Archival formalin fixed paraffin embedded (FFPE) tumor blocks or tumor slides was/will be collected to evaluate mRNA expression of genes representing AR signaling to compare biology of high- and low volume disease with outcome and to evaluate expression of immune markers such as OX40, GITR, and FOXP3.

Safety Evaluations

Safety evaluations include AEs, vital signs measurements (blood pressure), physical examinations, ECOG PS, and clinical laboratory tests including but not limited to a hematology panel, serum chemistry panel, liver function test, and fasting lipid panel. In the event of additional safety monitoring, unscheduled laboratory assessments was/will be performed as required. Vital signs and Eastern Cooperative Oncology Group performance status were evaluated at screening and at every scheduled visit during treatment. Safety was assessed continuously, and adverse events were graded according to National Cancer Institute Common Terminology Criteria for Adverse Events Version 4.0.3. FACT-P assessments were collected on day 1 of cycles 1 through 7, then every other cycle, at end of treatment, and once every 4 months for up to 1 year after discontinuation Electrocardiogram (ECG)

Electrocardiograms (ECGs) (12 lead) was recorded at screening.

Vital Signs

Body temperature, heart rate, respiratory rate, and blood pressure were recorded at screening. At all other visits, only blood pressure will be measured.

Physical Examination

The screening physical examination included, at a minimum, the general appearance of the subject, height, weight, examination of the skin, ears, nose, throat, lungs, heart, abdomen, extremities, musculoskeletal system, lymphatic system, and nervous system. During the Treatment Phase and at the EOT Visit, limited symptom-directed physical examination and weight assessment were required.

Eastern Cooperative Oncology Group (ECOG) PS

When scheduled, ECOG PS assessments as with PRO questionnaires was obtained prior to any other study procedures planned for the same day.

Subject Completion/Withdrawal

Completion

A subject will be considered to have completed the study if he has died before the end of the study or has not been lost to follow-up or withdrawn consent before the end of the study.

Discontinuation of Apalutamide

If a subject's study drug must be discontinued before disease progression this will not result in automatic withdrawal of the subject from the study. If the subject has radiographic progression without clinical progression and alternate therapy is not initiated, treatment may continue until clinical progression is observed. All attempts should be made to capture radiographic progression even in subjects who have evidence of clinical progression.

However, a subject's study treatment must be discontinued for:

Clinical progression defined as:
  Deterioration in ECOG PS grade to grade 3 or higher (related to prostate cancer progression)
  Need to initiate any of the following because of tumor progression (even in the absence of radiographic evidence of disease)
    Subsequent anti-cancer therapy for metastatic prostate cancer
    Radiation therapy for metastatic prostate cancer lesion(s) (palliative radiation to lesions existing at baseline will not be considered clinical progression)
    Surgical interventions for complications due to metastatic prostate cancer progression.
  Need for chronic opioid analgesics: For subjects entering the study without receiving opioids, chronic opioid use is defined as administration of opioid analgesics lasting for ≥3 weeks for oral or ≥7 days for non-oral formulations. For subjects entering the study already receiving opioids, chronic opioid use is defined as a ≥30% increase in total daily dose of the opioid analgesics lasting for ≥3 weeks for oral or ≥7 days for non-oral formulations.

More than 2 dose level reductions for Grade 3 or higher treatment-related AEs (Table 1)

Seizure of any grade or Grade 4 neurotoxicity

Subjects who have had their treatment assignment unblinded for any reason except for IDMC recommendation to unblind the study The investigator believes that for safety reasons (e.g., AE) it is in the best interest of the subject to discontinue study treatment All attempts to obtain imaging studies at the time of treatment discontinuation or EOT Visit should be made to assess for radiographic progression. Study drug was/will be continued for subjects who have increasing PSA values in the absence of radiographic or clinical progression. Although serial PSA measurements were performed in this study, progression or change in PSA values were not used as the lone indicator for disease progression or treatment discontinuation. If a subject discontinues study drug, but does not withdraw consent for follow-up, scheduled assessments should continue according to the Follow-up Phase in the Time and Events Schedule.

Statistical Methods

Overview

The clinical trial exemplified herein was designed to enroll ≈1,000 patients. Radiographic progression-free survival was tested first. If it was statistically significant, its alpha was recycled to overall survival based on the fallback method. An overall 5% type I error was planned. 368 imaging progression-free survival events were required to provide at least 85% power to detect a hazard ratio of 0.67 with two-tailed significance level 0.005. For final overall survival analysis, 410 deaths were required to provide ≈80% power to detect a hazard ratio of 0.75 with a two-tailed significance level of 0.045. Overall survival analysis incorporated group sequential design with an alpha spending function that was calculated as Wang-Tsiatis power boundaries of shape parameter 0.2. Two interim analyses were planned for overall survival. It was estimated that first interim analysis would include ≈50% of total required events for overall survival at the time of primary analysis for radiographic progression-free survival. Alpha level for interim analysis for overall survival was 0.009, assuming overall two-tailed significance level 0.045. Subgroup analyses were prespecified to assess consistency of treatment effect. If dual primary end points were statistically significant, evaluation of secondary end points was to be performed in the following hierarchical order, each with overall two-sided significance level of α=0.05: 1) time to cytotoxic chemotherapy, 2) time to pain progression, 3) time to chronic opioid use, 4) time to skeletal-related event. Demographic and baseline characteristics were summarized using descriptive statistics. Primary statistical method of comparison for time-to-event end points was stratified log-rank test, according to stratification factors. Kaplan-Meier product limit method and Cox proportional hazards model were used to estimate time-to-event variables and determine hazard ratios and associated confidence intervals.

Analysis Populations

The primary analysis population uses the intent-to-treat (ITT) population, which includes all randomized subjects. The ITT population was used for the analysis of subject disposition and efficacy. The safety population includes all subjects who received at least 1 dose of study drug as treated.

Sample Size Determination

An overall type I error of 5% is planned for this study. This study utilizes the co-primary endpoints of rPFS and OS with a 0.005 level of significance allocated for the rPFS endpoint and 0.045 is allocated for OS. The study is considered a success if at least one of the co-primary endpoints is statistically significant.

The fallback method was used to recycle the alpha level for radiographic progression-free survival to overall survival if radiographic progression-free survival was statistically significant. It was estimated that ≈50% (205) of total required events for overall survival analysis would have been observed at primary analysis for radiographic progression-free survival. The alpha level for the interim analysis for overall survival was 0.009, assuming overall two-tailed significance level of 0.045. Additional subgroup analysis of patients with low- or high-volume disease at overall survival analysis was allowed without assigned alpha spending. If the dual primary end points overall survival and radiographic progression-free survival were statistically significant, evaluation of secondary end points was to be performed in the following hierarchical order, each at an overall two-sided significance level of α=0.05: 1) time to initiation of cytotoxic chemotherapy, 2) time to pain progression, 3) time to chronic opioid use, 4) time to skeletal-related event. Demographic and baseline characteristics were summarized using descriptive statistics. Kaplan-Meier product limit method and Cox proportional hazards model were used to estimate time-to-event variables and determine hazard ratios and associated confidence intervals. For radiographic progression-free analyses, patients without evidence of radiographic progression or death or those who withdrew from study or received a new subsequent anticancer therapy without documented disease progression were censored on the date of last tumor assessment, and patients without postbaseline tumor assessment were censored on date of randomization It is estimated that approximately 368 rPFS events would be required to provide at least 85% power in detecting a hazard ratio (HR) of 0.67 (median rPFS of 20 months for the control group [ADT] versus 30 months for the treatment group of apalutamide plus ADT) at a 2-tailed significance level of 0.005. The study will also provide sufficient power (approximately 80%) to detect a HR of 0.75 in the co primary endpoint of OS based on an assumed median OS of 44 months for the control group (ADT). Approximately 410 death events will be required to detect the assumed HR at a 2-tailed significance level of 0.045 with an enrollment duration of approximately 30 months (approximately 1,000 subjects). The total study duration will be approximately 54 months to obtain 410 deaths.

Efficacy Analysis

Kaplan Meier product limit method and Cox proportional hazards model will be used to estimate the time-to-event variables and to obtain the HR along with the associated confidence intervals.

Interim Analysis

For the co-primary OS endpoint, 2 interim analyses are planned for this study after observing approximately 60% (~246 events) and approximately 75% (~308 events) of the total number of required (410) events. The timing of the first interim analysis of OS may occur at the same time as the primary analysis of rPFS. However, this analysis may be performed at a different time if the number of death events needed for a valid interim analysis of OS would require an extended delay in the analysis of the rPFS endpoint. No interim analysis is planned for the rPFS endpoint.

Population PK and PD Analysis

Population PK analysis of plasma concentration-time data of apalutamide will be performed using nonlinear mixed-effects modeling. If sufficient data are available, the relationship of exposure to apalutamide and active metabolite (JNJ-56142060) to measures of efficacy and AEs may also be analyzed.

Leuprolide PK Analysis

Descriptive statistics of leuprolide PK data will be summarized by treatment groups (with apalutamide or placebo) and dose of leuprolide acetate. Statistical analysis to compare leuprolide concentrations when administered alone or in combination with apalutamide will be performed. The percentage of subjects with testosterone levels <50 ng/dL will be summarized descriptively by treatment groups.

Biomarker Analysis

The associations of the biomarkers with clinical response or time-to-event endpoints may be assessed using appropriate statistical methods (such as analysis of variance [ANOVA], categorical, or survival models), depending on the endpoint.

Safety Analysis

The safety parameters to be evaluated are the incidence and intensity of treatment-emergent AEs, clinically significant changes in the subject's physical examination findings, vital signs measurements, and clinical laboratory results. Exposure to study drug and reasons for discontinuation of study treatment will be tabulated.

Results

Overview

Five-hundred and twenty-five (525) patients were randomized to apalutamide plus ADT and 527 to placebo plus ADT. Median age was 68 years; 8% had prior treatment for localized disease; 11% had prior docetaxel; 63% had high- and 37% had low-volume disease. At the first interim analysis, with a median of 22.7 months' follow-up, apalutamide significantly improved radiographic progression-free survival (hazard ratio [HR], 0.48; 95% confidence interval [CI], 0.39 to 0.60; P<0.0001), with a 52% reduction in risk of radiographic progression or death. Overall survival also improved with apalutamide, with 33% reduction in risk of death (HR, 0.67:95% CI, 0.51 to 0.89; P=0.0053). Rates of grade 3/4 adverse events were not different between apalutamide and placebo groups. The independent data-monitoring committee recommended unblinding to allow patients receiving placebo to cross over to apalutamide. The addition of apalutamide to ADT significantly improved overall survival and radiographic progression-free survival for patients with metastatic castration-sensitive prostate cancer and had a side effect profile not different from the placebo plus ADT group.

Patients

Five-hundred and twenty-five (525) patients were randomized to apalutamide and 527 to placebo (FIG. 1). At cutoff for the first prespecified interim analysis and after 83 and 117 deaths in the apalutamide and placebo groups, respectively, median follow-up time was 22.7 months. Median number of cycles received was 23 for apalutamide and 19 for placebo (range, 1 to 37 in each group). Median treatment duration was 20.5 months for apalutamide and 18.3 months for placebo. 66% and 46% of patients in the apalutamide and placebo groups, respectively, remained on treatment clinical cutoff. A total of 45 patients across groups withdrew consent for study treatment. These patients were followed for survival and secondary end points, so their data were not missing. A total of 39 patients were either lost to follow-up or withdrew from further data collection; this information is not otherwise captured in FIG. 1.

Demographics and baseline disease characteristics were well balanced (Table 2). Patients had de novo metastatic castration-sensitive prostate cancer or relapsed metastatic disease after initial diagnosis of localized disease; most had de novo metastatic disease. Prior therapies for prostate cancer are listed in Table 3.

TABLE 2

Demographics and Baseline Disease Characteristics

| | Apalutamide (n = 525) | Placebo (n = 527) |
|---|---|---|
| Age, median - yr (range) | 69 (45-94) | 68 (43-90) |
| Age (yr) - no. (%) | | |
| <65 | 149 (28.4) | 182 (34.5) |
| 65 to 69 | 136 (25.9) | 108 (20.5) |
| 70 to 74 | 107 (20.4) | 124 (23.5) |
| ≥75 | 133 (25.3) | 113 (21.4) |
| Race - no. (%) | | |
| White | 354 (67.4) | 365 (69.3) |
| Asian | 119 (22.7) | 110 (20.9) |
| Black or African American | 10 (1.9) | 9 (1.7) |
| American Indian or Alaska native | 6 (1.1) | 13 (2.5) |
| Not reported | 11 (2.1) | 8 (1.5) |
| Other | 24 (4.6) | 22 (4.2) |
| Multiple | 1 (0.2) | 0 |
| ECOG PS score - no. (%) | n = 525 | n = 527 |
| 0 | 328 (62.5) | 348 (66.0) |
| 1 | 197 (37.5) | 178 (33.8) |
| 2 | 0 | 1 (0.2) |
| Gleason score at initial diagnosis - no. (%) | n = 525 | n = 527 |
| <7 | 41 (7.8) | 39 (7.4) |
| 7 | 133 (25.3) | 130 (24.7) |
| >7 | 351 (66.9) | 358 (67.9) |
| Tumor, lymph node, metastatic stage at initial diagnosis - no. (%) | n = 525 | n = 527 |
| T0 | 1 (0.2) | 0 |
| T1 | 41 (7.8) | 27 (5.1) |
| T2 | 146 (27.8) | 110 (20.9) |
| T3 | 210 (40.0) | 225 (42.7) |
| T4 | 76 (14.5) | 105 (19.9) |
| TX | 51 (9.7) | 60 (11.4) |
| N0 | 212 (40.4) | 216 (41.0) |
| N1 | 199 (37.9) | 184 (34.9) |
| NX | 114 (21.7) | 127 (24.1) |
| M0 | 85 (16.2) | 59 (11.2) |
| M1 | 411 (78.3) | 441 (83.7) |
| MX | 29 (5.5) | 27 (5.1) |
| Disease volume - no. (%) | | |
| Low | 200 (38.1) | 192 (36.4) |
| High | 325 (61.9) | 335 (63.6) |
| Extent of disease at study entry - no. (%) | | |
| Bone | 525 (100.0) | 527 (100.0) |
| Bone only | 289 (55.0) | 269 (51.0) |
| Lymph node | 199 (37.9) | 219 (41.6) |
| Visceral and bone | 56 (10.7) | 72 (13.7) |
| Lung | 47 (9.0) | 64 (12.1) |
| Liver | 12 (2.3) | 13 (2.5) |
| Soft tissue and bone | 22 (4.2) | 27 (5.1) |
| Median time from initial diagnosis to randomization (range) - mo | 4.1 (0.5-222.9) | 4.0 (0.7-341.4) |
| Prior docetaxel - no. (%) | | |
| Yes* | 58 (11.0) | 55 (10.4) |
| No | 467 (89.0) | 472 (89.6) |
| Median no. of cycles of | 6 | 6 |

TABLE 2-continued

Demographics and Baseline Disease Characteristics

|  | Apalutamide (n = 525) | Placebo (n = 527) |
|---|---|---|
| docetaxel among patients with prior docetaxel | | |
| Prior therapy for localized prostate cancer - no. (%) | | |
| Prostatectomy or radiotherapy | 94 (17.9) | 79 (15.0) |
| Prostatectomy only | 26 (5.0) | 27 (5.1) |
| Radiotherapy only | 47 (9.0) | 39 (7.4) |
| Both prostatectomy & radiotherapy | 21 (4.0) | 13 (2.5) |
| Median PSA (range) - μg/L | 5.97 (0-2682) | 4.02 (0-2229) |
| Median LDH (range) - U/L | 178 (88-1248) | 179 (85-1514) |
| Median alkaline phosphatase (range) - U/L | 98 (26-5193) | 94 (32-3892) |
| Mean baseline BPI-SF pain score† - no. (%) | | |
| 0 (no pain) | 198 (37.7) | 200 (38.0) |
| 1 to 3 (mild pain) | 195 (37.1) | 207 (39.3) |
| 4 to 7 (moderate pain) | 98 (18.7) | 95 (18.0) |
| 8 to 10 (severe pain) | 12 (2.3) | 11 (2.1) |
| Median baseline FACT-P total score‡ | 113 | 113 |

ECOG PS, Eastern Cooperative Oncology Group performance status; FACT-P, Functional Assessment of Cancer Therapy-Prostate; PSA, prostate-specific antigen.
*27 patients (46.6%) in the apalutamide group and 22 patients (40.0%) in the placebo group were N1 at diagnosis.
†Scores range 0 to 10, with lower scores representing lower levels of pain intensity; a change of 2 was the minimally important difference.[1]
‡Scores range from 0 to 156, with higher scores indicating more favorable health-related quality of life. A 6- to 10-point change in FACT-P total score is the minimal important difference.

Prior therapies for prostatic cancer are listed in Table 3.

TABLE 3

Prior Prostate Cancer Therapy

|  | Apalutamide (n = 525) | Placebo (n = 527) |
|---|---|---|
| Prostatectomy or radiotherapy - no. (%) | 94 (17.9) | 79 (15.0) |
| Prostatectomy only | 26 (5.0) | 27 (5.1) |
| Radiotherapy only | 47 (9.0) | 39 (7.4) |
| Both prostatectomy and radiotherapy | 21 (4.0) | 13 (2.5) |
| Hormonal therapy - no. (%) | 525 (100) | 527 (100) |
| First-generation antiandrogen | 352 (67.0) | 361 (68.5) |
| Gonadotropin-releasing hormone agonist | 462 (88.2) | 455 (86.3) |
| Gonadotropin-releasing hormone antagonist | 56 (10.7) | 53 (10.1) |
| Bilateral orchiectomy | 33 (6.3) | 40 (7.6) |
| Docetaxel - no. (%) | 58 (11.0) | 55 (10.4) |
| Vandetanib - no. (%) | 1 (0.2) | 0 |

Dual Primary End Points

Figure 2A:
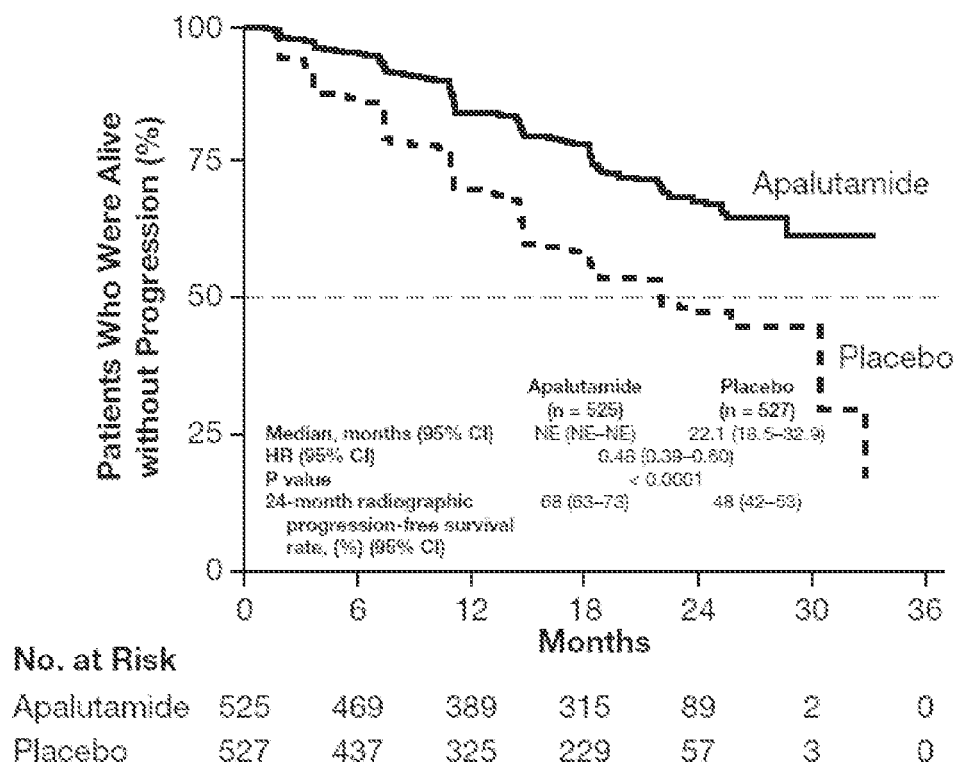
FIGS. 2A-2B illustrate Kaplan-Meier estimates of radiographic progression-free survival (FIG. 2A) and Forest Plot of Radiographic Progression-free Survival by Baseline Patient Characteristics (FIG. 28). Analyses were performed using a log-rank test with stratification by Gleason score at diagnosis (≤7 vs. >7), region (North America and European Union vs. all other countries), and prior treatment with docetaxel (yes vs. no).
Figure 2B:
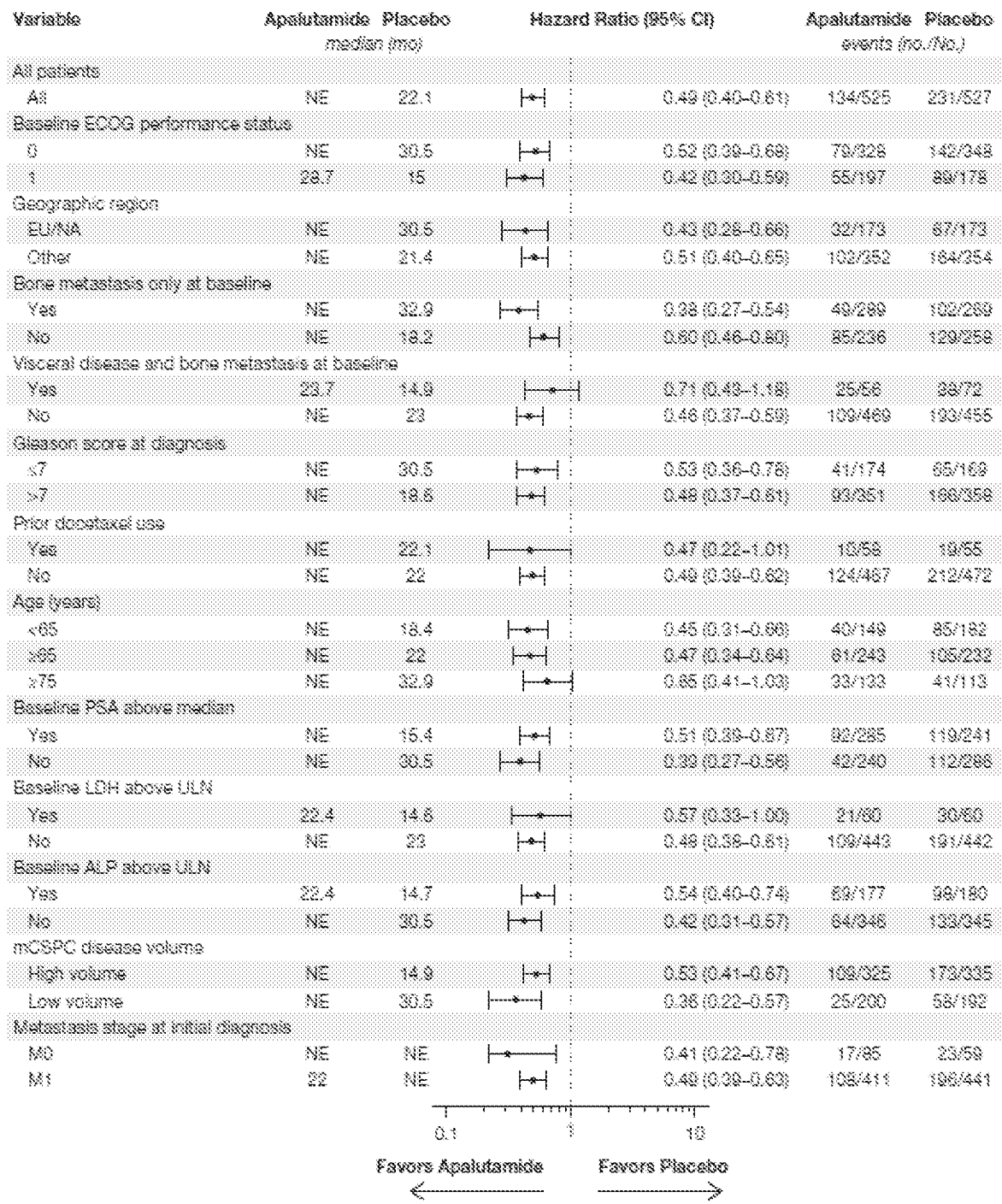

Radiographic Progression-Free Survival and Overall Survival 365 radiographic progression events were observed (134 apalutamide, 231 placebo). The 24-month event-free rates were 68% in the apalutamide group and 48% in the placebo group. Treatment with apalutamide significantly improved radiographic progression-free survival (HR, 0.48; 95% CI, 0.39 to 0.60; P<0.0001), with 52% reduction in risk of radiographic progression or death (FIG. 2A). At this final analysis for radiographic progression-free survival, the median was not reached for apalutamide and 22.1 months for placebo. Apalutamide effect on radiographic progression-free survival was consistently favorable across subgroups analyzed (FIG. 2B), including in prior docetaxel use and disease volume. Independent central review further confirmed investigator assessment of radiographic progression (concordance rate, 85%).

Figure 3A:
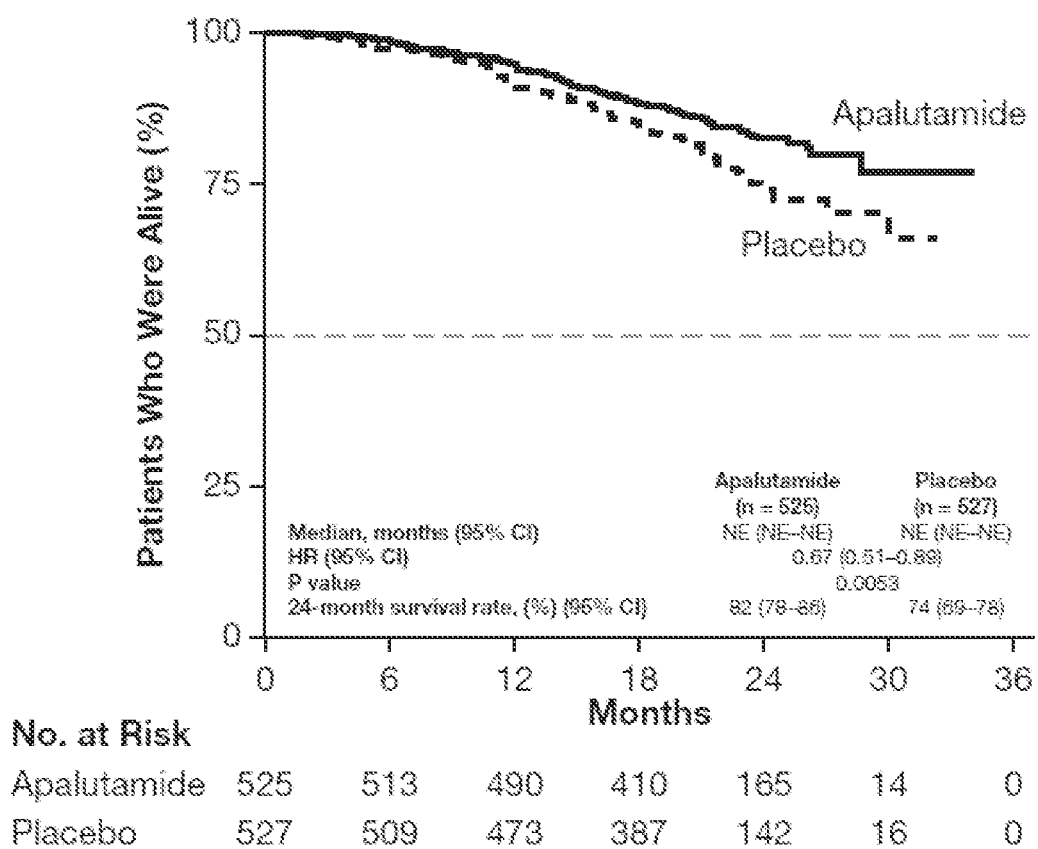
FIG. 3A-3B illustrates Kaplan-Meier Estimate of Overall Survival and (FIG. 3A) and Forest Plot of Overall Survival by Baseline Patient Characteristics (FIG. 3B). Analyses were performed using a log-rank test with stratification by Gleason score at diagnosis (≤7 vs. >7), region (North America and European Union vs. all other countries), and prior treatment with docetaxel (yes vs. no).
Figure 3B:
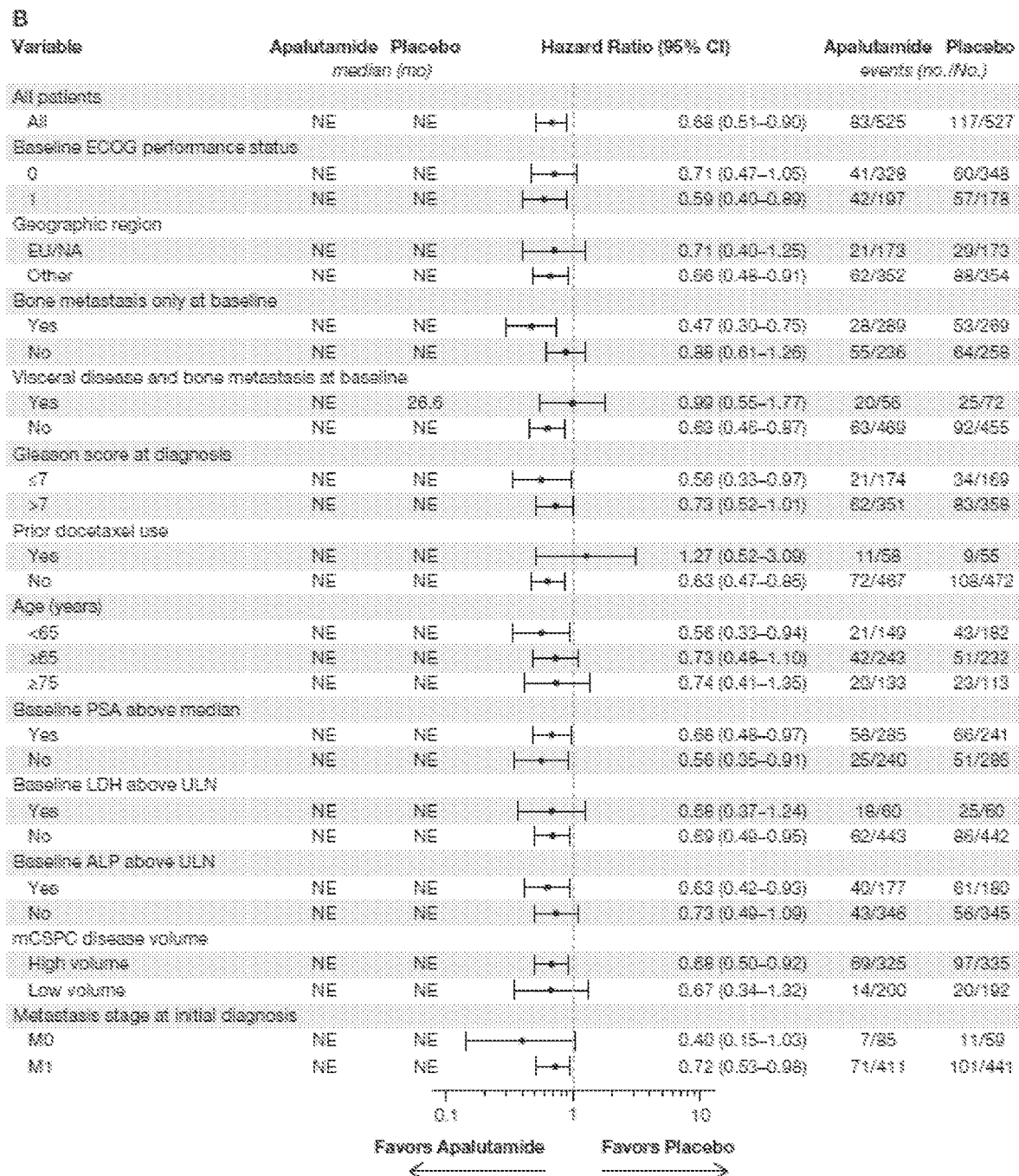

Treatment with apalutamide significantly improved overall survival (24-month event-free rates were 82% and 74% in the apalutamide and placebo groups, respectively; hazard ratio [HR], 0.67; 95% confidence interval [CI], 0.51 to 0.89; P=0.0053), with 33% reduction in risk of death (FIG. 3A). The treatment effect on overall survival consistently favored apalutamide over placebo, with no difference in the apalutamide effect based on disease volume (FIG. 3B).

Secondary End Points

Figure 4:
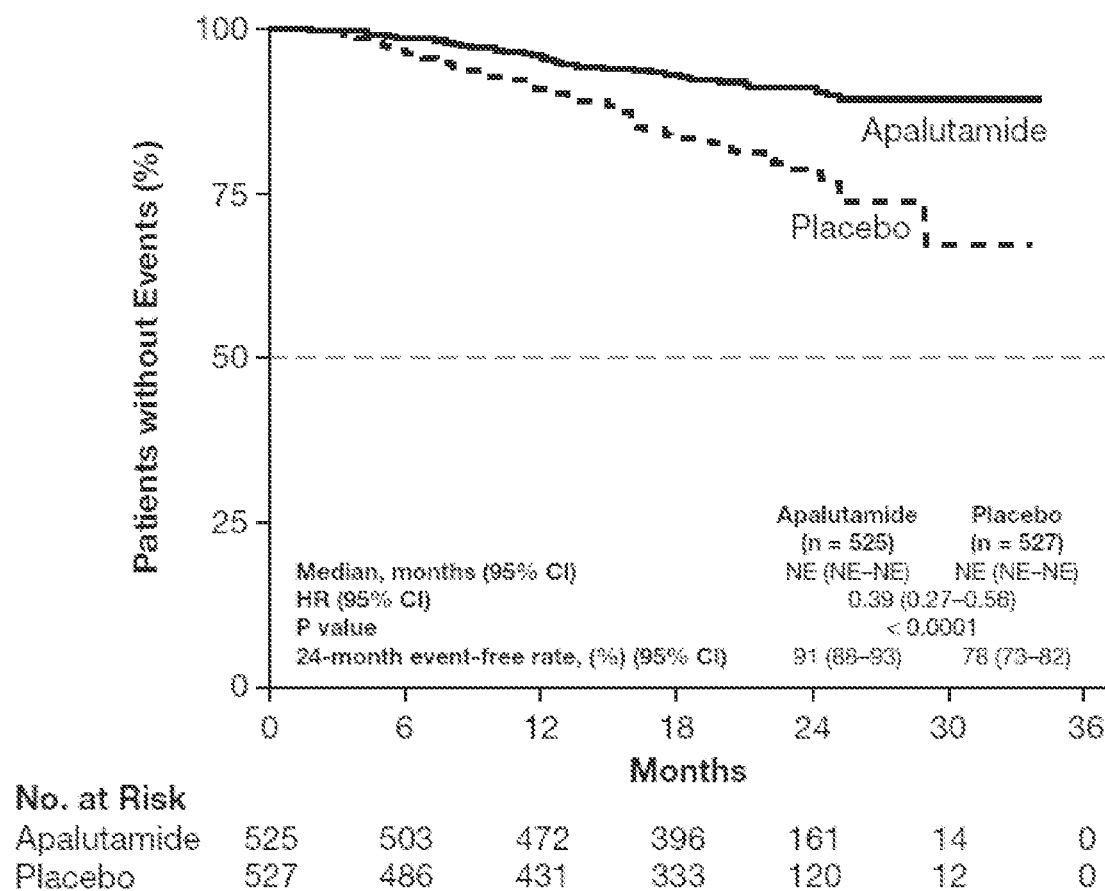
FIG. 4 illustrates Kaplan-Meier Estimate of Time to Cytotoxic Chemotherapy. Analyses were performed using a log-rank test with stratification by Gleason score at diagnosis (≤7 vs. >7), region (North America and European Union vs. all other countries), and prior treatment with docetaxel (yes vs. no).

Time to cytotoxic chemotherapy was significantly improved with apalutamide compared with placebo (Table 4, FIG. 4). Based on the preplanned hierarchical testing sequence, time to pain progression was tested and, because it did not reach statistical significance, no formal testing for further secondary end points was conducted.

TABLE 4

Prespecified Secondary and Exploratory Efficacy End Points.

| End Point | Apalutamide (n = 525) | Placebo (n = 527) | Hazard Ratio (95% CI) | P Value, Stratified Log-rank Test |
|---|---|---|---|---|
| Secondary end points | | | | |
| Median time to cytotoxic chemotherapy - mo | NE | NE | 0.39 (0.27-0.56) | <0.0001 |
| Median time to pain progression* - mo | NE | NE | 0.83 (0.65-1.05) | 0.1173† |
| Median time to chronic opioid use - mo | NE | NE | 0.77 (0.54-1.11) | — |
| Median time to skeletal-related events‡ - mo | NE | NE | 0.80 (0.56-1.15) | — |

TABLE 4-continued

Prespecified Secondary and Exploratory Efficacy End Points.

| End Point | Apalutamide (n = 525) | Placebo (n = 527) | Hazard Ratio (95% CI) | P Value, Stratified Log-rank Test |
|---|---|---|---|---|
| Other clinically relevant end points | | | | |
| Median time to symptomatic progression - mo | NE | NE | 1.20 (0.71-2.02) | |
| Median time to PSA progression - mo | NE | 12.91 | 0.26 (0.21-0.32) | |
| Median second progression-free survival - mo | NE | NE | 0.66 (0.50-0.87) | |

NE, not estimable.
*Pain progression was reported by patients using the BPI-SF worst pain (item 3). Scores range 0 to 10, with lower scores representing lower levels of pain intensity; a change of 2 was the minimally important difference.
†Secondary end points were tested in a preplanned hierarchical sequence. When time to pain progression was determined not to be significantly improved with apalutamide, further secondary end points were not formally tested.
‡Skeletal-related events were defined as the occurrence of symptomatic pathological fracture, spinal cord compression, radiation to bone, or surgery to bone.

Other Clinically Relevant End Points

Figure 5:
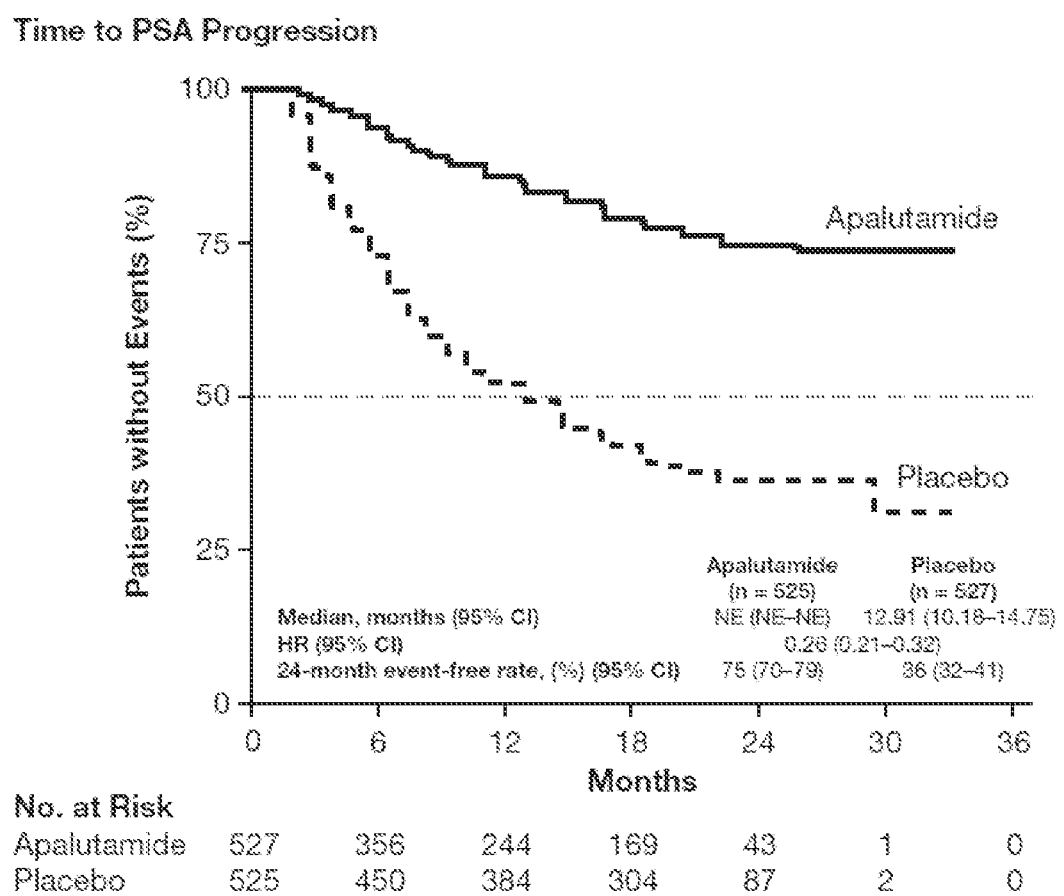
FIG. 5 illustrates Kaplan-Meier Estimate of Time to PSA Progression. Time to PSA progression was the time from date of randomization to date of PSA progression, based on Prostate Cancer Working Group 2 criteria. Analyses were performed using a log-rank test with stratification by Gleason score at diagnosis (≤7 vs. >7), region (North America and European Union vs. all other countries), and prior treatment with docetaxel (yes vs. no).
Figure 6:
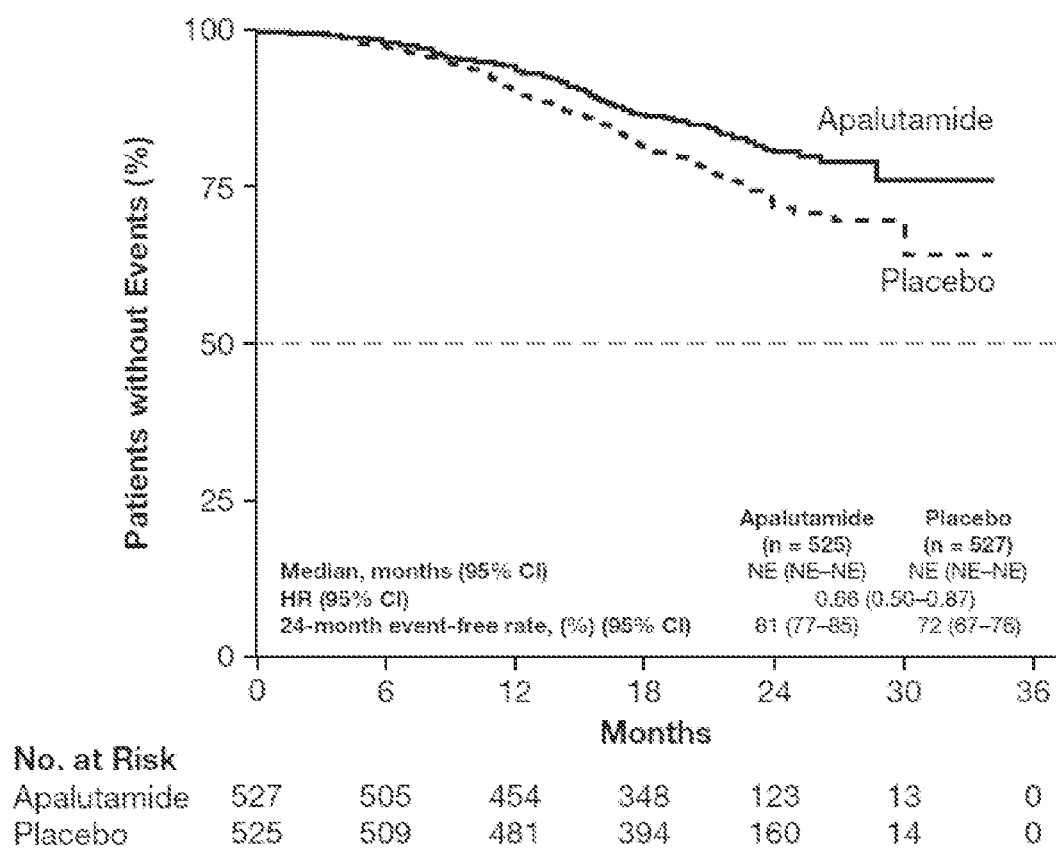
FIG. 6 shows Kaplan-Meier Estimate of Time to Second Progression-free Survival. Second progression-free survival was the time from date of randomization to first occurrence of investigator-determined disease progression (PSA progression, progression on imaging, or clinical progression) while patient was receiving first subsequent therapy for prostate cancer or death due to any cause, whichever occurs first. Analyses were performed using a log-rank test with stratification by Gleason score at diagnosis (≤7 vs. >7), region (North America and European Union vs. all other countries), and prior treatment with docetaxel (yes vs. no).
Figure 7:
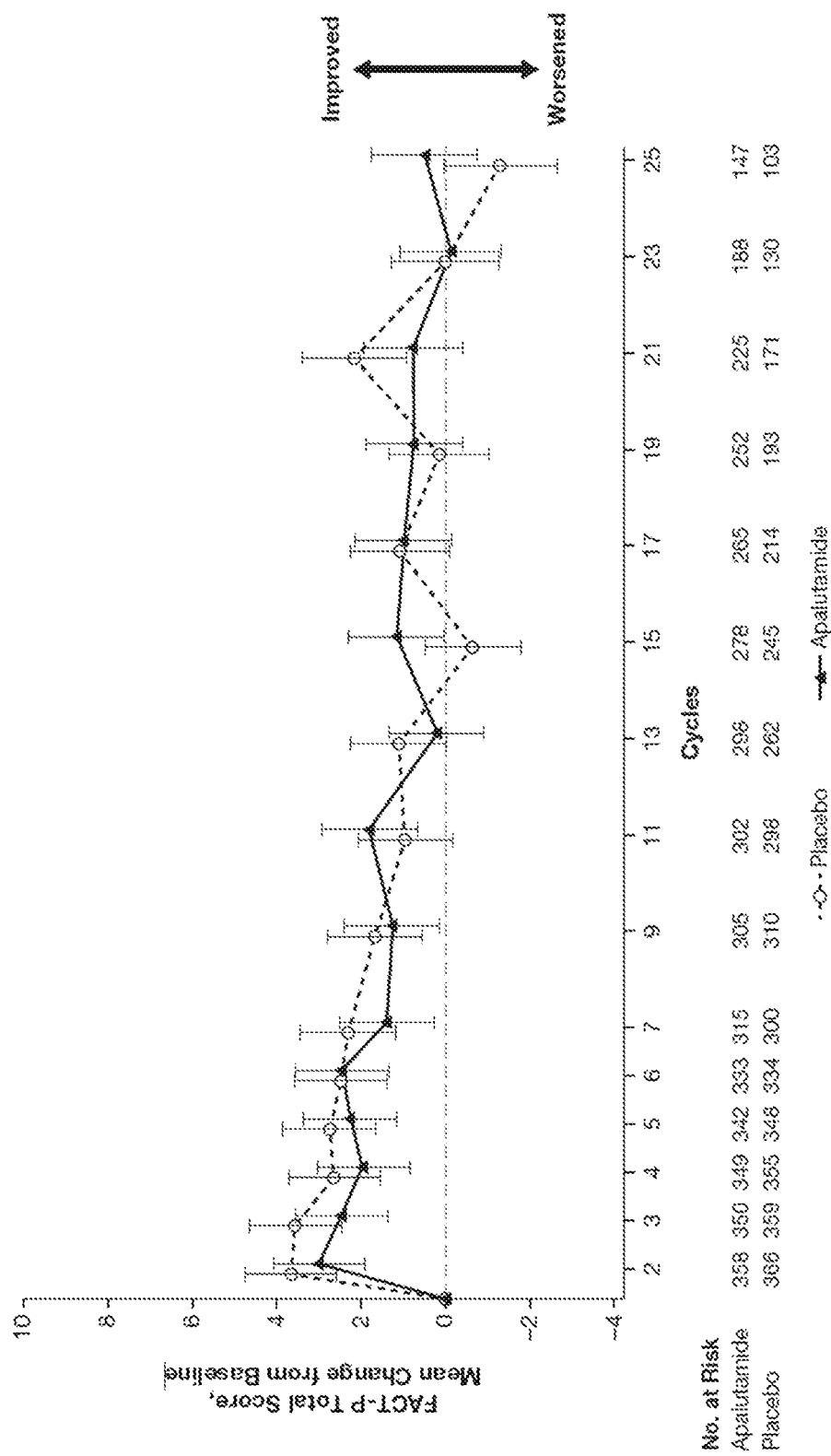
FIG. 7 shows Repeated-Measures Mixed Effects Analyses for Mean Change from Baseline in FACT-P Total Score. Error bars are standard errors of the mean. Raw FACT-P scores range from 0 to 156, with higher scores indicating more favorable health-related quality of life; a 6- to 10-point change in FACT-P total score would be the minimally important difference. However, this figure presents mean changes in total scores compared with baseline rather than raw total scores. FACT-P, Functional Assessment of Cancer Therapy-Prostate.

Median time to PSA progression was more favorable following apalutamide compared with placebo (FIG. 5, Table 4), and PSA reached undetectable levels (PSA <0.2 ng per ml) in 68% and 29% of patients in the apalutamide and placebo groups, respectively. 87 and 190 patients in the apalutamide and placebo groups, respectively, received subsequent treatment for prostate cancer (first therapies described in Table 5). Median second progression-free survival was improved with apalutamide compared with placebo (Table 4; FIG. 6). There were few events and no difference between groups in time to symptomatic local progression (Table 4). Analysis of change in FACT-P from baseline using a mixed-effect repeated measures model demonstrated maintained health-related quality of life and no between-group difference (FIG. 7).

TABLE 5

First Subsequent Systemic Prostate Cancer Therapy

| | Apalutamide (n = 525) | Placebo (n = 527) |
|---|---|---|
| Patients who discontinued treatment for any reason* and remained alive (denominator for first subsequent therapy calculations below)- no. | 170 (%) | 271 (%) |
| Patients who discontinued because of disease progression - no. (%) | 99 (18.9) | 227 (43.1) |
| Patients with adverse events as the primary reason for discontinuation - no. (%) | 39 (7.4) | 17 (3.2) |
| Patients with adverse events leading to discontinuation - no. (%) | 42 (8.0) | 28 (5.3) |
| Patients with life-prolonging subsequent therapy for prostate cancer† - no. (%) | 87 (63) | 190 (78) |
| Patients receiving subsequent systemic prostate cancer therapy at data cutoff‡ - no. (%) | 87 (51.2%) | 190 (70.1%) |
| First subsequent therapy | | |
| Hormonal therapy - no. (%) | 44 (25.9) | 98 (36.2) |
| Abiraterone acetate plus prednisone | 21 (12.4) | 45 (16.6) |
| Bicalutamide | 16 (9.4) | 31 (11.4) |
| Enzalutamide | 3 (1.8) | 17 (6.3) |
| Other‡ | 4 (2.4) | 5 (1.8) |
| Chemotherapy - no. (%) | 35 (20.6) | 73 (26.9) |
| Docetaxel | 29 (17.1) | 67 (24.7) |
| Cabazitaxel | 1 (0.6) | 2 (0.7) |
| Other§ | 5 (2.9) | 4 (1.5) |

TABLE 5-continued

First Subsequent Systemic Prostate Cancer Therapy

| | Apalutamide (n = 525) | Placebo (n = 527) |
|---|---|---|
| Other therapy - no. (%) | 8 (4.7) | 19 (7.0) |
| Radium-223 | 2 (1.2) | 4 (1.5) |
| Sipuleucel-T | 2 (1.2) | 5 (1.8) |
| Other** | 4 (2.4) | 10 (3.7) |

*Possible reasons for discontinuation were disease progression, adverse event, withdrawal by patient, death, physician decision, and protocol violation.
†Included docetaxel, abiraterone acetate plus prednisone, enzalutamide, cabazitaxel, radium-223, and sipuleucel-T.
‡Some patients were unblinded after discontinuation and prior to first subsequent therapy to allow enrollment in a subsequent clinical trial.
§Included diethylstilbestrol, flutamide, and cyproterone.
**Included etoposide, paclitaxel, estramustine, carboplatin, and cisplatin.
*** Included zoledronic acid, clodronate, prednisolone, and prednisone.

Safety

Table 6 presents the most common treatment-emergent adverse events. Frequencies of grade 3 and 4 events (42.2% in the apalutamide group; 40.8% in the placebo group) and of serious adverse events (19.8% in the apalutamide group; 20.3% in the placebo group) were not different between groups. Most treatment discontinuations were the result of progressive disease (99 [19%] apalutamide; 227 [43%] placebo; Table 5). Adverse events led to discontinuation in (42 (8.0%) patients in the apalutamide group and 28 (5.3%) in the placebo group (Table 7). Ten (1.9%) and 16 (3.0%) patients in the apalutamide and placebo groups, respectively, died as the result of an adverse event (Table 8). Rash of any grade was more common among patients treated with apalutamide than placebo (27.1% and 8.5%, respectively; Table 6), and the most common event considered related to apalutamide was rash of any type (6.3%). Hypothyroidism was reported by 6.5% and 1.1% in each group, respectively (Table 6); all events were grade 1 or 2. Ischemic heart disease was reported in 4.4% and 1.5% of patients in the apalutamide and placebo groups, respectively; ischemic events led to death in two patients in each group.

TABLE 6

Treatment-Emergent Adverse Events.

| Adverse Event | Apalutamide (n = 524) | Placebo (n = 527) |
|---|---|---|

TABLE 6-continued

Treatment-Emergent Adverse Events.

| | Apalutamide | Placebo |
|---|---|---|
| Any adverse event | 507 (96.8) | 509 (96.6) |
| Grade 3 or 4 adverse event | 221 (42.2) | 215 (40.8) |
| Any serious adverse event | 104 (19.8) | 107 (20.3) |
| Any adverse event leading to treatment discontinuation | 42 (8.0) | 28 (5.3) |
| Adverse event leading to death | 10 (1.9) | 16 (3.0) |

| | All Grades | Grade ≥3 | All Grades | Grade ≥3 |
|---|---|---|---|---|
| Treatment-Emergent Adverse Events Reported in ≥10% of Patients or Grade ≥3 in ≥10 Patients in Either Group | | | | |
| Hot flush | 119 (22.7) | 0 | 86 (16.3) | 0 |
| Fatigue | 103 (19.7) | 8 (1.5) | 88 (16.7) | 6 (1.1) |
| Hypertension | 93 (17.7) | 44 (8.4) | 82 (15.6) | 48 (9.1) |
| Back pain | 91 (17.4) | 12 (2.3) | 102 (19.4) | 14 (2.7) |
| Arthralgia | 91 (17.4) | 2 (0.4) | 78 (14.8) | 5 (0.9) |
| Pain in extremity | 64 (12.2) | 3 (0.6) | 67 (12.7) | 5 (0.9) |
| Pruritus | 56 (10.7) | 1 (0.2) | 24 (4.6) | 1 (0.2) |
| Weight increased | 54 (10.3) | 6 (1.1) | 89 (16.9) | 10 (1.9) |
| Anemia | 48 (9.2) | 9 (1.7) | 71 (13.5) | 17 (3.2) |
| Constipation | 47 (9.0) | 0 | 57 (10.8) | 0 |
| Asthenia | 37 (7.1) | 10 (1.9) | 44 (8.3) | 3 (0.6) |
| Bone pain | 34 (6.5) | 6 (1.1) | 53 (10.1) | 9 (1.7) |
| Rash generalized | 34 (6.5) | 14 (2.7) | 5 (0.9) | 2 (0.4) |
| Blood alkaline phosphatase increased | 16 (3.1) | 2 (0.4) | 28 (5.3) | 13 (2.5) |
| Urinary retention | 13 (2.5) | 0 | 19 (3.6) | 10 (1.9) |
| Adverse Events of Special Interest | | | | |
| Rash* | 142 (27.1) | 33 (6.3) | 45 (8.5) | 3 (0.6) |
| Fall | 39 (7.4) | 4 (0.8) | 37 (7.0) | 4 (0.8) |
| Fracture† | 33 (6.3) | 7 (1.3) | 24 (4.6) | 4 (0.8) |
| Hypothyroidism‡ | 34 (6.5) | 0 | 6 (1.1) | 0 |
| Seizure§ | 3 (0.6) | 1 (0.2) | 2 (0.4) | 0 |

Values are no. (%).

*Rash was a grouped term including rash, butterfly rash, erythematous rash, exfoliative rash, follicular rash, generalized rash, macular rash, maculo-papular rash, papules, papular rash, pruritic rash, pustular rash, genital rash, blister, skin exfoliation, exfoliative dermatitis, skin reaction, systemic lupus erythematosus rash, toxic skin eruption, mouth ulceration, drug eruption, conjunctivitis, erythema multiforme, stomatitis, and urticaria.

†Fracture was a grouped term including acetabulum fracture, ankle fracture, clavicle fracture, femoral neck fracture, femur fracture, fibula fracture, foot fracture, forearm fracture, fracture, fractured ischium, fracture pain, hand fracture, hip fracture, lower limb fracture, patella fracture, radius fracture, rib fracture, skull fracture, spinal compression fracture, spinal fracture, sternal fracture, thoracic vertebral fracture, tibia fracture, traumatic fracture, ulna fracture, upper limb fracture, and wrist fracture.

‡Hypothyroidism was a grouped term including autoimmune thyroiditis, blood thyroid stimulating hormone increased, and hypothyroidism.

§Seizure was a grouped term including seizure and tongue biting.

TABLE 7

Treatment-Emergent Adverse Events Leading to Treatment Discontinuation, Dose Reduction, and Dose Interruption

| | Apalutamide (n = 524) | | Placebo (n = 527) | |
|---|---|---|---|---|
| | All Grades | Grade ≥3 | All Grades | Grade ≥3 |
| Discontinuation | | | | |
| Patients with treatment-emergent adverse events leading to discontinuation - no. (%) | 42 (8.0) | 26 (5.0) | 28 (5.3) | 22 (4.2) |
| Rash* | 12 (2.3) | 7 (1.3) | 1 (0.2) | 1 (0.2) |
| New cancer neoplasm† | 7 (1.3) | 5 (1.0) | 5 (0.9) | 3 (0.6) |
| Infections‡ | 1 (0.2) | 1 (0.2) | 3 (0.6) | 0 |
| Fatigue | 4 (0.8) | 1 (0.2) | 0 | 0 |
| Ischemic cardiac events§ | 2 (0.4) | 2 (0.4) | 2 (0.4) | 2 (0.4) |
| Seizure | 2 (0.4) | 1 (0.2) | 1 (0.2) | 0 |
| Pulmonary embolism | 1 (0.2) | 1 (0.2) | 2 (0.4) | 1 (0.2) |
| Sudden death | 0 | 0 | 2 (0.4) | 2 (0.4) |
| Cerebrovascular disorder | 1 (0.2) | 1 (0.2) | 0 | 0 |
| Parkinson's disease | 1 (0.2) | 1 (0.2) | 0 | 0 |
| Radiculopathy | 1 (0.2) | 1 (0.2) | 0 | 0 |
| Cognitive disorder | 0 | 0 | 1 (0.2) | 0 |
| Intracranial hemorrhage | 0 | 0 | 1 (0.2) | 1 (0.2) |
| Loss of consciousness | 0 | 0 | 1 (0.2) | 1 (0.2) |
| Atrial fibrillation | 1 (0.2) | 1 (0.2) | 0 | 0 |
| Cardio-respiratory arrest | 1 (0.2) | 1 (0.2) | 0 | 0 |
| Cardiogenic shock | 1 (0.2) | 1 (0.2) | 0 | 0 |
| Cardiac failure | 0 | 0 | 1 (0.2) | 1 (0.2) |
| Sudden cardiac death | 1 (0.2) | 1 (0.2) | 0 | 0 |
| Hypothermia | 0 | 0 | 1 (0.2) | 1 (0.2) |
| Anxiety | 1 (0.2) | 0 | 0 | 0 |
| Euphoric mood | 1 (0.2) | 0 | 0 | 0 |
| Suicide | 0 | 0 | 1 (0.2) | 1 (0.2) |
| Large intestinal ulcer perforation | 1 (0.2) | 1 (0.2) | 0 | 0 |
| Lip swelling | 1 (0.2) | 0 | 0 | 0 |
| Dyspnea | 0 | 0 | 1 (0.2) | 0 |
| Pleural effusion | 0 | 0 | 1 (0.2) | 1 (0.2) |
| Pulmonary edema | 0 | 0 | 1 (0.2) | 1 (0.2) |
| Respiratory failure | 0 | 0 | 1 (0.2) | 1 (0.2) |

TABLE 7-continued

Treatment-Emergent Adverse Events Leading to Treatment
Discontinuation, Dose Reduction, and Dose Interruption

| | Apalutamide (n = 524) | | Placebo (n = 527) | |
|---|---|---|---|---|
| | All Grades | Grade ≥3 | All Grades | Grade ≥3 |
| Dehydration | 1 (0.2) | 0 | 0 | 0 |
| Hot flush | 1 (0.2) | 0 | 0 | 0 |
| Subdural hemorrhage | 0 | 0 | 1 (0.2) | 1 (0.2) |
| Alanine aminotransferase increased | 0 | 0 | 1 (0.2) | 1 (0.2) |
| Dose Reduction | | | | |
| Patients with treatment-emergent adverse events leading to dose reduction - no. (%) | 37 (7.1) | 19 (3.6) | 11 (2.1) | 1 (0.2) |
| Rash* | 28 (5.3) | 11 (2.1) | 4 (0.8) | 1 (0.2) |
| Aspartate aminotransferase or alanine aminotransferase increased | 0 | 0 | 4 (0.8) | 0 |
| Fatigue | 2 (0.4) | 2 (0.4) | 0 | 0 |
| Headache | 1 (0.2) | 0 | 1 (0.2) | 0 |
| Hypertension | 1 (0.2) | 1 (0.2) | 1 (0.2) | 0 |
| Neutropenia | 2 (0.4) | 2 (0.4) | 0 | 0 |
| Cognitive disorder | 1 (0.2) | 1 (0.2) | 0 | 0 |
| General physical health deterioration | 1 (0.2) | 1 (0.2) | 0 | 0 |
| Hot flush | 1 (0.2) | 0 | 0 | 0 |
| Asthenia | 0 | 0 | 1 (0.2) | 0 |
| Dehydration | 1 (0.2) | 0 | 0 | 0 |
| Lethargy | 0 | 0 | 1 (0.2) | 0 |
| Pain** | 1 (0.2) | 0 | 0 | 0 |
| Performance status decreased | 0 | 0 | 1 (0.2) | 0 |
| Vertigo | 1 (0.2) | 1 (0.2) | 0 | 0 |
| Weight decreased | 1 (0.2) | 1 (0.2) | 0 | 0 |
| Dose Interruption | | | | |
| Patients with treatment-emergent events leading to dose interruption - no. (%) | 104 (19.8) | 68 (13.0) | 63 (12.0) | 43 (8.2) |
| Rash* | 44 (8.4) | 20 (3.8) | 5 (0.9) | 2 (0.4) |
| Aspartate aminotransferase or alanine aminotransferase increased | 7 (1.3) | 4 (0.8) | 12 (2.3) | 7 (1.3) |
| Pain** | 9 (1.7) | 4 (0.8) | 7 (1.3) | 3 (0.6) |
| Infections‡ | 6 (1.1) | 4 (0.8) | 9 (1.7) | 3 (0.6) |
| Hypertension | 6 (1.1) | 6 (1.1) | 6 (1.1) | 6 (1.1) |
| Fatigue | 6 (1.1) | 1 (0.2) | 2 (0.4) | 1 (0.2) |
| Vomiting | 3 (0.6) | 0 | 4 (0.8) | 0 |
| Anemia | 2 (0.4) | 0 | 3 (0.6) | 2 (0.4) |
| Asthenia | 3 (0.6) | 3 (0.6) | 2 (0.4) | 1 (0.2) |
| Decreased appetite | 2 (0.4) | 1 (0.2) | 3 (0.6) | 1 (0.2) |
| New cancer neoplasm† | 3 (0.6) | 1 (0.2) | 1 (0.2) | 1 (0.2) |
| Diarrhea | 1 (0.2) | 0 | 3 (0.6) | 0 |
| Chronic obstructive pulmonary disease | 2 (0.4) | 2 (0.4) | 2 (0.4) | 2 (0.4) |
| Pyrexia | 3 (0.6) | 0 | 1 (0.2) | 0 |
| Urinary retention | 2 (0.4) | 2 (0.4) | 2 (0.4) | 2 (0.4) |
| Arthralgia | 2 (0.4) | 0 | 1 (0.2) | 0 |
| Insomnia | 3 (0.6) | 0 | 0 | 0 |
| Acute kidney injury | 1 (0.2) | 1 (0.2) | 1 (0.2) | 1 (0.2) |
| Anxiety | 2 (0.4) | 0 | 0 | 0 |
| Cerebrovascular accident | 1 (0.2) | 1 (0.2) | 1 (0.2) | 0 |
| Dizziness | 1 (0.2) | 0 | 1 (0.2) | 0 |
| Dyspnea | 1 (0.2) | 0 | 1 (0.2) | 1 (0.2) |
| Fall | 1 (0.2) | 1 (0.2) | 1 (0.2) | 1 (0.2) |
| Headache | 1 (0.2) | 0 | 1 (0.2) | 1 (0.2) |
| Hematuria | 2 (0.4) | 2 (0.4) | 0 | 0 |
| Hot flush | 1 (0.2) | 0 | 1 (0.2) | 0 |
| Hypersensitivity | 1 (0.2) | 0 | 1 (0.2) | 0 |
| Hypertriglyceridemia | 2 (0.4) | 2 (0.4) | 0 | 0 |
| Hyponatremia | 1 (0.2) | 1 (0.2) | 1 (0.2) | 1 (0.2) |
| Muscular weakness | 1 (0.2) | 0 | 1 (0.2) | 1 (0.2) |
| Nausea | 1 (0.2) | 0 | 1 (0.2) | 0 |
| Neutropenia | 2 (0.4) | 2 (0.4) | 0 | 0 |
| Spinal cord compression | 1 (0.2) | 1 (0.2) | 1 (0.2) | 1 (0.2) |
| Acute respiratory failure | 1 (0.2) | 1 (0.2) | 0 | 0 |
| Allergy to chemicals | 1 (0.2) | 1 (0.2) | 0 | 0 |
| Angina unstable | 0 | 0 | 1 (0.2) | 1 (0.2) |
| Atrial fibrillation | 1 (0.2) | 1 (0.2) | 0 | 0 |
| Bile duct obstruction | 0 | 0 | 1 (0.2) | 0 |
| Blood alkaline phosphatase increased | 1 (0.2) | 1 (0.2) | 0 | 0 |
| Cardiac amyloidosis | 0 | 0 | 1 (0.2) | 1 (0.2) |
| Cardiac disorder | 0 | 0 | 1 (0.2) | 1 (0.2) |

TABLE 7-continued

Treatment-Emergent Adverse Events Leading to Treatment Discontinuation, Dose Reduction, and Dose Interruption

|  | Apalutamide (n = 524) | | Placebo (n = 527) | |
| --- | --- | --- | --- | --- |
|  | All Grades | Grade ≥3 | All Grades | Grade ≥3 |
| Cardiac failure | 0 | 0 | 1 (0.2) | 0 |
| Cardiac failure congestive | 1 (0.2) | 1 (0.2) | 0 | 0 |
| Cheilitis | 1 (0.2) | 0 | 0 | 0 |
| Chronic hepatitis | 1 (0.2) | 0 | 0 | 0 |
| Cognitive disorder | 1 (0.2) | 1 (0.2) | 0 | 0 |
| Confusional state | 1 (0.2) | 1 (0.2) | 0 | 0 |
| Constipation | 1 (0.2) | 0 | 0 | 0 |
| Dehydration | 0 | 0 | 1 (0.2) | 0 |
| Depression | 1 (0.2) | 0 | 0 | 0 |
| Diabetes mellitus | 1 (0.2) | 1 (0.2) | 0 | 0 |
| Diplegia | 0 | 0 | 1 (0.2) | 1 (0.2) |
| Dysuria | 1 (0.2) | 1 (0.2) | 0 | 0 |
| Edema | 1 (0.2) | 0 | 0 | 0 |
| Eyelid edema | 1 (0.2) | 0 | 0 | 0 |
| Facial edema | 1 (0.2) | 0 | 0 | 0 |
| Febrile neutropenia | 1 (0.2) | 1 (0.2) | 0 | 0 |
| Gamma-glutamyltransferase increased | 1 (0.2) | 1 (0.2) | 0 | 0 |
| Gastric ulcer perforation | 1 (0.2) | 1 (0.2) | 0 | 0 |
| Gastritis | 0 | 0 | 1 (0.2) | 1 (0.2) |
| General physical health deterioration | 1 (0.2) | 1 (0.2) | 0 | 0 |
| Hallucination | 1 (0.2) | 0 | 0 | 0 |
| Hematoma | 1 (0.2) | 1 (0.2) | 0 | 0 |
| Hemorrhagic erosive gastritis | 1 (0.2) | 1 (0.2) | 0 | 0 |
| Hemorrhage intracranial | 1 (0.2) | 1 (0.2) | 0 | 0 |
| Hepatic cirrhosis | 1 (0.2) | 0 | 0 | 0 |
| Hepatic failure | 0 | 0 | 1 (0.2) | 1 (0.2) |
| Hip fracture | 1 (0.2) | 1 (0.2) | 0 | 0 |
| Hypokalemia | 1 (0.2) | 1 (0.2) | 0 | 0 |
| Hydronephrosis | 0 | 0 | 1 (0.2) | 1 (0.2) |
| Hyperbilirubinemia | 1 (0.2) | 1 (0.2) | 0 | 0 |
| Influenza-like illness | 1 (0.2) | 0 | 0 | 0 |
| Large intestinal ulcer perforation | 1 (0.2) | 1 (0.2) | 0 | 0 |
| Mental status changes | 1 (0.2) | 0 | 0 | 0 |
| Musculoskeletal stiffness | 0 | 0 | 1 (0.2) | 0 |
| Ischemic cardiac events§ | 1 (0.2) | 1 (0.2) | 0 | 0 |
| Osteoarthritis | 0 | 0 | 1 (0.2) | 1 (0.2) |
| Osteoporosis | 1 (0.2) | 0 | 0 | 0 |
| Pathological fracture | 0 | 0 | 1 (0.2) | 1 (0.2) |
| Peripheral edema | 1 (0.2) | 0 | 0 | 0 |
| Peripheral swelling | 0 | 0 | 1 (0.2) | 1 (0.2) |
| Proctalgia | 1 (0.2) | 0 | 0 | 0 |
| Renal injury | 0 | 0 | 1 (0.2) | 0 |
| Rheumatoid arthritis | 1 (0.2) | 1 (0.2) | 0 | 0 |
| Seizure | 1 (0.2) | 0 | 0 | 0 |
| Stomatitis | 1 (0.2) | 0 | 0 | 0 |
| Subarachnoid hematoma | 1 (0.2) | 1 (0.2) | 0 | 0 |
| Subarachnoid hemorrhage | 1 (0.2) | 0 | 0 | 0 |
| Subdural hemorrhage | 0 | 0 | 1 (0.2) | 1 (0.2) |
| Syncope | 1 (0.2) | 1 (0.2) | 0 | 0 |
| Thrombocytopenia | 1 (0.2) | 0 | 0 | 0 |
| Tongue ulceration | 1 (0.2) | 0 | 0 | 0 |
| Urinary incontinence | 1 (0.2) | 0 | 0 | 0 |
| Urinary tract obstruction | 1 (0.2) | 1 (0.2) | 0 | 0 |
| Urethral stenosis | 0 | 0 | 1 (0.2) | 0 |
| Vertigo | 1 (0.2) | 1 (0.2) | 0 | 0 |
| Weight increased | 0 | 0 | 1 (0.2) | 0 |

*Rash was a grouped term including eczema, eczema nummular, exfoliative rash, generalized rash, rash, dermatitis, dermatitis exfoliative, psoriasis, hyperhidrosis, maculopapular rash, macular rash, drug eruption, erythema multiforme, lichenoid keratosis, pruritus, pruritic rash, skin exfoliation, skin lesion, skin reaction, and toxic skin eruption.

†New cancer neoplasms (benign, malignant, and unspecified [including cysts and polyps]) was a grouped term including malignant lung neoplasms, colon adenoma, colon neoplasms, leiomyosarcoma, oropharyngeal cancer, papilloma, rectal adenocarcinoma, small-cell carcinoma, gastric adenocarcinoma, colon adenocarcinoma, bladder cancer, and non-small-cell lung cancer.

‡Infections was a grouped term including urinary tract infection, *Klebsiella* infection, sepsis, urosepsis, fungal infection, localized infection, lung infection, pneumonia, fungal respiratory tract infection, acarodermatitis, cellulitis, bacterial bronchitis, influenza, necrotizing fasciitis, and viral upper respiratory tract infection.

§Ischemic cardiac events was a grouped term including myocardial infarction, acute myocardial infarction, acute coronary syndrome.

**Pain was a grouped term including pain in extremity, back pain, bone pain, upper abdominal pain, lower abdominal pain, musculoskeletal pain, neck pain, and noncardiac chest pain.

TABLE 8

Investigator Reported Cause of Death on Study in the Safety Population

|  | Apalutamide (n = 524) | Placebo (n = 527) |
|---|---|---|
| All deaths within 30 days of last dose - no. (%) | 18 (3.4) | 23 (4.4) |
| Death due to prostate cancer | 8 (1.5) | 7 (1.3) |
| Death due to adverse event | 10 (1.9) | 16 (3.0) |
| Adverse events leading to death - no. (%) | | |
| Respiratory failure | 1 (0.2) | 2 (0.4) |
| Acute kidney injury | 2 (0.4) | 0 |
| Acute myocardial infarction | 1 (0.2) | 1 (0.2) |
| Sudden death | 0 | 2 (0.4) |
| Acute coronary syndrome | 0 | 1 (0.2) |
| Cardiac failure | 0 | 1 (0.2) |
| Cardio-respiratory arrest | 1 (0.2) | 0 |
| Cardiogenic shock | 1 (0.2) | 0 |
| Cerebrovascular accident | 1 (0.2) | 0 |
| Death | 0 | 1 (0.2) |
| Hypothermia | 0 | 1 (0.2) |
| Intracranial hemorrhage | 0 | 1 (0.2) |
| Large intestinal ulcer perforation | 1 (0.2) | 0 |
| Myocardial infarction | 1 (0.2) | 0 |
| Pulmonary embolism | 0 | 1 (0.2) |
| Sepsis | 0 | 1 (0.2) |
| Subdural hemorrhage | 0 | 1 (0.2) |
| Sudden cardiac death | 1 (0.2) | 0 |
| Suicide | 0 | 1 (0.2) |
| Urosepsis | 0 | 1 (0.2) |
| Vascular rupture | 0 | 1 (0.2) |

A post-hoc analysis accounting for the competing risk of death was performed based on the Fine and Gray model (Table 9). Fine J P, Gray R J., *J Am Stat Assoc* 1999; 94:496-509. The estimates of a subdistribution hazard ratio of the apalutamide group relative to the placebo group, along with the respective 95% confidence limits and the P values from the Wald Chi-Square test, are presented. The results of this post-hoc analysis supported and confirmed the pre-planned analysis results.

TABLE 9

Estimates of Subdistribution Hazard Ratio of the Apalutamide Group Relative to the Placebo Group

|  | P Value | Hazard Ratio | 95% Confidence Limits of the Hazard Ratio | |
|---|---|---|---|---|
| Time to cytotoxic chemotherapy | <0.0001 | 0.408 | 0.286 | 0.581 |
| Time to pain progression | 0.1540 | 0.843 | 0.667 | 1.066 |
| Time to chronic opioid use | 0.2004 | 0.789 | 0.549 | 1.134 |
| Time to skeletal-related event | 0.2759 | 0.818 | 0.570 | 1.174 |

Rash Management

Skin rash associated with apalutamide was commonly described as generalized or maculo-papular. Treatment-emergent skin rash was reported by 27.1% of patients in the apalutamide group versus 8.5% in the placebo group. Grade 3 rashes were reported with apalutamide (6.3%) and placebo (0.6%) treatment. No Stevens-Johnson syndrome or toxic epidermal necrolysis was reported. Skin rash led to treatment discontinuation, dose reduction, and dose interruption in 12 (2.3%), 28 (5.3%), and 44 (8.4%), patients, respectively, in the apalutamide group, and 1 (0.2%), 4 (0.8%), and 5 (0.90%), patients, respectively, in the placebo group. Grade ≥3 rash led to discontinuation in 7 (1.3%) and 1 (0.2%) patients in the apalutamide and placebo groups, respectively (Table 7). For patients who had a skin rash, treatment included topical corticosteroids, oral antihistamines, systemic corticosteroids, drug interruption, and dose reduction. Median time to onset of rash was 81 days in the apalutamide group and 141 days in the placebo group.

Discussion in this phase 3 study in men with metastatic castration-sensitive prostate cancer (mCSPC), apalutamide plus ADT significantly improved overall survival and radiographic progression-free survival compared with placebo plus ADT. The reduced risk of death was not different based on disease volume, and benefits in radiographic progression-free survival were consistently observed across all subgroups analyzed, including patients with prior docetaxel exposure. Longer survival with apalutamide was observed even though a higher proportion of patients in the placebo group who discontinued treatment received life-prolonging subsequent therapy for prostate cancer (64 of 170 patients [38%] and 165 of 271 patients [61%] in the apalutamide and placebo groups, respectively; Table 5). Based on results from this first planned interim analysis, the independent data-monitoring committee recommended unblinding to allow crossover of patients receiving placebo to receive apalutamide.

Secondary and exploratory end points also favored apalutamide treatment, including time to cytotoxic chemotherapy and time to second progression-free survival. Apalutamide plus ADT also resulted in a greater proportion of patients achieving undetectable PSA levels and a delay in time to PSA progression compared with placebo plus ADT. In this exemplified study, initial therapy with apalutamide in patients with metastatic castration-sensitive prostate cancer led to improved clinical outcomes.

The intent of the trial was to enroll a broad group of patients with metastatic castration-sensitive prostate cancer, resulting in the limitation that certain patient subgroups were relatively small. For example, although all patients acknowledged the survival benefit of docetaxel during informed consent, only 11% received prior docetaxel before study enrollment. This likely reflects perceived patient fitness for docetaxel and differences in patient choice or care approaches. However, the consistency of clinical benefit of apalutamide across all subgroups is reassuring.

Rates of high-grade and serious adverse events were not different in the apalutamide and placebo groups; rates of discontinuation due to adverse events were low in both groups. Adverse events were generally consistent with the known apalutamide safety profile. Rash related to treatment with apalutamide was common and typically managed with antihistamines and topical glucocorticoids, dose interruption, and dose reduction. Hypothyroidism was mild to moderate, monitored by thyroid-stimulating hormone, and managed with levothyroxine. Health-related quality of life was also preserved, with no difference between groups, supporting tolerability of apalutamide plus ADT.

In conclusion, in the exemplified study in patients with metastatic castration-sensitive prostate cancer, including those with high- and low-volume disease, prior docetaxel, prior treatment for localized disease, and patients with previously diagnosed or de novo disease, addition of apalutamide to ADT significantly improved overall survival and delayed disease progression, with a safety profile not notably different from placebo plus ADT, and preserved health-related quality of life.

Formulation of Apalutamide

The apalutamide tablet supplied for this study contains 60-mg of apalutamide. It was manufactured and provided under the responsibility of the sponsor.

Placebo was provided as a tablet formulation and will be matched in size, color, and shape in order to maintain the study blind.

Packaging

Apalutamide 60-mg tablets were packaged in 120-count, 160 cc high-density polyethylene (HDPE) bottles with child-resistant closures.

Example 2: Final FDA Approved Drug Product Label

The FDA approved the following drug product label on Sep. 17, 2019 for ERLEADA™ (apalutamide), which will be the reference listed drug for apalutamide.

HIGHLIGHTS OF PRESCRIBING INFORMATION

These highlights do not include all the information needed to use ERLEADA safely and effectively. See full prescribing information for ERLEADA.

ERLEADA® (apalutamide) tablets, for oral use
Initial U.S. Approval – 2018

---------RECENT MAJOR CHANGES---------

| | |
|---|---|
| Indications and Usage (1) | 09/2019 |
| Warnings and Precautions (5) | 09/2019 |

---------INDICATIONS AND USAGE---------

ERLEADA is an androgen receptor inhibitor indicated for the treatment of patients with
- metastatic castration-sensitive prostate cancer. (1)
- non-metastatic castration-resistant prostate cancer. (1)

---------DOSAGE AND ADMINISTRATION---------

ERLEADA 240 mg (four 60 mg tablets) administered orally once daily. Swallow tablets whole. ERLEADA can be taken with or without food. (2.1)

Patients should also receive a gonadotropin-releasing hormone (GnRH) analog concurrently or should have had bilateral orchiectomy. (2.1)

---------DOSAGE FORMS AND STRENGTHS---------

Tablets: 60 mg (3)

---------CONTRAINDICATIONS---------

None.

---------WARNINGS AND PRECAUTIONS---------

- Ischemic cardiovascular events occurred in patients receiving ERLEADA. Monitor for signs and symptoms of ischemic heart disease. Optimize management of cardiovascular risk factors. (5.1)
- Fractures occurred in patients receiving ERLEADA. Evaluate patients for fracture risk and treat patients with bone-targeted agents according to established guidelines. (5.2)
- Falls occurred in patients receiving ERLEADA with increased incidence in the elderly. Evaluate patients for fall risk. (5.3)
- Seizure occurred in 0.4% of patients receiving ERLEADA. Permanently discontinue ERLEADA in patients who develop a seizure during treatment. (5.4)
- Embryo-Fetal Toxicity: ERLEADA can cause fetal harm. Advise males with female partners of reproductive potential to use effective contraception. (5.5, 8.1, 8.3)

---------ADVERSE REACTIONS---------

The most common adverse reactions (≥10%) are fatigue, arthralgia, rash, decreased appetite, fall, weight decreased, hypertension, hot flush, diarrhea, and fracture. (6.1)

To report SUSPECTED ADVERSE REACTIONS, contact Janssen Products, LP at 1-800-526-7736 (1-800-JANSSEN) or FDA at 1-800-FDA-1088 or www.fda.gov/medwatch.

---------DRUG INTERACTIONS---------

- Concomitant use with medications that are sensitive substrates of CYP3A4, CYP2C9, CYP2C19, UGT, P-gp, BCRP, or OATP1B1 may result in loss of activity of these medications. (7.2)

See 17 for PATIENT COUNSELING INFORMATION and FDA-approved patient labeling.

Revised: 09/2019

---

FULL PRESCRIBING INFORMATION: CONTENTS*

1. INDICATIONS AND USAGE
2. DOSAGE AND ADMINISTRATION
   2.1 Recommended Dosage
   2.2 Dose Modification
3. DOSAGE FORMS AND STRENGTHS
4. CONTRAINDICATIONS
5. WARNINGS AND PRECAUTIONS
   5.1 Ischemic Cardiovascular Events
   5.2 Fractures
   5.3 Falls
   5.4 Seizure
   5.5 Embryo-Fetal Toxicity
6. ADVERSE REACTIONS
   6.1 Clinical Trial Experience
7. DRUG INTERACTIONS
   7.1 Effect of Other Drugs on ERLEADA
   7.2 Effect of ERLEADA on Other Drugs
8. USE IN SPECIFIC POPULATIONS
   8.1 Pregnancy
   8.2 Lactation
   8.3 Females and Males of Reproductive Potential
   8.4 Pediatric Use
   8.5 Geriatric Use
10. OVERDOSAGE
11. DESCRIPTION
12. CLINICAL PHARMACOLOGY
    12.1 Mechanism of Action
    12.2 Pharmacodynamics
    12.3 Pharmacokinetics
13. NONCLINICAL TOXICOLOGY
    13.1 Carcinogenesis, Mutagenesis, Impairment of Fertility
14. CLINICAL STUDIES
16. HOW SUPPLIED/STORAGE AND HANDLING
17. PATIENT COUNSELING INFORMATION

*Sections or subsections omitted from the full prescribing information are not listed.

FULL PRESCRIBING INFORMATION

1  INDICATIONS AND USAGE

ERLEADA is indicated for the treatment of patients with

- Metastatic castration-sensitive prostate cancer (mCSPC)
- Non-metastatic castration-resistant prostate cancer (nmCRPC)

2  DOSAGE AND ADMINISTRATION

2.1  Recommended Dosage

The recommended dose of ERLEADA is 240 mg (four 60 mg tablets) administered orally once daily. Swallow the tablets whole. ERLEADA can be taken with or without food.

Patients should also receive a gonadotropin-releasing hormone (GnRH) analog concurrently or should have had a bilateral orchiectomy.

2.2  Dose Modification

If a patient experiences a greater than or equal to Grade 3 toxicity or an intolerable side effect, hold dosing until symptoms improve to less than or equal to Grade 1 or original grade, then resume at the same dose or a reduced dose (180 mg or 120 mg), if warranted.

3  DOSAGE FORMS AND STRENGTHS

Tablets (60 mg): slightly yellowish to greyish green oblong film-coated tablets, debossed with "AR 60" on one side.

4  CONTRAINDICATIONS

None.

5  WARNINGS AND PRECAUTIONS

5.1  Ischemic Cardiovascular Events

Ischemic cardiovascular events, including events leading to death, occurred in patients receiving ERLEADA. Monitor for signs and symptoms of ischemic heart disease. Optimize management of cardiovascular risk factors, such as hypertension, diabetes, or dyslipidemia. Consider discontinuation of ERLEADA for Grade 3 and 4 events.

In a randomized study (SPARTAN) of patients with nmCRPC, ischemic cardiovascular events occurred in 4% of patients treated with ERLEADA and 3% of patients treated with placebo. In a randomized study (TITAN) in patients with mCSPC, ischemic cardiovascular events occurred in 4% of patients treated with ERLEADA and 2% of patients treated with placebo. Across the SPARTAN and TITAN studies, 6 patients (0.5%) treated with ERLEADA and 2 patients (0.2%) treated with placebo died from an ischemic cardiovascular event. Patients with current evidence of unstable angina, myocardial infarction, or congestive heart failure within six months of randomization were excluded from the SPARTAN and TITAN studies.

5.2 Fractures

Fractures occurred in patients receiving ERLEADA. Evaluate patients for fracture risk. Monitor and manage patients at risk for fractures according to established treatment guidelines and consider use of bone-targeted agents.

In a randomized study (SPARTAN) of patients with non-metastatic castration-resistant prostate cancer, fractures occurred in 12% of patients treated with ERLEADA and in 7% of patients treated with placebo. Grade 3-4 fractures occurred in 3% of patients treated with ERLEADA and in 1% of patients treated with placebo. The median time to onset of fracture was 314 days (range: 20 to 953 days) for patients treated with ERLEADA. Routine bone density assessment and treatment of osteoporosis with bone-targeted agents were not performed in the SPARTAN study.

In a randomized study (TITAN) of patients with metastatic castration-sensitive prostate cancer, fractures occurred in 9% of patients treated with ERLEADA and in 6% of patients treated with placebo. Grade 3-4 fractures were similar in both arms at 2%. The median time to onset of fracture was 56 days (range: 2 to 111 days) for patients treated with ERLEADA. Routine bone density assessment and treatment of osteoporosis with bone-targeted agents were not performed in the TITAN study.

5.3 Falls

Falls occurred in patients receiving ERLEADA with increased frequency in the elderly [See Use in Specific Populations (8.5)]. Evaluate patients for fall risk.

In a randomized study (SPARTAN), falls occurred in 16% of patients treated with ERLEADA compared to 9% of patients treated with placebo. Falls were not associated with loss of consciousness or seizure.

5.4 Seizure

Seizure occurred in patients receiving ERLEADA. Permanently discontinue ERLEADA in patients who develop a seizure during treatment. It is unknown whether anti-epileptic medications will prevent seizures with ERLEADA. Advise patients of the risk of developing a seizure while receiving ERLEADA and of engaging in any activity where sudden loss of consciousness could cause harm to themselves or others.

In two randomized studies (SPARTAN and TITAN), five patients (0.4%) treated with ERLEADA and one patient treated with placebo (0.1%) experienced a seizure. Seizure occurred from 159 to 650 days after initiation of ERLEADA. Patients with a history of seizure, predisposing factors for seizure, or receiving drugs known to decrease the seizure threshold or to induce seizure were excluded. There is no clinical experience in re-administering ERLEADA to patients who experienced a seizure.

5.5 Embryo-Fetal Toxicity

The safety and efficacy of ERLEADA have not been established in females. Based on its mechanism of action, ERLEADA can cause fetal harm and loss of pregnancy when administered to a pregnant female *[see Clinical Pharmacology (12.1)]*. Advise males with female partners of reproductive potential to use effective contraception during treatment and for 3 months after the last dose of ERLEADA *[see Use in Specific Populations (8.1, 8.3)]*.

6 ADVERSE REACTIONS

The following are discussed in more detail in other sections of the labeling:

- Ischemic Cardiovascular Events *[see Warnings and Precautions (5.1)]*.
- Fractures *[see Warnings and Precautions (5.2)]*.
- Falls *[see Warnings and Precautions (5.3)]*.
- Seizure *[see Warnings and Precautions (5.4)]*.

6.1 Clinical Trial Experience

Because clinical trials are conducted under widely varying conditions, adverse reaction rates observed in the clinical trials of a drug cannot be directly compared to rates in the clinical trials of another drug and may not reflect the rates observed in practice.

The most common adverse reactions ($\geq$ 10%) that occurred more frequently in the ERLEADA-treated patients ($\geq$ 2% over placebo) from the randomized placebo-controlled clinical trials (TITAN and SPARTAN) were fatigue, arthralgia, rash, decreased appetite, fall, weight decreased, hypertension, hot flush, diarrhea, and fracture.

<u>Metastatic Castration-sensitive Prostate Cancer (mCSPC)</u>

TITAN, a randomized (1:1), double-blind, placebo-controlled, multi-center clinical study, enrolled patients who had mCSPC. In this study, patients received either ERLEADA at a dose of 240 mg daily or placebo. All patients in the TITAN study received a concomitant gonadotropin-releasing hormone (GnRH) analog or had prior bilateral orchiectomy. The median duration of exposure was 20 months (range: 0 to 34 months) in patients who received ERLEADA and 18 months (range: 0.1 to 34 months) in patients who received placebo.

Ten patients (2%) who were treated with ERLEADA died from adverse reactions. The reasons for death were ischemic cardiovascular events (n=3), acute kidney injury (n=2), cardio-respiratory arrest (n=1), sudden cardiac death (n=1), respiratory failure (n=1), cerebrovascular accident (n=1), and large intestinal ulcer perforation (n=1). ERLEADA was discontinued due to adverse reactions in 8% of patients, most commonly from rash (2%). Adverse reactions leading to dose interruption or reduction of ERLEADA occurred in 23% of patients; the most frequent (>1%) were rash, fatigue, and hypertension. Serious adverse reactions occurred in 20% of ERLEADA-treated patients and 20% in patients receiving placebo.

Table 1 shows adverse reactions occurring in ≥10% on the ERLEADA arm in TITAN that occurred with a ≥2% absolute increase in frequency compared to placebo. Table 2 shows laboratory abnormalities that occurred in ≥15% of patients, and more frequently (>5%) in the ERLEADA arm compared to placebo.

Table 1: Adverse Reactions in TITAN (mCSPC)

| System/Organ Class<br>Adverse reaction | ERLEADA<br>N=524 | | Placebo<br>N=527 | |
|---|---|---|---|---|
| | All Grades<br>% | Grade 3-4<br>% | All Grades<br>% | Grade 3-4<br>% |
| General disorders and administration site conditions | | | | |
| Fatigue[1,3] | 26 | 3 | 25 | 2 |
| Musculoskeletal and connective tissue disorders | | | | |
| Arthralgia[3] | 17 | 0.4 | 15 | 0.9 |
| Skin and subcutaneous tissue disorders | | | | |
| Rash[2] | 28 | 6 | 9 | 0.6 |
| Pruritus | 11 | <1 | 5 | <1 |
| Vascular disorders | | | | |
| Hot flush | 23 | 0 | 16 | 0 |
| Hypertension | 18 | 8 | 16 | 9 |

[1] Includes fatigue and asthenia
[2] Includes rash, rash maculo-papular, rash generalized, urticaria, rash pruritic, rash macular, conjunctivitis, erythema multiforme, rash papular, skin exfoliation, genital rash, rash erythematous, stomatitis, drug eruption, mouth ulceration, rash pustular, blister, papule, pemphigoid, skin erosion, dermatitis, and rash vesicular
[3] Per the Common Terminology Criteria for Adverse Reactions (CTCAE), the highest severity for these events is Grade 3

Additional adverse reactions of interest occurring in 2%, but less than 10% of patients treated with ERLEADA included diarrhea (9% versus 6% on placebo), muscle spasm (3% versus 2% on placebo), dysgeusia (3% versus 1% on placebo), and hypothyroidism (4% versus 1% on placebo).

Table 2: Laboratory Abnormalities Occurring in ≥ 15% of ERLEADA-Treated Patients and at a Higher Incidence than Placebo (Between Arm Difference > 5% All Grades) in TITAN (mCSPC)

| Laboratory Abnormality | ERLEADA<br>N=524 | | Placebo<br>N=527 | |
|---|---|---|---|---|
| | All Grades<br>% | Grade 3-4<br>% | All Grades<br>% | Grade 3-4<br>% |
| Hematology | | | | |
| White blood cell decreased | 27 | 0.4 | 19 | 0.6 |
| Chemistry | | | | |
| Hypertriglyceridemia[1] | 17 | 3 | 12 | 2 |

[1] Does not reflect fasting values

Non-metastatic Castration-resistant Prostate Cancer (nmCRPC)

SPARTAN, a randomized (2:1), double-blind, placebo-controlled, multi-center clinical study, enrolled patients who had nmCRPC. In this study, patients received either ERLEADA at a dose of 240 mg daily or a placebo. All patients in the SPARTAN study received a concomitant gonadotropin-releasing hormone (GnRH) analog or had a bilateral orchiectomy. The median duration of exposure was 16.9 months (range: 0.1 to 42 months) in patients who received ERLEADA and 11.2 months (range: 0.1 to 37 months) in patients who received placebo.

Eight patients (1%) who were treated with ERLEADA died from adverse reactions. The reasons for death were infection (n=4), myocardial infarction (n=3), and cerebral hemorrhage (n=1). One patient (0.3%) treated with placebo died from an adverse reaction of cardiopulmonary arrest (n=1). ERLEADA was discontinued due to adverse reactions in 11% of patients, most commonly from rash (3%). Adverse reactions leading to dose interruption or reduction of ERLEADA occurred in 33% of patients; the most common (>1%) were rash, diarrhea, fatigue, nausea, vomiting, hypertension, and hematuria. Serious adverse reactions occurred in 25% of ERLEADA-treated patients and 23% in patients receiving placebo. The most frequent serious adverse reactions (>2%) were fracture (3%) in the ERLEADA arm and urinary retention (4%) in the placebo arm.

Table 3 shows adverse reactions occurring in ≥10% on the ERLEADA arm in SPARTAN that occurred with a ≥2% absolute increase in frequency compared to placebo. Table 4 shows laboratory abnormalities that occurred in ≥15% of patients, and more frequently (>5%) in the ERLEADA arm compared to placebo.

Table 3: Adverse Reactions in SPARTAN (nmCRPC)

| System/Organ Class<br>Adverse reaction | ERLEADA N=803 All Grades % | ERLEADA N=803 Grade 3-4 % | Placebo N=398 All Grades % | Placebo N=398 Grade 3-4 % |
|---|---|---|---|---|
| General disorders and administration site conditions | | | | |
| Fatigue[1,4] | 39 | 1 | 28 | 0.3 |
| Musculoskeletal and connective tissue disorders | | | | |
| Arthralgia[1] | 16 | 0 | 8 | 0 |
| Skin and subcutaneous tissue disorders | | | | |
| Rash[2] | 25 | 5 | 6 | 0.3 |
| Metabolism and nutrition disorders | | | | |
| Decreased appetite[1] | 12 | 0.1 | 9 | 0 |
| Peripheral edema[1] | 11 | 0 | 9 | 0 |
| Injury, poisoning and procedural complications | | | | |
| Fall[1] | 16 | 2 | 9 | 0.8 |
| Fracture[1] | 12 | 3 | 7 | 0.8 |
| Investigations | | | | |
| Weight decreased[1] | 16 | 1 | 6 | 0.3 |
| Vascular disorders | | | | |
| Hypertension | 25 | 14 | 20 | 12 |
| Hot flush | 14 | 0 | 9 | 0 |
| Gastrointestinal disorders | | | | |
| Diarrhea | 20 | 1 | 15 | 0.5 |
| Nausea | 18 | 0 | 16 | 0 |

1 Includes fatigue and asthenia.
2 Includes rash, rash maculo-papular, rash generalized, urticaria, rash pruritic, rash macular, conjunctivitis, erythema multiforme, rash papular, skin exfoliation, genital rash, rash erythematous, dermatitis, drug eruption, mouth ulceration, rash pustular, blister, papule, pemphigoid, skin erosion, dermatitis, and rash vesicular.
3 Includes rib fracture, lumbar vertebral fracture, spinal compression fracture, spinal fracture, foot fracture, hip fracture, humerus fracture, thoracic vertebral fracture, upper limb fracture, fractured sacrum, hand fracture, pubis fracture, acetabulum fracture, ankle fracture, compression fracture, costal cartilage fracture, facial bones fracture, lower limb fracture, osteoporotic fracture, wrist fracture, avulsion fracture, fibula fracture, fractured coccyx, pelvic fracture, radius fracture, sternal fracture, stress fracture, traumatic fracture, cervical vertebral fracture, femoral neck fracture, and tibia fracture.
4 Per the Common Terminology Criteria for Adverse Reactions (CTCAE), the highest severity for these events is Grade 3.
5 Includes appetite disorder, decreased appetite, early satiety, and hypophagia.
6 Includes peripheral edema, generalized edema, edema, edema genital, penile edema, peripheral swelling, scrotal edema, lymphedema, swelling, and localized edema.

Additional clinically significant adverse reactions occurring in 2% or more of patients treated with ERLEADA included hypothyroidism (8.1% versus 2% on placebo), pruritus (6.2% versus 2% on placebo), and heart failure (2.2% versus 1% on placebo).

Table 4: Laboratory Abnormalities Occurring in ≥ 15% of ERLEADA-Treated Patients and at a Higher Incidence than Placebo (Between Arm Difference > 5% All Grades) in SPARTAN (nmCRPC)

| Laboratory Abnormality | ERLEADA N=803 | | Placebo N=398 | |
|---|---|---|---|---|
| | All Grades % | Grade 3-4 % | All Grades % | Grade 3-4 % |
| Hematology | | | | |
| Anemia | 70 | 0.4 | 64 | 0.5 |
| Leukopenia | 47 | 0.3 | 29 | 0 |
| Lymphopenia | 41 | 2 | 21 | 2 |
| Chemistry | | | | |
| Hypercholesterolemia¹ | 76 | 0.1 | 46 | 0 |
| Hyperglycemia¹ | 70 | 2 | 59 | 1 |
| Hypertriglyceridemia¹ | 67 | 2 | 49 | 0.8 |
| Hyperkalemia | 32 | 2 | 22 | 0.5 |

¹ Does not reflect fasting values.

Rash

In the combined data of two randomized, placebo-controlled clinical studies, rash associated with ERLEADA was most commonly described as macular or maculo-papular. Adverse reactions of rash were reported for 26% of patients treated with ERLEADA versus 8% of patients treated with placebo. Grade 3 rashes (defined as covering > 30% body surface area [BSA]) were reported with ERLEADA treatment (6%) versus placebo (0.5%).

The onset of rash occurred at a median of 83 days of ERLEADA treatment. Rash resolved in 78% of patients within a median of 78 days from onset of rash. Rash was commonly managed with oral antihistamines, topical corticosteroids, and 19% of patients received systemic corticosteroids. Dose reduction or dose interruption occurred in 14% and 28% of patients, respectively. Of the patients who had dose interruption, 59% experienced recurrence of rash upon reintroduction of ERLEADA.

Hypothyroidism

In the combined data of two randomized, placebo-controlled clinical studies, hypothyroidism was reported for 8% of patients treated with ERLEADA and 2% of patients treated with placebo based on assessments of thyroid-stimulating hormone (TSH) every 4 months. Elevated TSH occurred in 25% of patients treated with ERLEADA and 7% of patients treated with placebo. The median onset was at the first scheduled assessment. There were no Grade 3 or 4 adverse reactions. Thyroid replacement therapy was initiated in 5% of patients treated with ERLEADA. Thyroid replacement therapy, when clinically indicated, should be initiated or dose-adjusted *[see Drug Interactions (7.2)]*.

7  DRUG INTERACTIONS

7.1  Effect of Other Drugs on ERLEADA

Strong CYP2C8 or CYP3A4 Inhibitors

Co-administration of a strong CYP2C8 or CYP3A4 inhibitor is predicted to increase the steady-state exposure of the active moieties (sum of unbound apalutamide plus the potency-adjusted unbound N-desmethyl-apalutamide). No initial dose adjustment is necessary however, reduce the ERLEADA dose based on tolerability *[see Dosage and Administration (2.2)]*. Mild or moderate inhibitors of CYP2C8 or CYP3A4 are not expected to affect the exposure of apalutamide.

7.2  Effect of ERLEADA on Other Drugs

CYP3A4, CYP2C9, CYP2C19 and UGT Substrates

ERLEADA is a strong inducer of CYP3A4 and CYP2C19, and a weak inducer of CYP2C9 in humans. Concomitant use of ERLEADA with medications that are primarily metabolized by CYP3A4, CYP2C19, or CYP2C9 can result in lower exposure to these medications. Substitution for these medications is recommended when possible or evaluate for loss of activity if medication is continued. Concomitant administration of ERLEADA with medications that are substrates of UDP-glucuronosyl transferase (UGT) can result in decreased exposure. Use caution if substrates of UGT must be co-administered with ERLEADA and evaluate for loss of activity *[see Clinical Pharmacology (12.3)]*.

P-gp, BCRP or OATP1B1 Substrates

Apalutamide was shown to be a weak inducer of P-glycoprotein (P-gp), breast cancer resistance protein (BCRP), and organic anion transporting polypeptide 1B1 (OATP1B1) clinically. At steady-state, apalutamide reduced the plasma exposure to fexofenadine (a P-gp substrate) and rosuvastatin (a BCRP/OATP1B1 substrate). Concomitant use of ERLEADA with medications that are substrates of P-gp, BCRP, or OATP1B1 can result in lower exposure of these medications. Use caution if substrates of P-gp, BCRP or OATP1B1 must be co-administered with ERLEADA and evaluate for loss of activity if medication is continued *[see Clinical Pharmacology (12.3)]*.

8 USE IN SPECIFIC POPULATIONS

8.1 Pregnancy

Risk Summary

The safety and efficacy of ERLEADA have not been established in females. Based on its mechanism of action, ERLEADA can cause fetal harm and loss of pregnancy *[see Clinical Pharmacology (12.1)]*. There are no human data on the use of ERLEADA in pregnant women. ERLEADA is not indicated for use in females, so animal embryo-fetal developmental toxicology studies were not conducted with apalutamide.

8.2 Lactation

Risk Summary

The safety and efficacy of ERLEADA have not been established in females. There are no data on the presence of apalutamide or its metabolites in human milk, the effect on the breastfed child, or the effect on milk production.

8.3 Females and Males of Reproductive Potential

Contraception

*Males*

Based on the mechanism of action and findings in an animal reproduction study, advise male patients with female partners of reproductive potential to use effective contraception during treatment and for 3 months after the last dose of ERLEADA *[see Use in Specific Populations (8.1)]*.

Infertility

*Males*

Based on animal studies, ERLEADA may impair fertility in males of reproductive potential *[see Nonclinical Toxicology (13.1)]*.

8.4 Pediatric Use

Safety and effectiveness of ERLEADA in pediatric patients have not been established.

8.5 Geriatric Use

Of the 1327 patients who received ERLEADA in clinical studies, 19% of patients were less than 65 years, 41% of patients were 65 years to 74 years, and 40% were 75 years and over.

No overall differences in effectiveness were observed between older and younger patients.

Of patients treated with ERLEADA (n=1073), Grade 3-4 adverse reactions occurred in 39% of patients younger than 65 years, 41% of patients 65-74 years, and 49% of patients 75 years or older. Falls in patients receiving ERLEADA with androgen deprivation therapy was elevated in the elderly, occurring in 8% of patients younger than 65 years, 10% of patients 65-74 years, and 19% of patients 75 years or older.

10  OVERDOSAGE

There is no known specific antidote for apalutamide overdose. In the event of an overdose, stop ERLEADA, undertake general supportive measures until clinical toxicity has been diminished or resolved.

11  DESCRIPTION

Apalutamide, the active ingredient of ERLEADA, is an androgen receptor inhibitor. The chemical name is (4-[7-(6-Cyano-5-trifluoromethylpyridin-3-yl)-8-oxo-6-thioxo-5,7-diazaspiro[3.4]oct-5-yl]-2-fluoro-N-methylbenzamide). Apalutamide is a white to slightly yellow powder. Apalutamide is practically insoluble in aqueous media over a wide range of pH values.

The molecular weight is 477.44 and molecular formula is $C_{21}H_{15}F_4N_5O_2S$. The structural formula is:

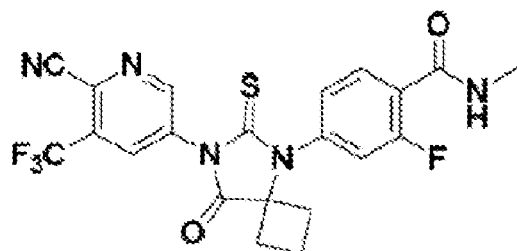

ERLEADA (apalutamide) is supplied as film-coated tablets for oral administration containing 60 mg of apalutamide. Inactive ingredients of the core tablet are: colloidal anhydrous silica, croscarmellose sodium, hydroxypropyl methylcellulose-acetate succinate, magnesium stearate, microcrystalline cellulose, and silicified microcrystalline cellulose.

The tablets are finished with a commercially available film-coating comprising the following excipients: iron oxide black, iron oxide yellow, polyethylene glycol, polyvinyl alcohol, talc, and titanium dioxide.

12  CLINICAL PHARMACOLOGY

12.1  Mechanism of Action

Apalutamide is an Androgen Receptor (AR) inhibitor that binds directly to the ligand-binding domain of the AR. Apalutamide inhibits AR nuclear translocation, inhibits DNA binding, and impedes AR-mediated transcription. A major metabolite, N-desmethyl apalutamide, is a less potent inhibitor of AR, and exhibited one-third the activity of apalutamide in an *in vitro* transcriptional reporter assay. Apalutamide administration caused decreased tumor cell proliferation and increased apoptosis leading to decreased tumor volume in mouse xenograft models of prostate cancer.

12.2 Pharmacodynamics

Cardiac Electrophysiology

The effect of apalutamide 240 mg once daily on the QTc interval was assessed in an open-label, uncontrolled, multi-center, single-arm dedicated QT study in 45 patients with CRPC. The maximum mean QTcF change from baseline was 12.4 ms (2-sided 90% upper CI: 16.0 ms). An exposure-QT analysis suggested a concentration-dependent increase in QTcF for apalutamide and its active metabolite.

12.3 Pharmacokinetics

Apalutamide pharmacokinetic parameters are presented as the mean [standard deviation (SD)] unless otherwise specified. Apalutamide $C_{max}$ and area under the concentration curve (AUC) increased proportionally following repeated once-daily dosing of 30 to 480 mg (0.125 to 2 times the recommended dosage). Following administration of the recommended dosage, apalutamide steady-state was achieved after 4 weeks and the mean accumulation ratio was approximately 5-fold. Apalutamide $C_{max}$ was 6.0 mcg/mL (1.7) and AUC was 100 mcg·h/mL (32) at steady-state. Daily fluctuations in apalutamide plasma concentrations were low, with mean peak-to-trough ratio of 1.63. An increase in apparent clearance (CL/F) was observed with repeat dosing, likely due to induction of apalutamide's own metabolism. The auto-induction effect likely reached its maximum at the recommended dosage because exposure of apalutamide across the dose range of 30 to 480 mg is dose-proportional.

The major active metabolite N-desmethyl apalutamide $C_{max}$ was 5.9 mcg/mL (1.0) and AUC was 124 mcg·h/mL (23) at steady-state after the recommended dosage. N-desmethyl apalutamide was characterized by a flat concentration-time profile at steady-state with a mean peak-to-trough ratio of 1.27. Mean AUC metabolite/parent drug ratio for N-desmethyl apalutamide following repeat-dose administration was 1.3. Based on systemic exposure, relative potency, and pharmacokinetic properties, N-desmethyl apalutamide likely contributed to the clinical activity of apalutamide.

Absorption

Mean absolute oral bioavailability was approximately 100%. Median time to achieve peak plasma concentration ($t_{max}$) was 2 hours (range: 1 to 5 hours).

Effect of Food

Administration of apalutamide to healthy subjects under fasting conditions and with a high-fat meal (approximately 500 to 600 fat calories, 250 carbohydrate calories, and 150 protein calories) resulted in no clinically relevant changes in $C_{max}$ and AUC. Median time to reach $t_{max}$ was delayed approximately 2 hours with food.

Distribution

The mean apparent volume of distribution at steady-state of apalutamide was approximately 276 L.

Apalutamide was 96% and N-desmethyl apalutamide was 95% bound to plasma proteins with no concentration dependency.

Elimination

The CL/F of apalutamide was 1.3 L/h after single dosing and increased to 2.0 L/h at steady-state after once-daily dosing likely due to CYP3A4 auto-induction. The mean effective half-life for apalutamide in patients was approximately 3 days at steady-state.

Metabolism

Metabolism is the main route of elimination of apalutamide. Apalutamide is primarily metabolized by CYP2C8 and CYP3A4 to form active metabolite, N-desmethyl apalutamide. The contribution of CYP2C8 and CYP3A4 in the metabolism of apalutamide is estimated to be 58% and 13% following single dose but changes to 40% and 37%, respectively at steady-state.

Apalutamide represented 45% and N-desmethyl apalutamide represented 44% of the total AUC following a single oral administration of radiolabeled apalutamide 240 mg.

Excretion

Up to 70 days following a single oral administration of radiolabeled apalutamide, 65% of the dose was recovered in urine (1.2% of dose as unchanged apalutamide and 2.7% as N-desmethyl apalutamide) and 24% was recovered in feces (1.5% of dose as unchanged apalutamide and 2% as N-desmethyl apalutamide).

Specific Populations

No clinically significant differences in the pharmacokinetics of apalutamide or N-desmethyl apalutamide were observed based on age (18-94 years), race (Black, non-Japanese Asian, Japanese), mild to moderate (eGFR 30-89 mL/min/1.73m$^2$, estimated by the modification of diet in renal disease [MDRD] equation) renal impairment, or mild (Child-Pugh A) to moderate (Child-Pugh B) hepatic impairment.

The effect of severe renal impairment or end stage renal disease (eGFR ≤29 mL/min/1.73m$^2$, MDRD) or severe hepatic impairment (Child-Pugh C) on apalutamide pharmacokinetics is unknown.

Drug Interactions

Effect of Other Drugs on ERLEADA

Strong CYP2C8 Inhibitors

Apalutamide $C_{max}$ decreased by 21% while AUC increased by 68% following co-administration of ERLEADA as a 240 mg single dose with gemfibrozil (a strong CYP2C8 inhibitor). Gemfibrozil is predicted to increase the steady-state apalutamide $C_{max}$ by 32% and AUC by 44%. For the active moieties (sum of unbound apalutamide plus the potency-adjusted unbound N-desmethyl apalutamide), the predicted steady-state $C_{max}$ increased by 19% and AUC by 23%.

Strong CYP3A4 Inhibitors

Apalutamide $C_{max}$ decreased by 22% while AUC was similar following co-administration of ERLEADA as a 240 mg single dose with itraconazole (a strong CYP3A4 inhibitor). Ketoconazole (a strong CYP3A4 inhibitor) is predicted to increase the single-dose apalutamide AUC by 24% but have no impact on $C_{max}$. Ketoconazole is predicted to increase the steady-state apalutamide $C_{max}$ by 38% and AUC by 51%. For the active moieties, the predicted steady-state $C_{max}$ increased by 23% and AUC by 28%.

CYP3A4/CYP2C8 Inducers

Rifampin (a strong CYP3A4 and moderate CYP2C8 inducer) is predicted to decrease the steady-state apalutamide $C_{max}$ by 25% and AUC by 34%. For the active moieties, the predicted steady-state $C_{max}$ decreased by 15% and AUC by 19%.

Acid lowering agents

Apalutamide is not ionizable under relevant physiological pH condition, therefore acid lowering agents (e.g. proton pump inhibitor, $H_2$-receptor antagonist, antacid) are not expected to affect the solubility and bioavailability of apalutamide.

Drugs affecting transporters

In vitro, apalutamide and N-desmethyl apalutamide are substrates for P-gp but not BCRP, OATP1B1, and OATP1B3. Because apalutamide is completely absorbed after oral administration, P-gp does not limit the absorption of apalutamide and therefore, inhibition or induction of P-gp is not expected to affect the bioavailability of apalutamide.

Effect of ERLEADA on Other Drugs

CYP substrates

In vitro studies showed that apalutamide and N-desmethyl apalutamide are moderate to strong CYP3A4 and CYP2B6 inducers, are moderate inhibitors of CYP2B6 and CYP2C8, and weak inhibitors of CYP2C9, CYP2C19, and CYP3A4. Apalutamide and N-desmethyl apalutamide do not affect CYP1A2 and CYP2D6 at therapeutically relevant concentrations.

Co-administration of ERLEADA with single oral doses of sensitive CYP substrates resulted in a 92% decrease in the AUC of midazolam (a CYP3A4 substrate), 85% decrease in the AUC of omeprazole (a CYP2C19 substrate), and 46% decrease in the AUC of S-warfarin (a CYP2C9 substrate). ERLEADA did not cause clinically significant changes in exposure to a CYP2C8 substrate.

P-gp, BCRP and OATP1B1 substrates

Co-administration of ERLEADA with single oral doses of transporter substrates resulted in a 30% decrease in the AUC of fexofenadine (a P-gp substrate) and 41% decrease in the AUC of rosuvastatin (a BCRP/OATP1B1 substrate) but had no impact on $C_{max}$.

UGT substrates

Apalutamide may induce UGT. Concomitant administration of ERLEADA with medications that are substrates of UGT may result in lower exposure to these medications.

*OCT2, OAT1, OAT3 and MATEs substrates*

In vitro, apalutamide and N-desmethyl apalutamide inhibit organic cation transporter 2 (OCT2), organic anion transporter 3 (OAT3) and multidrug and toxin extrusions (MATEs), and do not inhibit organic anion transporter 1. Apalutamide is not predicted to cause clinically significant changes in exposure to an OAT3 substrate.

*GnRH Analog*

In mCSPC subjects receiving leuprolide acetate (a GnRH analog) co-administered with apalutamide, PK data indicated that apalutamide had no apparent effect on the steady-state exposure of leuprolide.

13 NONCLINICAL TOXICOLOGY

13.1 Carcinogenesis, Mutagenesis, Impairment of Fertility

Long-term animal studies have not been conducted to evaluate the carcinogenic potential of apalutamide. Apalutamide did not induce mutations in the bacterial reverse mutation (Ames) assay and was not genotoxic in either *in vitro* chromosome aberration assay or the *in vivo* rat bone marrow micronucleus assay or the *in vivo* rat Comet assay.

In repeat-dose toxicity studies in male rats (up to 26 weeks) and dogs (up to 39 weeks), atrophy of the prostate gland and seminal vesicles, aspermia/hypospermia, tubular degeneration and/or hyperplasia or hypertrophy of the interstitial cells in the reproductive system were observed at ≥ 25 mg/kg/day in rats (1.4 times the human exposure based on AUC) and ≥ 2.5 mg/kg/day in dogs (0.9 times the human exposure based on AUC).

In a fertility study in male rats, a decrease in sperm concentration and motility, increased abnormal sperm morphology, lower copulation and fertility rates (upon pairing with untreated females) along with reduced weights of the secondary sex glands and epididymis were observed following 4 weeks of dosing at ≥ 25 mg/kg/day (0.8 times the human exposure based on AUC). A reduced number of live fetuses due to increased pre- and/or post-implantation loss was observed following 4 weeks of 150 mg/kg/day administration (5.7 times the human exposure based on AUC). Effects on male rats were reversible after 8 weeks from the last apalutamide administration.

14 CLINICAL STUDIES

The efficacy and safety of ERLEADA was established in two randomized placebo-controlled clinical trials.

<u>TITAN (NCT02489318): Metastatic Castration-sensitive Prostate Cancer (mCSPC)</u>

TITAN was a randomized, double-blind, placebo-controlled, multinational, clinical trial in which 1052 patients with mCSPC were randomized (1:1) to receive either ERLEADA orally at a dose of 240 mg once daily (N = 525) or placebo once daily (N = 527). All patients in the TITAN trial received concomitant GnRH analog or had prior bilateral orchiectomy. Patients were stratified by Gleason score at diagnosis, prior docetaxel use, and region of the world. Patients with both high- and low-volume mCSPC were eligible for the study. High volume of disease was defined as metastases involving the viscera with 1 bone lesion or the presence of 4 or more bone lesions, at least 1 of which must be in a bony structure beyond the vertebral column and pelvic bones.

The following patient demographics and baseline disease characteristics were balanced between the treatment arms. The median age was 68 years (range 43-94) and 23% of patients were 75 years of age or older. The racial distribution was 68% Caucasian, 22% Asian, and 2% Black. Sixty-three percent (63%) of patients had high-volume disease and 37% had low-volume disease. Sixteen percent (16%) of patients had prior surgery, radiotherapy of the prostate or both. A majority of patients had a Gleason score of 8 or higher (67%). Sixty-eight percent (68%) of patients received prior treatment with an anti-androgen (bicalutamide, flutamide, or nilutamide). All patients except one in the placebo group, had an Eastern Cooperative Oncology Group Performance Status (ECOG PS) score of 0 or 1 at study entry.

The major efficacy outcome measures of the study were overall survival (OS) and radiographic progression-free survival (rPFS). Radiographic progression-free survival was based on investigator assessment and was defined as time from randomization to radiographic disease progression or death. Radiographic disease progression was defined by identification of 2 or more new bone lesions on a bone scan with confirmation (Prostate Cancer Working Group 2 criteria) and/or progression in soft tissue disease.

A statistically significant improvement in OS and rPFS was demonstrated in patients randomized to receive ERLEADA compared with patients randomized to receive placebo. The results for OS are based upon a prespecified interim efficacy analysis. Efficacy results of TITAN are summarized in Table 5 and Figures 1 and 2.

Table 5: Summary of Efficacy Results – Intent-to-treat mCSPC Population (TITAN)

| Endpoint | ERLEADA N=525 | Placebo N=527 |
| --- | --- | --- |
| Overall Survival[a] | | |
| Deaths (%) | 83 (16%) | 117 (22%) |
| Median, months (95% CI)[d] | NE (NE, NE) | NE (NE, NE) |
| Hazard ratio (95% CI)[b] | 0.67 (0.51, 0.89) | |
| p-value[c] | 0.0053 | |
| Radiographic Progression-free Survival | | |
| Disease progression or death (%) | 134 (26%) | 231 (44%) |
| Median, months (95% CI)[d] | NE (NE, NE) | 22.1 (18, 33) |
| Hazard ratio (95% CI)[b] | 0.48 (0.39, 0.60) | |
| p-value[c] | <0.0001 | |

[a] Interim analysis is based on 50% of the number of events planned for the final analysis. Allocated alpha = 0.01
[b] Hazard ratio is from stratified proportional hazards model. Hazard ratio <1 favors ERLEADA
[c] p-value is from the log-rank test stratified by Gleason score at diagnosis (≤7 vs. >7), Region (NA/EU vs. Other Countries) and Prior docetaxel use (Yes vs. No)
[d] NE=Not Estimable Consistent improvement in rPFS was observed across the following patient subgroups: disease volume (high vs low), prior docetaxel use (yes or no), and Gleason score at diagnosis (≤7 vs. >7).

Consistent improvement in OS was observed across the following patient subgroups: disease volume (high vs low) and Gleason score at diagnosis (≤7 vs. >7).
Treatment with ERLEADA statistically significantly delayed the initiation of cytotoxic chemotherapy (HR = 0.39, 95% CI = 0.27, 0.56; p < 0.0001).
Figure 1: Kaplan-Meier Plot of Overall Survival (OS); Intent-to-treat mCSPC Population (TITAN)
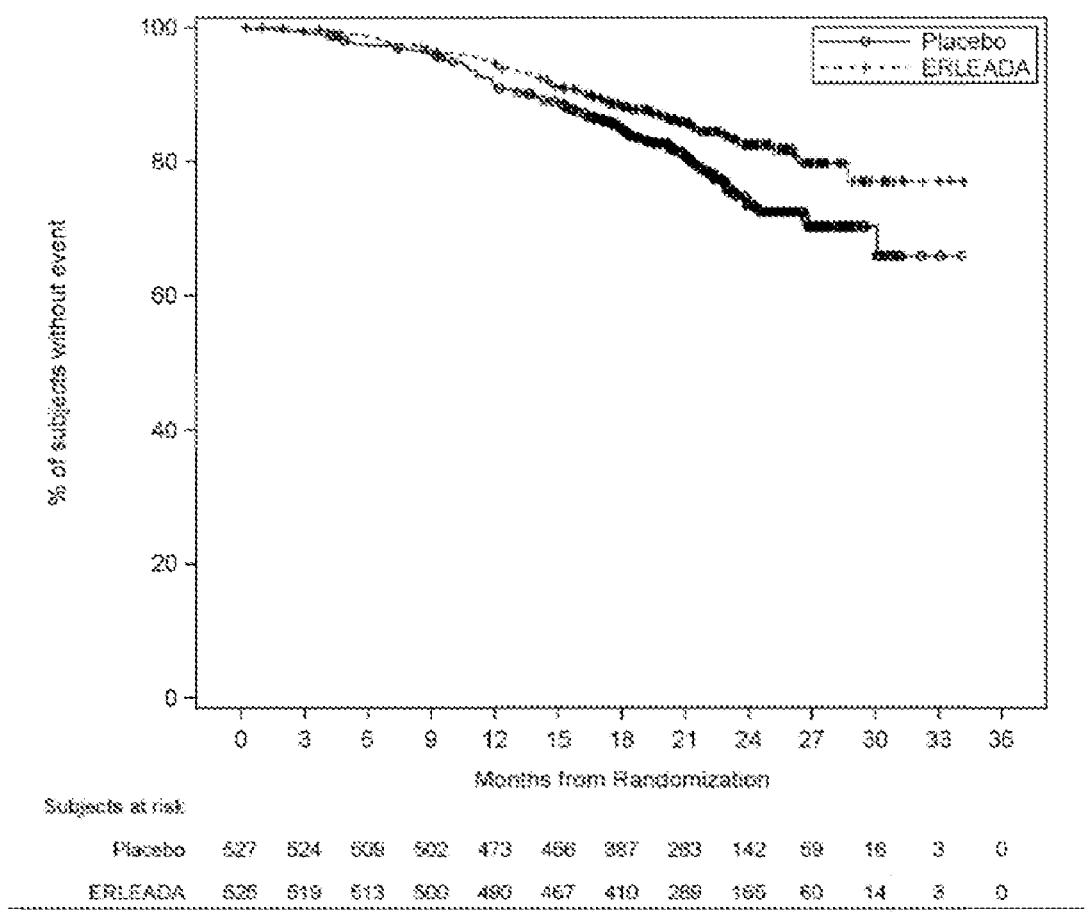

Figure 2: Kaplan-Meier Plot of Radiographic Progression-Free Survival (rPFS); Intent-to-treat mCSPC Population (TITAN)

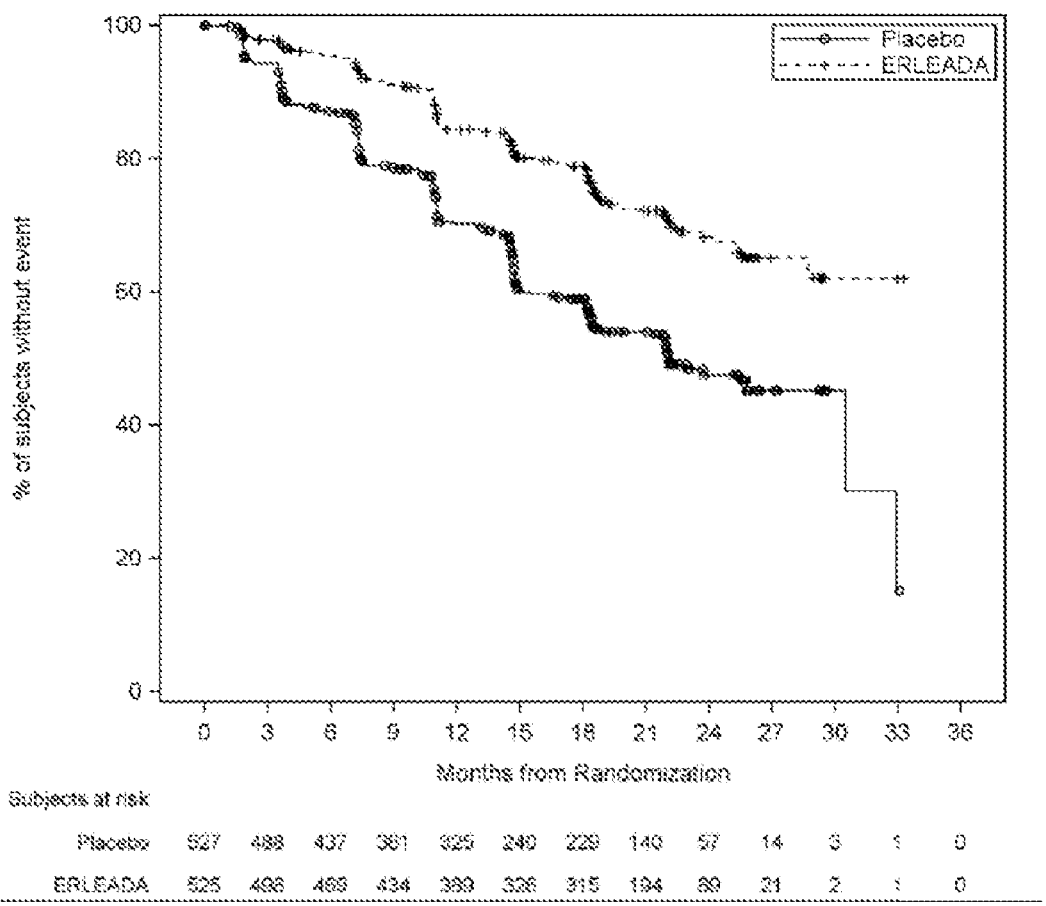

SPARTAN (NCT01946204): Non-metastatic, Castration-resistant Prostate Cancer (nmCRPC)

SPARTAN was a multicenter, double-blind, randomized (2:1), placebo-controlled clinical trial in which 1207 patients with nmCRPC were randomized (2:1) to receive either ERLEADA orally at a dose of 240 mg once daily (N = 806) or placebo once daily (N = 401). All patients in the SPARTAN trial received a concomitant GnRH analog or had a bilateral orchiectomy. Patients were stratified by Prostate Specific Antigen (PSA) Doubling Time (PSADT), the use of bone-sparing agents, and locoregional disease. Patients were required to have a PSADT ≤ 10 months and confirmation of non-metastatic disease by blinded independent central review (BICR). PSA results were blinded and were not used for treatment discontinuation. Patients randomized to either arm discontinued treatment for radiographic disease progression confirmed by BICR, locoregional-only progression, initiation of new treatment, unacceptable toxicity, or withdrawal.

The following patient demographics and baseline disease characteristics were balanced between the treatment arms. The median age was 74 years (range 48-97) and 26% of patients were 80 years of age or older. The racial distribution was 66% Caucasian, 12% Asian, and 6% Black. Seventy-seven percent (77%) of patients in both treatment arms had prior surgery or radiotherapy of the prostate. A majority of patients had a Gleason score of 7 or higher (78%). Fifteen percent (15%) of patients had <2 cm pelvic lymph nodes at study entry. Seventy-three percent (73%) of patients received prior treatment with an anti-androgen; 69% of patients received bicalutamide and 10% of patients received flutamide. All patients had an Eastern Cooperative Oncology Group Performance Status (ECOG PS) score of 0 or 1 at study entry. Among the patients who discontinued study treatment (N = 279 for placebo and N = 314 for ERLEADA), a greater proportion (80%) of patients treated with placebo received subsequent therapy compared to patients treated with ERLEADA (56%). Locoregional-only progression occurred in 2% of patients overall.

The major efficacy outcome measure of the study was metastasis-free survival (MFS), defined as the time from randomization to the time of first evidence of BICR-confirmed distant metastasis, defined as new bone or soft tissue lesions or enlarged lymph nodes above the iliac bifurcation, or death due to any cause, whichever occurred first. Additional efficacy endpoints were time to metastasis (TTM), progression-free survival (PFS) which also includes locoregional progression, time to symptomatic progression, and overall survival (OS).

A statistically significant improvement in MFS was demonstrated in patients randomized to receive ERLEADA compared with patients randomized to receive placebo. Consistent results were observed across patient subgroups including PSADT (≤ 6 months or > 6 months), use of a prior bone-sparing agent (yes or no), and locoregional disease (N0 or N1). The major efficacy outcome was supported by statistically significant improvements in TTM, PFS, and time to symptomatic progression. Overall survival (OS) data were not mature at the time of final MFS analysis (24% of the required number of events). The efficacy results of MFS, TTM, and PFS from SPARTAN are summarized in Figure 3 and Table 6.

Figure 3: Kaplan-Meier Metastasis-Free Survival (MFS) Curve in SPARTAN (nmCRPC)

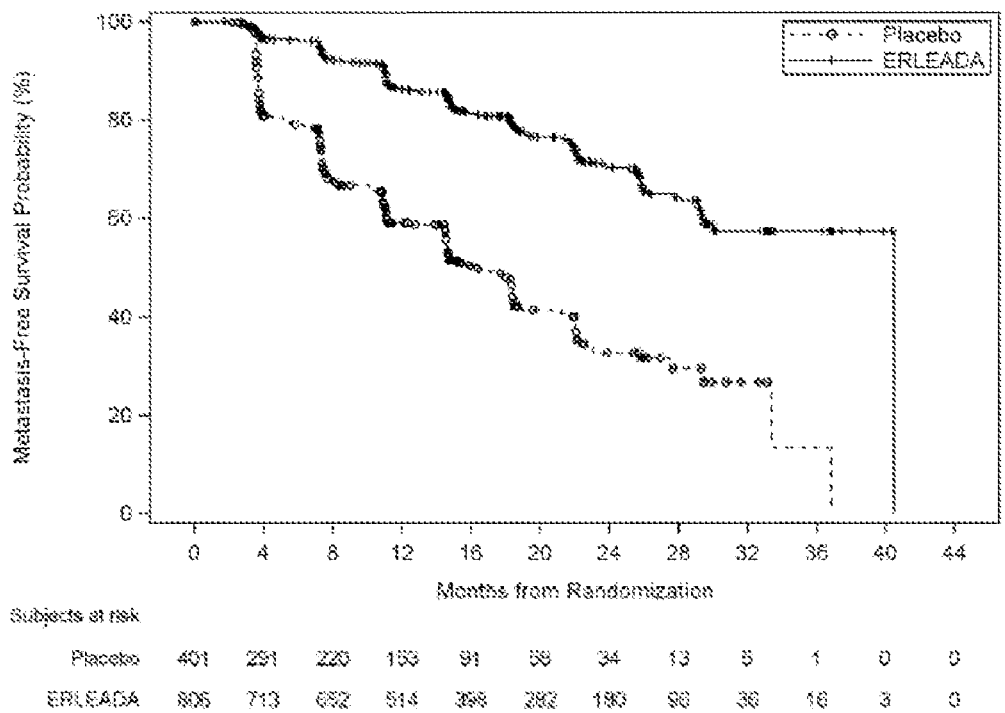

Table 6: BICR-assessed Efficacy Results (SPARTAN)

| Endpoint | Number of Events (%) | | Median [Months (95% CI)] | | HR (95% CI) p-value (log-rank test)[a] |
|---|---|---|---|---|---|
| | ERLEADA (N=806) | Placebo (N=401) | ERLEADA | Placebo | |
| Metastasis Free Survival | 184 (23%) | 194 (48%) | 40.5 (NE, NE) | 16.2 (14, 18) | 0.28 (0.23, 0.35) <0.0001 |
| Time to Metastasis | 175 (22%) | 191 (48%) | 40.5 (NE, NE) | 16.6 (15, 18) | 0.27 (0.22, 0.34) <0.0001 |
| Progression-Free Survival | 200 (25%) | 204 (51%) | 40.5 (NE, NE) | 14.7 (14, 18) | 0.29 (0.24, 0.36) <0.0001 |

[a] All analyses stratified by PSA doubling time, bone-sparing agent use, and locoregional disease status.
NE=Not Estimable

16 HOW SUPPLIED/STORAGE AND HANDLING

ERLEADA (apalutamide) 60 mg film-coated tablets are slightly yellowish to greyish green, oblong-shaped tablets debossed with "AR 60" on one side. ERLEADA 60 mg tablets are available in bottles of 120 tablets. Each bottle contains silica gel desiccant.

NDC Number        59676-600-12

Storage and Handling

Store at 20°C to 25°C (68°F to 77°F); excursions permitted to 15°C to 30°C (59°F to 86°F) *[see USP Controlled Room Temperature]*.

Store in the original package. Do not discard desiccant. Protect from light and moisture.

17 PATIENT COUNSELING INFORMATION

*Advise the patient to read the FDA-approved patient labeling (Patient Information).*

Ischemic Cardiovascular Events

- Inform patients that ERLEADA has been associated with ischemic cardiovascular events. Advise patients to seek immediate medical attention if any symptoms suggestive of a cardiovascular event occur *[see Warnings and Precautions (5.1)]*.

Falls and Fractures

- Inform patients that ERLEADA is associated with an increased incidence of falls and fractures *[see Warnings and Precautions (5.2, 5.3)]*.

Seizures

- Inform patients that ERLEADA has been associated with an increased risk of seizure. Discuss conditions that may predispose to seizures and medications that may lower the seizure threshold. Advise patients of the risk of engaging in any activity where sudden loss of consciousness could cause serious harm to themselves or others. Inform patients to contact their healthcare provider right away if they experience a seizure *[see Warnings and Precautions (5.4)]*.

Rash

- Inform patients that ERLEADA is associated with rashes and to inform their healthcare provider if they develop a rash *[see Adverse Reactions (6.1)]*.

Dosage and Administration

- Inform patients receiving concomitant gonadotropin-releasing hormone (GnRH) analog therapy that they need to maintain this treatment during the course of treatment with ERLEADA.

- Instruct patients to take their dose at the same time each day (once daily). ERLEADA can be taken with or without food. Each tablet should be swallowed whole.

- Inform patients that in the event of a missed daily dose of ERLEADA, they should take their normal dose as soon as possible on the same day with a return to the normal schedule on the following day. The patient should not take extra tablets to make up the missed dose [see Dosage and Administration (2.1)].

Embryo-Fetal Toxicity

- Inform patients that ERLEADA can be harmful to a developing fetus. Advise male patients with female partners of reproductive potential to use effective contraception during treatment and for 3 months after the last dose of ERLEADA. Advise male patients to use a condom if having sex with a pregnant woman [see Warnings and Precautions (5.3)].

Infertility

- Advise male patients that ERLEADA may impair fertility and not to donate sperm during therapy and for 3 months following the last dose of ERLEADA [see Use in Specific Populations (8.3)].

Manufactured by:
Janssen Ortho LLC
Gurabo, PR 00778

Manufactured for:
Janssen Products, LP
Horsham, PA 19044

© 2019 Janssen Pharmaceutical Companies

| |
|---|
| PATIENT INFORMATION<br>ERLEADA® (er lee'dah)<br>(apalutamide)<br>Tablets |
| What is ERLEADA?<br>ERLEADA is a prescription medicine used for the treatment of prostate cancer:<br>• that has spread to other parts of the body and still responds to a medical or surgical treatment that lowers testosterone, OR<br>• that has not spread to other parts of the body and no longer responds to a medical or surgical treatment that lowers testosterone<br><br>It is not known if ERLEADA is safe and effective in females.<br>It is not known if ERLEADA is safe and effective in children. |
| Before taking ERLEADA, tell your healthcare provider about all your medical conditions, including if you:<br>• have a history of heart disease<br>• have high blood pressure<br>• have diabetes<br>• have abnormal amounts of fat or cholesterol in your blood (dyslipidemia)<br>• have a history of seizures, brain injury, stroke, or brain tumors<br>• are pregnant or plan to become pregnant. ERLEADA can cause harm to your unborn baby and loss of pregnancy (miscarriage).<br>• have a partner who is pregnant or may become pregnant.<br>　○ Males who have female partners who are able to become pregnant should use effective birth control (contraception) during treatment and for 3 months after the last dose of ERLEADA.<br>　○ Males should use a condom during sex with a pregnant female.<br>　Talk with your healthcare provider if you have questions about birth control.<br>• are breastfeeding or plan to breastfeed. It is not known if ERLEADA passes into breast milk.<br><br>Tell your healthcare provider about all the medicines you take, including prescription and over-the-counter medicines, vitamins, and herbal supplements. ERLEADA can interact with many other medicines.<br>You should not start or stop any medicine before you talk with the healthcare provider that prescribed ERLEADA.<br>Know the medicines you take. Keep a list of them with you to show to your healthcare provider and pharmacist when you get a new medicine. |
| How should I take ERLEADA?<br>• Take ERLEADA exactly as your healthcare provider tells you.<br>• Your healthcare provider may change your dose if needed.<br>• Do not stop taking your prescribed dose of ERLEADA without talking with your healthcare provider first.<br>• Take your prescribed dose of ERLEADA 1 time a day, at the same time each day.<br>• Take ERLEADA with or without food<br>• Swallow ERLEADA tablets whole.<br>• If you miss a dose of ERLEADA, take your normal dose as soon as possible on the same day. Return to your normal schedule on the following day. You should not take extra tablets to make up the missed dose.<br>• You should start or continue a gonadotropin-releasing hormone (GnRH) analog therapy during your treatment with ERLEADA unless you have had a surgery to lower the amount of testosterone in your body (surgical castration).<br>• If you take too much ERLEADA, call your healthcare provider or go to the nearest hospital emergency room. |
| What are the possible side effects of ERLEADA?<br>ERLEADA may cause serious side effects including:<br>• Heart Disease. Blockage of the arteries in the heart that can lead to death has happened in some people during treatment with ERLEADA. Your healthcare provider will monitor you for signs and symptoms of heart problems during your treatment with ERLEADA. Call your healthcare provider or go to the nearest emergency room right away if you | get chest pain or discomfort at rest or with activity, or shortness of breath during your treatment with ERLEADA.
- Fractures and falls. ERLEADA treatment can cause bones and muscles to weaken and may increase your risk for falls and fractures. Falls and fractures have happened in people during treatment with ERLEADA. Your healthcare provider will monitor your risks for falls and fractures during treatment with ERLEADA.
- Seizure. Treatment with ERLEADA may increase your risk of having a seizure. You should avoid activities where a sudden loss of consciousness could cause serious harm to yourself or others. Tell your healthcare provider right away if you have a loss of consciousness or seizure. Your healthcare provider will stop ERLEADA if you have a seizure during treatment.

The most common side effects of ERLEADA include:
- feeling very tired
- joint pain
- rash. Tell your healthcare provider if you get a rash
- decreased appetite
- fall
- weight loss
- hypertension
- hot flash
- diarrhea
- fracture ERLEADA may cause fertility problems in males, which may affect the ability to father children. Talk to your healthcare provider if you have concerns about fertility. Do not donate sperm during treatment with ERLEADA and for 3 months after the last dose of ERLEADA.

Tell your healthcare provider if you have any side effect that bothers you or that does not go away.
These are not all the possible side effects of ERLEADA.
Call your doctor for medical advice about side effects. You may report side effects to FDA at 1-800-FDA-1088.

How should I store ERLEADA?
- Store ERLEADA at room temperature between 68°F to 77°F (20°C to 25°C).
- Store ERLEADA in the original package.
- The bottle of ERLEADA contains a desiccant packet to help keep your medicine dry (protect it from moisture). Do not throw away (discard) the desiccant.
- Protect ERLEADA from light and moisture.

Keep ERLEADA and all medicines out of the reach of children.

General information about the safe and effective use of ERLEADA.
Medicines are sometimes prescribed for purposes other than those listed in a Patient Information leaflet. Do not use ERLEADA for a condition for which it was not prescribed. Do not give ERLEADA to other people, even if they have the same symptoms that you have. It may harm them. If you would like more information, talk with your healthcare provider. You can ask your healthcare provider or pharmacist for information about ERLEADA that is written for health professionals.

What are the ingredients in ERLEADA?
Active ingredient: apalutamide
Inactive ingredients: colloidal anhydrous silica, croscarmellose sodium, hydroxypropyl methylcellulose-acetate succinate, magnesium stearate, microcrystalline cellulose, and silicified microcrystalline cellulose. The film-coating contains iron oxide black, iron oxide yellow, polyethylene glycol, polyvinyl alcohol, talc, and titanium dioxide.

Manufactured by: Janssen Ortho LLC, Gurabo, PR 00778
Manufactured for: Janssen Products, LP, Horsham, PA 19044
© 2019 Janssen Pharmaceutical Companies
For more information, call Janssen Products, LP at 1-800-526-7736 (1-800-JANSSEN) or go to www.erleada.com.
This Patient Information has been approved by the U.S. Food and Drug Administration.                                     Revised: 09/2019

The examples and embodiments described herein are for illustrative purposes only and various modifications or changes suggested to persons skilled in the art are to be included within the spirit and purview of this application and scope of the appended claims

The invention claimed is:

1. A method for treating metastatic castration-sensitive prostate cancer in a male human consisting essentially of administering a therapeutically effective amount of an anti-androgen to a male human with metastatic castration-sensitive prostate cancer, wherein the anti-androgen is 4-[7-(6-cyano-5-trifluoromethylpyridin-3-yl)-8-oxo-6-thioxo-5,7-diazaspiro[3.4]oct-5-yl]-2-fluoro-N-methylbenzamide.

2. The method of claim 1, wherein administration of the anti-androgen provides an increase in overall survival of the male human relative to the overall survival rate of a population of male humans with the metastatic castration-sensitive prostate cancer, said population having been administered a placebo in combination with an androgen deprivation therapy.

3. The method of claim 1, wherein administration of the anti-androgen provides an increase in progression-free survival of the male human relative to the progression-free survival rate of a population of male humans with the metastatic castration-sensitive prostate cancer, said population having been administered a placebo in combination with an androgen deprivation therapy.

4. The method of claim 1, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human.

5. The method of claim 1, wherein 4-[7-(6-cyano-5-trifluoromethylpyridin-3-yl)-8-oxo-6-thioxo-5,7-diazaspiro[3.4]oct-5-yl]-2-fluoro-N-methylbenzamide is administered orally to the male human at a dose of about 240 mg per day.

6. The method of claim 1, wherein the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 180 mg per day or 120 mg per day if the male human experiences a greater than or equal to Grade 3 toxicity.

7. The method of claim 1, wherein the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 180 mg per day if the male human experiences a greater than or equal to Grade 3 toxicity.

8. The method of claim 1, wherein the dose of 4-[7-(6-cyano-5-trifluoromethylpyridin-3-yl)-8-oxo-6-thioxo-5,7-diazaspiro[3.4]oct-5-yl]-2-fluoro-N-methylbenzamide is decreased to 120 mg per day if the male human experiences a greater than or equal to Grade 3 toxicity.

* * * * *